(12) United States Patent
Holbrook et al.

(10) Patent No.: US 12,121,651 B2
(45) Date of Patent: Oct. 22, 2024

(54) INSUFFLATION RETENTION DEVICE WITH BALLOON

(71) Applicant: BPENDO, LLC, Norman, OK (US)

(72) Inventors: Robert M Holbrook, Norman, OK (US); Robert Henson, Morrisville, NC (US); James Fentress, Morrisville, NC (US); Jay Zignego, Morrisville, NC (US); Peter Smith, Morrisville, NC (US); Amanda Schaffers, Morrisville, NC (US)

(73) Assignee: BPENDO, LLC, Norman, OK (US)

( * ) Notice: Subject to any disclaimer, the term of this patent is extended or adjusted under 35 U.S.C. 154(b) by 922 days.

(21) Appl. No.: 17/176,138

(22) Filed: Feb. 15, 2021

(65) Prior Publication Data

US 2021/0162145 A1    Jun. 3, 2021

Related U.S. Application Data

(63) Continuation of application No. 16/501,637, filed on May 13, 2019, now Pat. No. 10,918,815, and a
(Continued)

(51) Int. Cl.
*A61M 13/00* (2006.01)
*A61B 17/34* (2006.01)
*A61B 1/31* (2006.01)

(52) U.S. Cl.
CPC ....... *A61M 13/003* (2013.01); *A61B 17/3423* (2013.01); *A61B 1/31* (2013.01);
(Continued)

(58) Field of Classification Search
CPC ............... A61M 13/003; A61M 13/00; A61B 2017/3492; A61B 2017/3486;
(Continued)

(56) References Cited

U.S. PATENT DOCUMENTS 3,154,077 A    10/1964    Cannon
3,745,992 A     7/1973    Poirier
(Continued)

FOREIGN PATENT DOCUMENTS

JP    H4226620       5/1991
JP    H0923560 A    1/1997
(Continued)

OTHER PUBLICATIONS

China Patent Office action for CPME1944766P mailed Feb. 8, 2022, 1-16.
(Continued)

*Primary Examiner* — James D Ponton
*Assistant Examiner* — Hong-Van N Trinh
(74) *Attorney, Agent, or Firm* — Michael S. Young IP Law LLC; Michael S. Young

(57) ABSTRACT

A probe may be inserted into a body cavity to perform diagnostic intervention(s), therapeutic intervention(s), or both. The probe may be inserted through a body aperture that is naturally occurring or man-made, intentionally or by accident. The body aperture may form a seal encircling the probe so that insufflation retention material may be effectively retained in the body cavity so that an operator can perform the intervention(s). However, there may be leakage of the insufflation material. The insufflation retention device is configured to form an effective seal contactingly adjacent the body aperture and to provide a passageway for the introduction of the probe into the body cavity, such that a diagnostic intervention or therapeutic intervention or both may be performed.

5 Claims, 39 Drawing Sheets

Related U.S. Application Data continuation-in-part of application No. 15/976,885, filed on May 11, 2018, now Pat. No. 11,273,269, said application No. 16/501,637 is a continuation-in-part of application No. 15/976,885, filed on May 11, 2018, now Pat. No. 11,273,269.

(60) Provisional application No. 62/920,037, filed on Apr. 9, 2019, provisional application No. 62/505,095, filed on May 11, 2017.

(52) U.S. Cl.
CPC .............. *A61M 2205/0216* (2013.01); *A61M 2205/0222* (2013.01); *A61M 2210/1064* (2013.01)

(58) Field of Classification Search
CPC .... A61B 2017/3441; A61B 2017/3429; A61B 2017/3419; A61B 2017/00557; A61B 17/3462; A61B 17/3423; A61B 1/31; A61B 1/00082
See application file for complete search history.

(56) References Cited

U.S. PATENT DOCUMENTS

| | | | |
|---|---|---|---|
| 3,802,418 A * | 4/1974 | Clayton | A61F 2/0013 600/562 |
| 4,776,845 A | 10/1988 | Davis | |
| 4,957,486 A | 9/1990 | Davis | |
| 4,984,564 A | 1/1991 | Yuen | |
| 5,366,478 A * | 11/1994 | Brinkerhoff | A61B 17/3423 49/477.1 |
| 5,545,179 A * | 8/1996 | Williamson, IV | A61B 17/3423 600/32 |
| 5,725,553 A * | 3/1998 | Moenning | A61B 17/3423 606/213 |
| 5,836,048 A | 11/1998 | Rossman | |
| 5,904,701 A | 5/1999 | Daneshvar | |
| 5,964,781 A | 10/1999 | Mollenauer | |
| 6,768,058 B2 | 7/2004 | Pallapothu | |
| 6,811,546 B1 * | 11/2004 | Callas | A61B 17/3423 604/167.06 |
| 7,967,809 B2 | 6/2011 | Jay-Robinson | |
| 8,057,448 B2 | 11/2011 | Williams | |
| 8,235,942 B2 | 8/2012 | Frassica | |
| 8,419,695 B2 | 4/2013 | Rauker | |
| 8,939,952 B2 | 1/2015 | Weig | |
| 8,979,884 B2 | 3/2015 | Milsom | |
| 9,924,853 B2 | 3/2018 | Milsom | |
| 9,986,893 B2 | 6/2018 | Cornhill | |
| 10,149,601 B2 | 12/2018 | Cornhill | |
| 10,485,401 B2 | 11/2019 | Cruz | |
| 2001/0047188 A1 * | 11/2001 | Bonadio | A61B 17/3423 2/161.7 |
| 2003/0208223 A1 | 11/2003 | Kleiner | |
| 2004/0127772 A1 * | 7/2004 | Ewers | A61B 90/30 600/212 |
| 2005/0165432 A1 | 7/2005 | Heinrich | |
| 2006/0020164 A1 | 1/2006 | Butler | |
| 2006/0271095 A1 * | 11/2006 | Rauker | A61B 1/31 606/197 |
| 2007/0005086 A1 | 1/2007 | Gresham | |
| 2007/0213661 A1 * | 9/2007 | Gobel | A61F 2/0013 604/96.01 |
| 2008/0092901 A1 | 4/2008 | Kang | |
| 2009/0312701 A1 * | 12/2009 | Gobel | A61B 17/3423 604/96.01 |
| 2009/0326490 A1 | 12/2009 | McMichael | |
| 2010/0312066 A1 * | 12/2010 | Cropper | A61B 17/3423 600/207 |
| 2011/0218389 A1 | 9/2011 | Gobel | |
| 2013/0012966 A1 | 1/2013 | Park | |
| 2014/0018625 A1 | 1/2014 | Lal | |
| 2014/0066953 A1 | 3/2014 | Keating | |
| 2014/0296831 A1 | 10/2014 | Gobel | |
| 2019/0069761 A1 | 3/2019 | Milsom | |
| 2019/0133420 A1 | 5/2019 | Cornhill | |
| 2019/0343372 A1 | 11/2019 | Cornhill | |
| 2022/0240762 A1 | 8/2022 | Rentschler | |

FOREIGN PATENT DOCUMENTS

| | | |
|---|---|---|
| JP | 20105391 | 1/2010 |
| JP | 2011514202 A | 5/2011 |
| JP | 201245398 | 3/2012 |
| JP | 2015062441 A | 4/2015 |
| WO | 9422357 A2 | 10/1994 |
| WO | 2006126061 A1 | 11/2006 |
| WO | 2015123313 A1 | 8/2015 |
| WO | 2015164591 A1 | 10/2015 |

OTHER PUBLICATIONS

Extended European search report for International application No. PCT/US2019/000024, N420603EP MPR mailed Mar. 12, 2021, pp. 1-10.

Extended European search report mailed N419691 EP MPR International Application No. PCT/US2018032373 mailed Jan. 28, 2021, pp. 1-8.

Flexi-Seal REF41800 webpage capture, last visited Dec. 13, 2018.

Flexi-Seal REF418000 package insert, package usage date through Oct. 1, 2021.

International Preliminary Report on Patentability for International application No. PCT/US2019/000024 mailed Nov. 17, 2020, pp. 1-6.

International Search Report for International Application No. PCT/US18/32373 mailed Aug. 1, 2018, pp. 1-18.

International Search Report for International Application No. PCT/US19/00024 mailed Oct. 24, 2019, pp. 1-12.

Japan Patent Office action for Japan Patent Application No. 2020-513485 mailed Mar. 25, 2022, pp. 1-8.

Japan Patent Office refusal for Japan Patent Application No. 2020-563428 mailed Jun. 13, 2023, pp. 1-6.

Japan Patent Office refusal for Japan Patent Application No. 2020-563428 mailed Feb. 24, 2024, pp. 1-4.

Republic of Korea Official action for Application No. KR2019-7036524 mailed May 22, 2023, pp. 1-10.

Republic of Korea Official action for Application No. KR2019-7036524mailed Dec. 26, 2023, pp. 1-3.

Republic of Korea Official action for Application No. KR2020-7035211 mailed Sep. 14, 2022, pp. 1-10.

Technology Status Evaluation Report: Methods of luminal distention for colonoscopy, Gastrointestinal Endoscopy, vol. 77, No. 4, 2013, pp. 519-525.

\* cited by examiner

INSUFFLATION RETENTION DEVICE WITH BALLOON

RELATED APPLICATIONS

The current application claims priority to U.S. patent application Ser. No. 16/501,637, U.S. Prov. Pat. App. 62/920,037; U.S. patent application Ser. No. 15/976,885; and U.S. Prov. Pat. App. No. 62/505,095.

The current application is a continuation application that claims priority to U.S. patent application Ser. No. 16/501,637, entitled Insufflation Retention Device with Balloon, with filing date May 13, 2019.

U.S. patent application Ser. No. 16/501,637 claims priority to U.S. Prov. Pat. App. No. 62/920,037, entitled Insufflation Retention Device with Balloon, with filing date Apr. 9, 2019. U.S. patent application Ser. No. 16/501,637 was with U.S. Prov. Pat. App. 62/920,037 when U.S. patent application Ser. No. 16/501,637 was filed.

U.S. patent application Ser. No. 16/501,637 is a continuation-in-part that claims priority to U.S. patent application Ser. No. 15/976,885, entitled Insufflation Retention Device, with filing date May 11, 2018. U.S. patent application Ser. No. 16/501,637 was with U.S. patent application Ser. No. 15/976,885 when U.S. patent application Ser. No. 16/501,637 was filed. U.S. patent application Ser. No. 15/976,885 claims priority to U.S. Prov. Pat. App. No. 62/505,095, entitled Insufflation Retention Device, with filing date May 11, 2017. U.S. patent application Ser. No. 15/976,885 was with U.S. Prov. Pat. App. No. 62/505,095 when U.S. patent application Ser. No. 15/976,885 was filed.

The current application is a continuation-in-part that claims priority to U.S. patent application Ser. No. 15/976,885. The current application is copending with U.S. patent application Ser. No. 15/976,885.

U.S. patent application Ser. No. 16/501,637, U.S. Prov. Pat. App. 62/920,037; U.S. patent application Ser. No. 15/976,885; and U.S. Prov. Pat. App. No. 62/505,095 are all hereby incorporated by reference in their entirety.

SUMMARY

In accordance with various embodiments, a probe may be inserted into a body cavity to perform diagnostic intervention(s), therapeutic intervention(s), or both. The probe may be inserted through a body aperture that is naturally occurring or man-made, intentionally or by accident. The body aperture may form a seal encircling the probe so that insufflation retention material may be effectively retained in the body cavity so that an operator can perform the intervention(s), in which case a body probe seal is considered competent. However, there may be leakage of the insufflation material, in which case the body probe seal is considered incompetent. The insufflation retention device is configured to form an effective seal contactingly adjacent the body aperture and to provide a passageway for the introduction of the probe into the body cavity to create a competent seal between the body aperture and the insufflation retention device and another competent seal between the probe and the insufflation retention device.

BRIEF DESCRIPTION OF THE DRAWINGS

FIG. 60 (B) shows in close-up the valve of FIG. 60 (A) in accordance with various embodiments.

DETAILED DESCRIPTION

There are technologies that allow operators to introduce a probe, e.g., a medical scope, into a body cavity for diagnostic intervention or therapeutic intervention or both. When the probe is introduced, the body cavity may need to be expanded for the operator to perform the intervention(s). Using an insufflation technique, the operator may introduce an insufflation material to expand the body cavity, so the operator may have more room to work and better visibility in the body cavity to perform the intervention(s). E.g., see Technology Status Evaluation Report: Methods of luminal distension for colonoscopy, Gastrointestinal Endoscopy, Volume 77, No. 4, 2013, pages 519-525, which is incorporated by reference in its entirety. The insufflation material may be air, carbon dioxide, water, or other suitable materials.

The operator may start with the probe outside a body, and the operator may advance the probe through tissue of the body to introduce the probe into a cavity of the body, i.e., the body cavity. The probe may be advanced through the tissue via an aperture of the body, i.e., the body aperture, that is a naturally occurring orifice, e.g., an anus, or a wound, e.g., a surgical incision or a traumatic injury. The body aperture may have elasticity that allows the body aperture to recover its size and shape after any deformation from the probe being advanced through the body aperture into the body cavity to effectively seal the outside of the body from the body cavity. Thereafter, the insufflation material introduced into the body cavity may be retained in the body cavity to help promote expansion of the body cavity when the outside of the body is effectively sealed from the body cavity to permit the operator to perform the intervention(s).

However, the insufflation material may not be effectively retained in the body cavity in some instances. For example, the body aperture or nearby structures may have a congenital malformation or may have suffered structural injury such as from scar tissue formation after abscess formation, surgical trauma, giving birth related injury, etc. that inhibits the body aperture from forming an effective seal with the probe.

If the insufflation material is not effectively retained, then the operator will not have time and room to work or visibility to operate in the body cavity. For example, the probe, such as an endoscope, may be introduced into the body cavity, such as a rectum and a large intestine, through the body aperture, such as the anus, and the elasticity of the body aperture may not effectively form a seal contactingly adjacent the probe to promote retention of the insufflation material in the body cavity. As will be described in further detail, this disclosure describes an insufflation retention device that promotes retention of the insufflation material in the body cavity.

Figure 1:
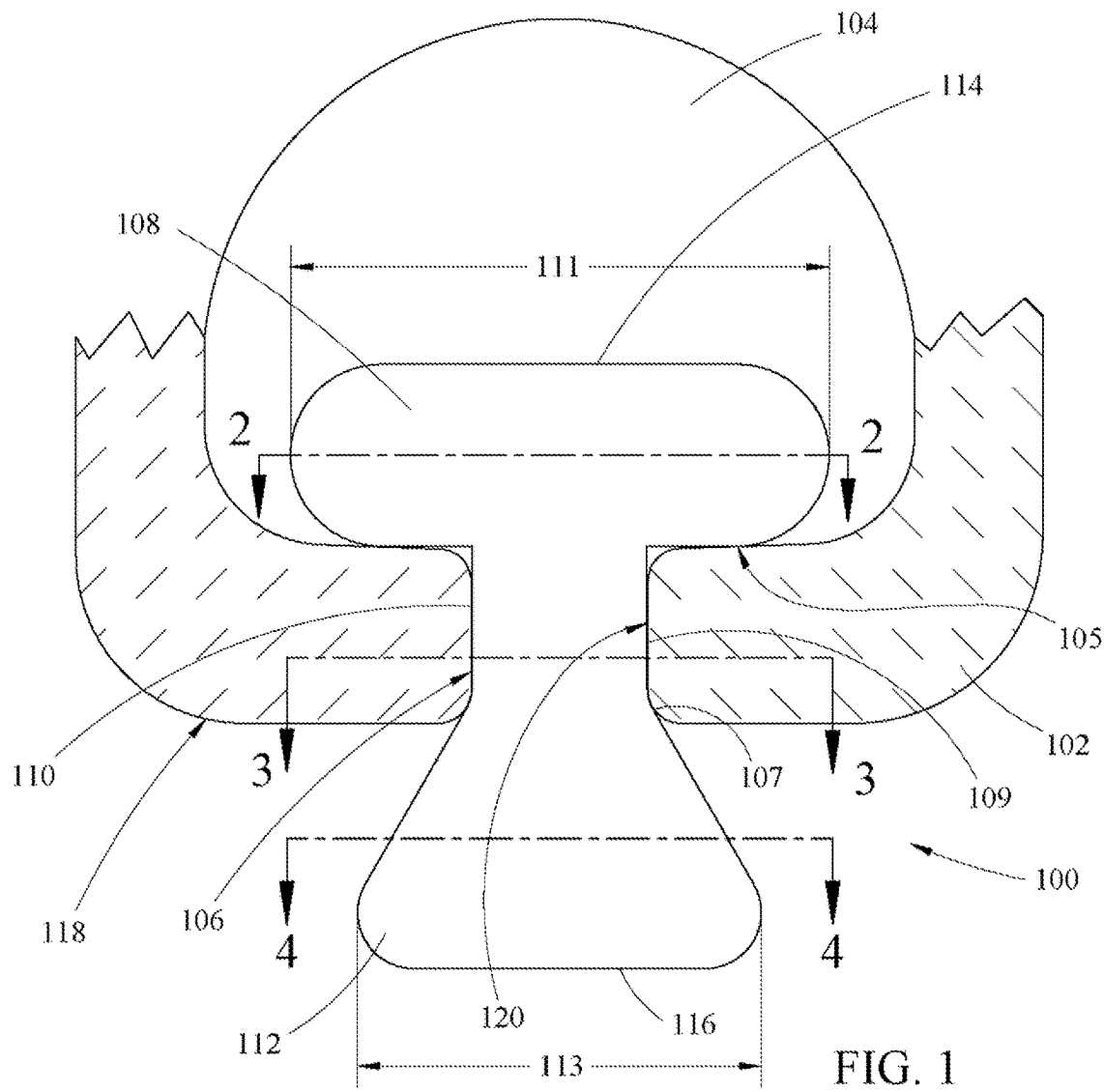
FIG. 1 shows in partial cross-section view an insufflation retention device through a body aperture and in a body cavity in accordance with various embodiments.

FIG. 1 shows an apparatus that is an insufflation retention device (also known herein as IRD 100) that has been advanced from outside of a body 102 into a body cavity 104 through a body aperture 106, also known as an orifice. The IRD 100 may generally include an internal buttress 108, a midportion 110, and an external buttress 112. The internal buttress 108 is at a first end 114 of the IRD 100 and the external buttress 112 is at an opposing, second end 116 of the IRD 100 with the midportion 110 therebetween. In other words, the midportion 110 is disposed between the internal buttress 108 and the external buttress 112.

As shown in FIG. 1, a width 111 of the internal buttress 108 may be substantially greater than a width 113 of the external buttress 112. Alternatively, the width 111 of the internal buttress 108 may be substantially equal to the width 113 of the external buttress 112, as shown in later figures. Furthermore, the width 111 of the internal buttress 108 may be substantially less than the width 113 of the external buttress 112, as shown in later figures, also. The width 111 of the internal buttress 108 may be substantially parallel to the width 113 of the external buttress 112. A width of the midportion 110 may be substantially less than the width 111 of the internal buttress 108. A width of the midportion 110 may be substantially less than the width 113 of the external buttress 112. The width of the midportion 110 may be substantially parallel to the width 111 of the internal buttress 108.

The width of the midportion 110 may be substantially parallel to the width 113 of the external buttress 112.

The internal buttress 108 may be configured to have an unexpanded configuration so that an operator may introduce the IRD 100 through the body aperture 106 into the body cavity 104. The unexpanded configuration of the internal buttress 108 may be smaller than an expanded configuration of the internal buttress 108 shown in FIG. 1. The unexpanded configuration of the internal buttress 108 is configured to facilitate entry of the IRD 100 from an exterior 118 of the body 102. In other words, in a contracted state the internal buttress 108 may be configured for insertion through the body aperture 106 of the body 102 into the body cavity 104 of the body 102.

The expanded configuration of the internal buttress 108 is configured to prevent the IRD 100 from being removed from the body cavity 104. If the IRD 100 moved towards the exterior 118 of the body 102, then the expanded configuration of the internal buttress 108 would contactingly engage the body cavity 104 or the body aperture 106 or both to prevent the IRD 100 from being removed from the body cavity 104. In other words, in the expanded state the internal buttress 108 may be configured to inhibit removal of the internal buttress 108 from the body cavity 104 through the body aperture 106.

The internal buttress 108 in an unexpanded configuration or contracted state may be increased in size to the expanded configuration or state through introduction of an expansion material into an internal cavity of the internal buttress 108 supplied by a source.

The expansion material may be broadly considered to be a fluid. Examples of the expansion material may be a liquid e.g., water, and a gas e.g., oxygen, air, compressed air, carbon dioxide, by way of example and not limitation.

The internal buttress 108 may be configured to form a body internal buttress seal 105 between the body cavity 104 and the internal buttress 108. The body internal buttress seal 105 may or may not include a wall of the rectum between the body cavity 104 and the internal buttress 108, when the body cavity 104 is part of the lower gastrointestinal system. The body internal buttress seal 105 may or may not include all the wall of the rectum between the body cavity 104 and the internal buttress 108. The internal buttress 108 is shown generally as a doughnut shape; however, other shapes are contemplated depending on the need of the operator in view of the body 102 of a patient. The shape of the internal buttress 108 may be chosen to be a predetermined shape to effectively form the body internal buttress seal 105 between the body 102 and the internal buttress 108. Effectiveness of the body internal buttress seal 105 occurs when insufflation material is retained in the body cavity 104 so that the operator can perform the intervention(s) and the operator will have time and room to work or visibility to operate in the body cavity 104.

The external buttress 112 may be considered to have an unexpanded configuration or contracted state, also. However, the unexpanded configuration of the external buttress 112 is not required. The reason that the unexpanded configuration of the external buttress 112 is not required is that the external buttress 112 is configured to prevent the IRD 100 from being introduced into the body cavity 104. For example, the external buttress 112 may have the unexpanded configuration that is not configured to prevent introduction of the IRD 100 into the body cavity 104. In this example, a user or operator could then transform or transition the unexpanded configuration of the external buttress 112 into the expanded configuration of the external buttress 112 to prevent the IRD 100 from being introduced into the body cavity 104. In other words, the external buttress 112 may be configured to inhibit advancement of the external buttress 112 through the body aperture 106 into the body cavity 104.

As with the internal buttress 108, the external buttress 112 in an unexpanded configuration may be increased in size to the expanded configuration or state through introduction of an expansion material into an internal cavity of the external buttress 112 supplied by a source. The expansion material may again be broadly considered to be a fluid. The expansion material used to expand the internal buttress 108 and the external buttress 112 may be the same or different in any given situation.

However, the external buttress 112 need not have a smaller or unexpanded configuration, because the external buttress 112 does not need to be introduced through the body aperture 106. Therefore, the external buttress 112 may be of a size and configuration that is substantially the same before and after introduction of the IRD 100 into the body 102, and the external buttress 112 may be of a size and configuration that is substantially the same before, during, and after use of the IRD 100 in the body 102. However, for other practical considerations, it may be convenient for the external buttress 112 to have a smaller unexpanded configuration. For example, the external buttress 112 in the unexpanded configuration may more easily fit into a medical kit or packaging.

The external buttress 112 may be configured to form a body external buttress seal 107 between the body 102 and the external buttress 112. The external buttress 112 is shown generally as a cone shape; however, other shapes are contemplated depending on the need of the operator in view of the body 102 of the patient. The shape of the external buttress 112 may be chosen to be a predetermined shape to effectively form the body external buttress seal 107 between the body 102 and the external buttress 112. Effectiveness of the body external buttress seal 107 occurs when insufflation material is retained in the body cavity 104 so that the operator can perform the intervention(s) and the operator will have time and room to work or visibility to operate in the body cavity 104.

The midportion 110 is configured to couple the internal buttress 108 to the external buttress 112. The midportion 110 is configured to contactingly engage a wall 120 of the body aperture 106.

The midportion may be configured to form a body midportion seal 109 between the body aperture 106 and the midportion 110. The midportion 110 is generally shown as a cylinder; however, other shapes are contemplated depending on the need of the operator in view of the body 102 of the patient. The shape of the midportion 110 may be chosen to be a predetermined shape to effectively form the body midportion seal 109 between the body 102 and the midportion 110. Effectiveness of the body midportion seal 109 occurs when insufflation material is retained in the body cavity 104 so that the operator can perform the intervention(s) and the operator will have time and room to work or visibility to operate in the body cavity 104.

Figure 2:
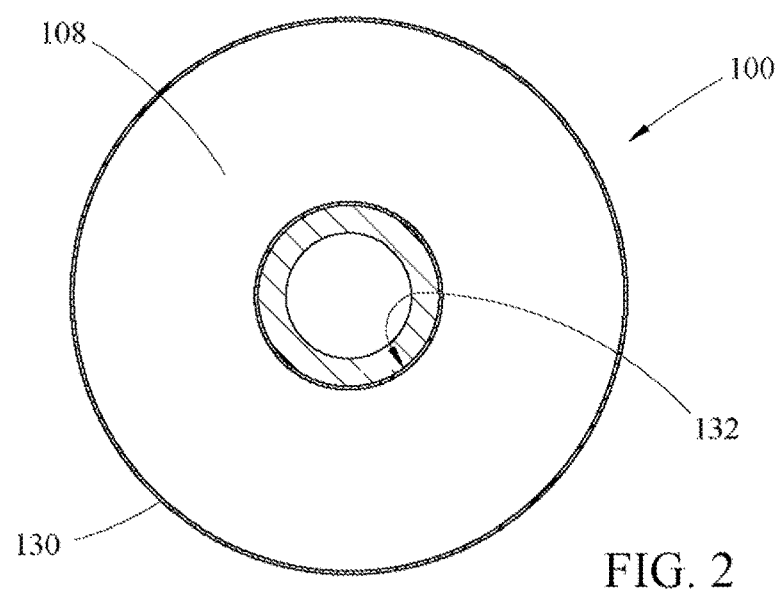
FIG. 2 shows in cross-section view the insufflation retention device of FIG. 1 in accordance with various embodiments.

FIG. 2 shows in cross-section the internal buttress of the IRD 100 of the embodiment shown in FIG. 1. An exterior periphery 130 of the internal buttress 108 may be configured to be expandable from the unexpanded configuration to the expanded configuration shown. An interior periphery 132 of the internal buttress 108 may be configured to be relatively rigid in comparison to the exterior periphery 130. This relatively rigidity of the interior periphery 132 of the internal buttress 108 may help the IRD 100 maintain its configuration and size when the probe is introduced into the IRD 100 and the probe moved back and forth, and in rotation within the IRD 100 when the operator performs the intervention(s).

Figure 3:
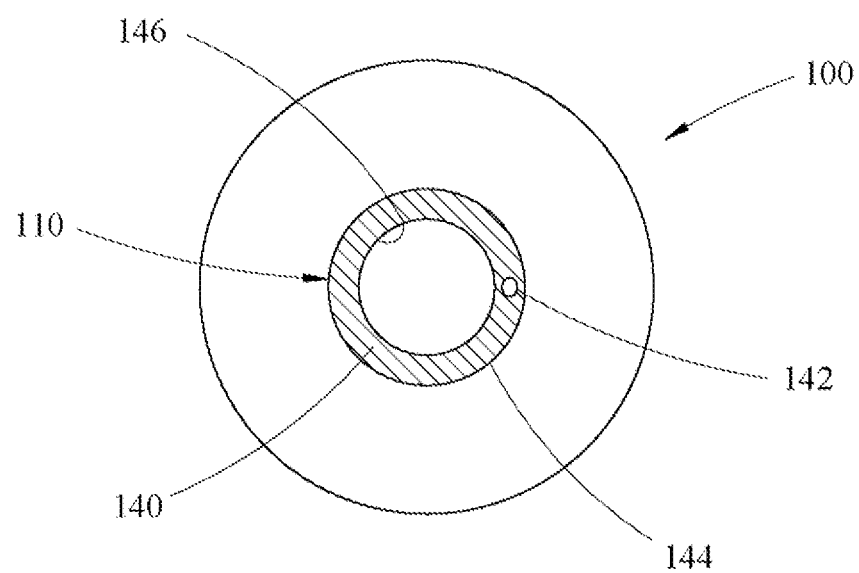
FIG. 3 shows in cross-section view the insufflation retention device of FIG. 1 in accordance with various embodiments.

FIG. 3 shows in cross-section the midportion of the IRD 100 of the embodiment shown in FIG. 1. Within a body 140 of the midportion 110, there may be an expansion material conduit 142 that may be used by the operator to introduce the expansion material into the internal cavity of the internal buttress 108. As can be seen, an exterior surface 144 of the midportion 110 may be substantially circular so that the IRD 100 may be relatively free to rotate clockwise or counter-clockwise within the body aperture 106 as the operator inserts the IRD 100 into the body aperture 106, performs the intervention(s), or removes the IRD 100 from the body aperture 106. Likewise, an interior surface 146 of the midportion 110 may be substantially circular so that the IRD 100 may be relatively free to rotate clockwise or counter-clockwise about the probe as the operator inserts the probe into the IRD 100, performs the intervention(s), removes the probe from the IRD 100, or attaches the IRD 100 to the probe. The exterior surface 144 of the midportion may be substantially parallel the interior surface 146 of the midportion. In other words, the midportion 110 may be a cylinder. As shown in FIG. 1, the midportion 110 may be a right circular hollow cylinder or cylindrical shell.

The interior surface 146 of the midportion 110 may be considered a sleeve that encircles the probe when the midportion 110 is in use. As shown, the sleeve may be substantially circular and disposed symmetrically within the body 140 of the midportion 110. Alternatively, the sleeve may be disposed asymmetrically within the body 140 of the midportion 110.

Figure 4:
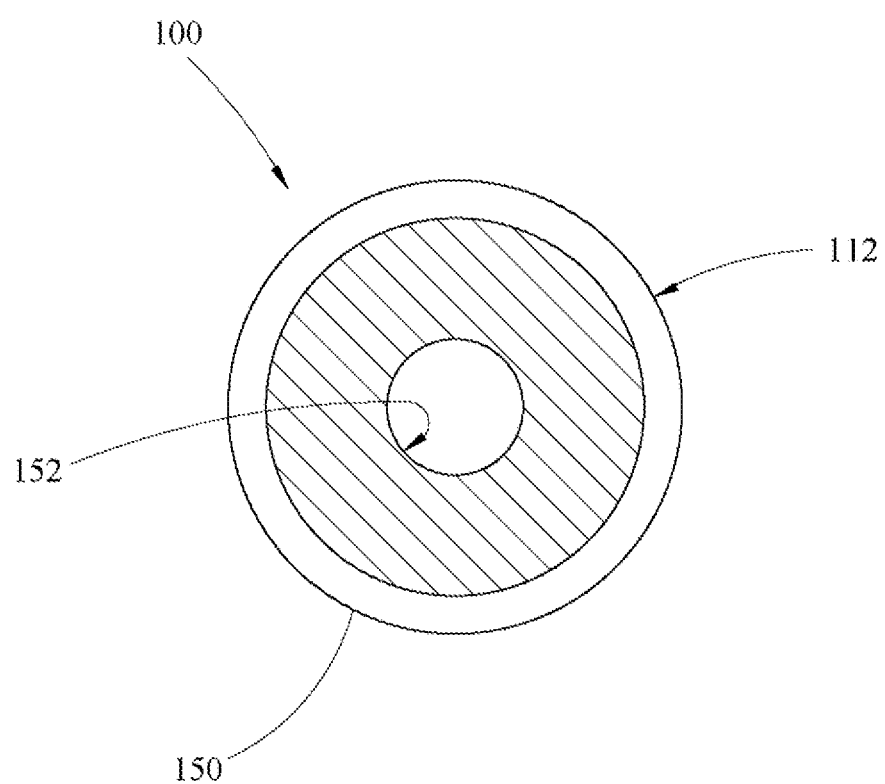
FIG. 4 shows in cross-section view the insufflation retention device of FIG. 1 in accordance with various embodiments.

FIG. 4 shows in cross-section the external buttress 112 of the IRD 100 of the embodiment shown in FIG. 1. An exterior periphery 150 of the external buttress 112 may be configured to be expandable from the unexpanded configuration to the expanded configuration. An interior surface 152 of the external buttress 112 may be configured to be relatively rigid in comparison to the exterior periphery 150. This relatively rigidity of the interior surface 152 of the external buttress may help the IRD 100 maintain its configuration so that the probe may be introduced into the IRD 100 and the probe moved back and forth, and in rotation within the IRD 100 when the operator performs the intervention(s).

The IRD 100 may be made of one or more biologically compatible materials. The biocompatible material may be a polymer, such as silicone or latex. The same polymer may be used for the internal buttress 108 and the external buttress 112 or different polymers may be used for the internal buttress 108 and the external buttress 112. The same polymer may be used for the midportion 110 as is used for the internal buttress 108 and the external buttress 112 or different polymers may be used for the midportion 110, the internal buttress 108, and the external buttress 112. The midportion 110 may be formed of one piece with the internal buttress 108 and the external buttress 112, or the midportion 110 may be formed of a different piece from the internal buttress 108 and the external buttress 112. The internal buttress 108 and the external buttress 112 may be formed of different pieces, also. If different pieces are used to the form the IRD 100, then laser welding, etc. may be used to join the pieces.

Figures 5, 6:
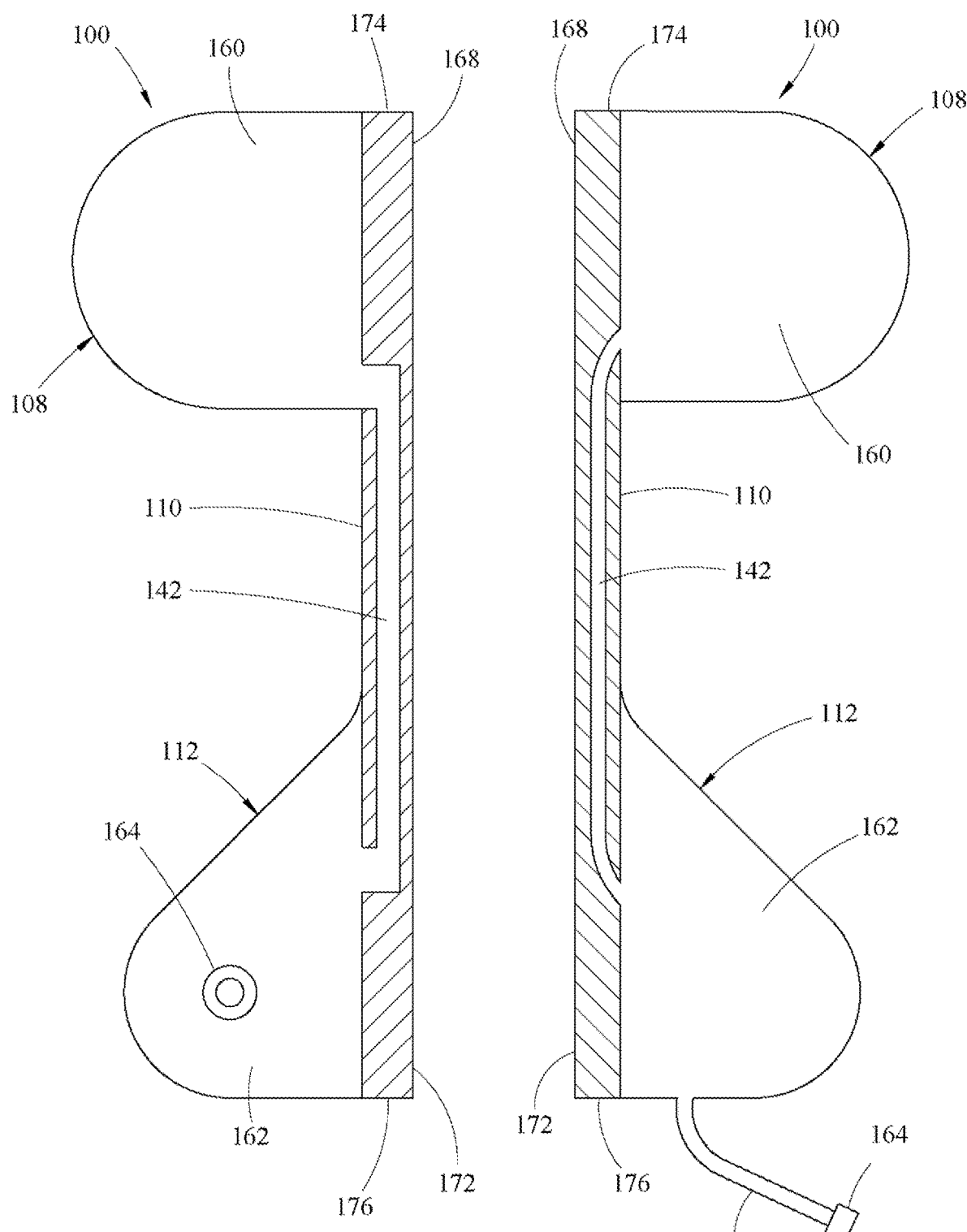
FIG. 5 shows in partial cross-section view a midportion of the insufflation retention device extending as an internal buttress portion and an opposing, external buttress portion in accordance with various embodiments.
FIG. 6 shows in partial cross-section view a midportion of the insufflation retention device extending as an internal buttress portion and an opposing, external buttress portion in accordance with various embodiments.

FIG. 5 shows in cross-section an embodiment of the IRD 100 in which an internal cavity 160 of the internal buttress 108 is in fluid communication with an internal cavity 162 of the external buttress 112 through the expansion material conduit 142 of the midportion 110. The expanded state is shown. An input valve 164 for the expansion material is shown coupled to the external buttress 112. The operator introduces the expansion material through the input valve 164 into the internal cavity 162 of the external buttress 112, the expansion material conduit 142 of the midportion 110, and the internal cavity 160 of the internal buttress 108 using a gas line, a syringe, or other suitable source of the expansion material.

FIG. 6 shows in cross-section another embodiment of the IRD 100 in which the internal cavity 160 of the internal buttress 108 is in fluid communication with the internal cavity 162 of the external buttress 112 through the expansion material conduit 142 of the midportion 110. The expanded state is shown. The input valve 164 for the expansion material is shown coupled to the external buttress 112 through an expansion material line 166 coupled to the external buttress 112. The expansion material line 166 may be rigid, flexible, or some combination of flexible and rigid. When flexible, the expansion material line 166 may assume any suitable orientation and orientation during use. When rigid, the expansion material line may maintain a predetermined orientation and configuration before, during, and after use. The operator introduces the expansion material through the input valve 164 into the expansion material line 166, the internal cavity 162 of the external buttress 112, the expansion material conduit 142 of the midportion 110, and the internal cavity 160 of the internal buttress 108.

FIG. 5 and FIG. 6 show the midportion 110 extending as an internal buttress portion 168 and an opposing, external buttress portion 172. The internal buttress 108 is part of the internal buttress portion 168, and the external buttress 112 is part of the opposing, external buttress portion 172. The internal buttress 108 may extend substantially short of, approximately even with, or substantially beyond a first end 174 of the internal buttress portion 168. The internal buttress 108 is shown approximately even with the first end 174 of the internal buttress portion 168. The external buttress 112 extend substantially short of, approximately even with, or substantially beyond a second end 176 of the external buttress portion 172. The external buttress 112 is shown approximately even with the second end 176 of the external buttress portion 172.

Figure 7:
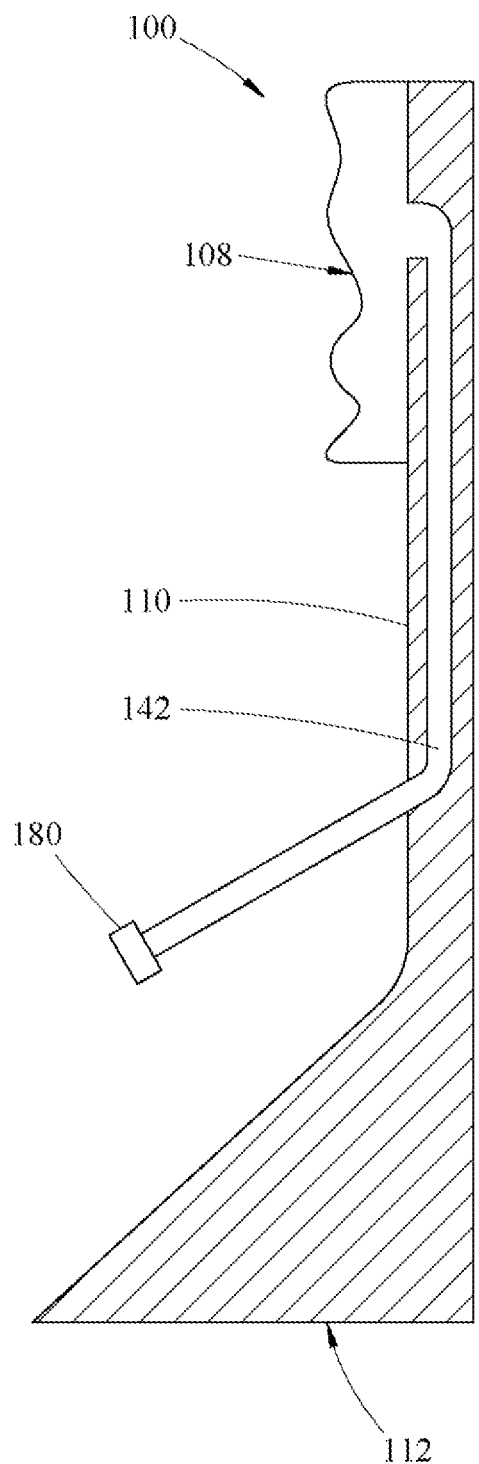
FIG. 7 shows in partial cross-section view an internal buttress input valve in fluid communication with an expansion material conduit in accordance with various embodiments.

The expansion material conduit 142 of the midportion 110 may take any shape. FIG. 5 shows the expansion material conduit 142 starts at substantially right angles to the internal buttress 108 and the external buttress 112, while FIG. 6 shows the expansion material conduit 142 starts at substantially curvilinear orientation to the internal buttress 108 and the external buttress 112. Further, one or more pressure release valves in the IRD 100 may be configured to control when expansion of the external buttress 112 and the internal buttress 108 occur in relation to introduction of the expansion material. The pressure release valves may be of any suitable construction and are not shown. FIG. 7 shows in cross-section another embodiment of the IRD 100 in which an internal buttress input valve 180 is in fluid communication with the expansion material conduit 142 of the midportion 110 to the internal buttress 108, while the external buttress 112 is not in fluid communication with the internal buttress input valve 180. The internal buttress 108 is shown in the unexpanded state. The internal buttress 108 may expand outwards or away from the internal buttress portion 168 (see FIGS. 5-6). Of course, the internal buttress input valve 180 may be in direct fluid communication with the internal buttress 108 without the intervening expansion material conduit 142, which is not shown.

Figure 8:
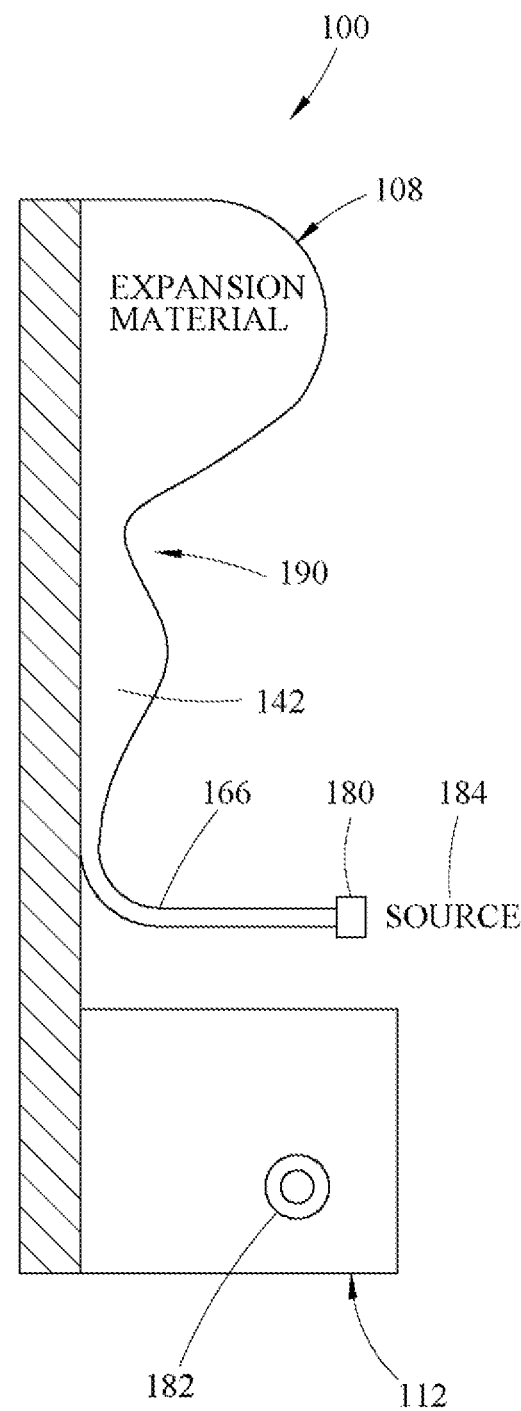
FIG. 8 shows in partial cross-section view an internal buttress input valve in fluid communication with an expansion material conduit and in external buttress with a separate external buttress input valve in accordance with various embodiments.

FIG. 8 shows in cross-section another embodiment of the IRD 100 in which the internal buttress input valve 180 through the expansion material line 166 is in fluid communication with the expansion material conduit 142 to expand the internal buttress 108 via introduction of the expansion material. Further, an external buttress input valve 182 is in fluid communication with the external buttress 112 to expand the external buttress 112 via introduction of the expansion material. In this embodiment of the IRD 100, the internal buttress input valve 180 and the external buttress input valve 182 may be independently operated by the operator or user to expand and contract the internal buttress 108 and expand and contract the external buttress 112 through introduction of the expansion material and removal of the expansion material via the internal buttress input valve 180 and the external buttress input valve 182. The internal buttress 108 is shown expanded by the expansion material supplied by an expansion material source 184. The external buttress 112 is shown to have a rectangular shape as opposed to other buttress shapes previously shown with doughnut shape, conical shape, etc. Any suitable shape may be used for the internal buttress 108 or the external buttress 112.

In addition, the midportion 110 may have an external surface 190 that is not substantially flat. In other embodiments, the external surface 190 of the midportion 110 may be substantially flat. In this embodiment shown in FIG. 8, the external surface 190 of the midportion 110 is contoured, which is not substantially flat. The contour may be chosen by the operator based on anatomy of the body aperture 106 (see FIG. 1) and other features. The contour may help the IRD 100 achieve and maintain an effective seal for retention of the insufflation material. The contour shape and size may be responsive to absence or presence of the expansion material. As shown in FIG. 8, the contour may have the expansion material introduced through the expansion material line 166 that supplies the expansion material to the internal buttress 108. Of course, the contour may have the expansion material introduced through an expansion material line that is different and independent from the expansion material line 166 that supplies the expansion material to the internal buttress 108.

Besides going from a contracted or unexpanded state with less of the expansion material to the expanded state with more of the expansion material, the midportion 110 generally and the contour, as a specific example that is not limiting, may be substantially rigid. In an embodiment with the substantially rigid contour, the midportion 110 does not substantially deform during use of the IRD 100 from the orientation and configuration with respect to the IRD 100 before or after use of the IRD 100.

Figure 9:
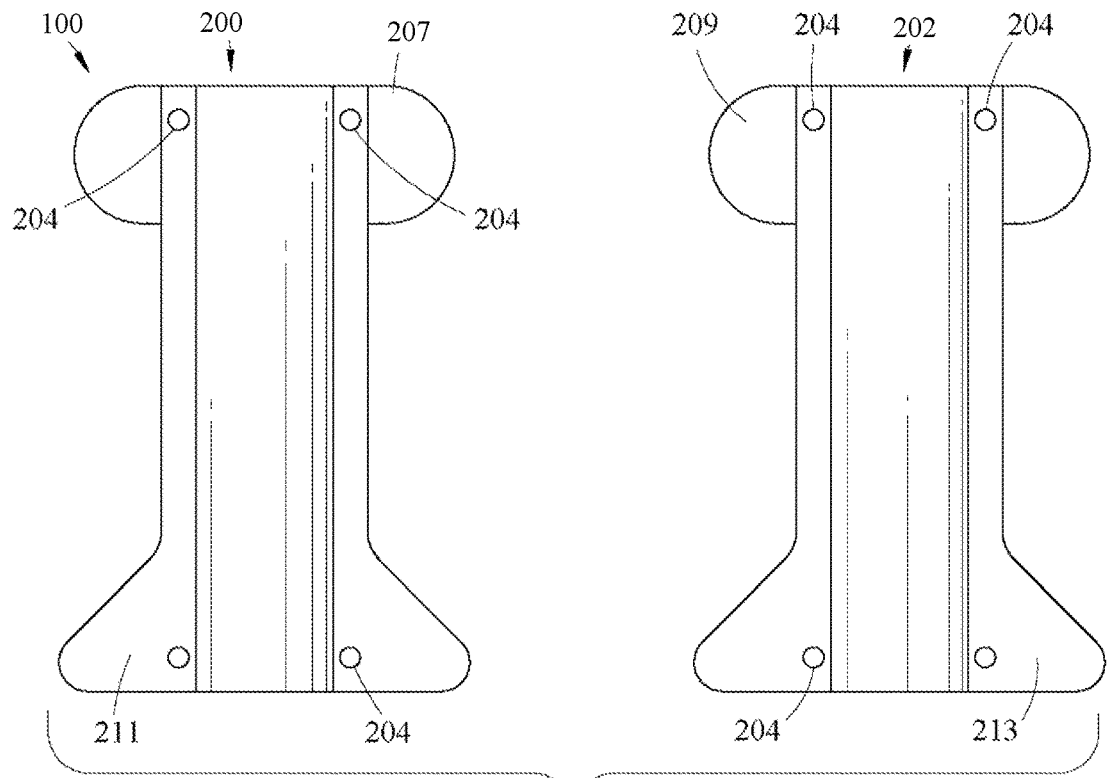
FIG. 9 shows in plan view a first body component and a second body component in accordance with various embodiments.

FIG. 9 shows another embodiment of the IRD 100. In this embodiment, the IRD 100 has a first body component 200 and a second body component 202. The first body component 200 is configured to be coupled to the second body component 202 to form the IRD 100 that is operational for use. The operator may wish to use such a two-body component system when the probe is already in the body aperture 106 or in both the body aperture 106 and the body cavity 104 (see FIG. 1). When the probe is in this position in the body aperture 106 or the body cavity 104, the operator may not be able to insert the probe into and through the IRD 100 or slide the IRD 100 over the probe. On the other hand, the operator will be able to couple the first body component 200 to the second body component 202 around the probe that remains in position in the body aperture 106 or in both the body aperture 106 and the body cavity 104. The first body component 200 may be coupled to the second body component 202 via one or more pairs of fasteners 204 of any suitable type, such as but not limited to snaps, clips, etc. Of course, this embodiment may also be used before the probe is in the body aperture 106 or the body cavity 104 or both.

As shown in this embodiment, the first body component 200 and the second body component 202 may have substantially parallel walls that are configured to effectively form a sleeve that provides a passageway for the probe when the first body component 200 may be coupled to the second body component 202. In this embodiment, a first internal buttress component 207 and a second internal buttress component 209 may be supplied with the expansion material via different introductions of the expansion material. In other words, the first internal buttress component 207 and the second internal buttress component 209 may not be in fluid communication.

Similarly, a first external buttress component 211 and a second external buttress component 213 may be supplied with the expansion material via different introductions of the expansion material, because the first external buttress component 211 and the second external buttress component 213 may not be in fluid communication. In this embodiment with the first body component 200 and the second body component 202, it may not be convenient to have the buttress components in fluid communication. Of course, one or more of the various buttress components may be in fluid communication, which is not shown.

Figure 10:
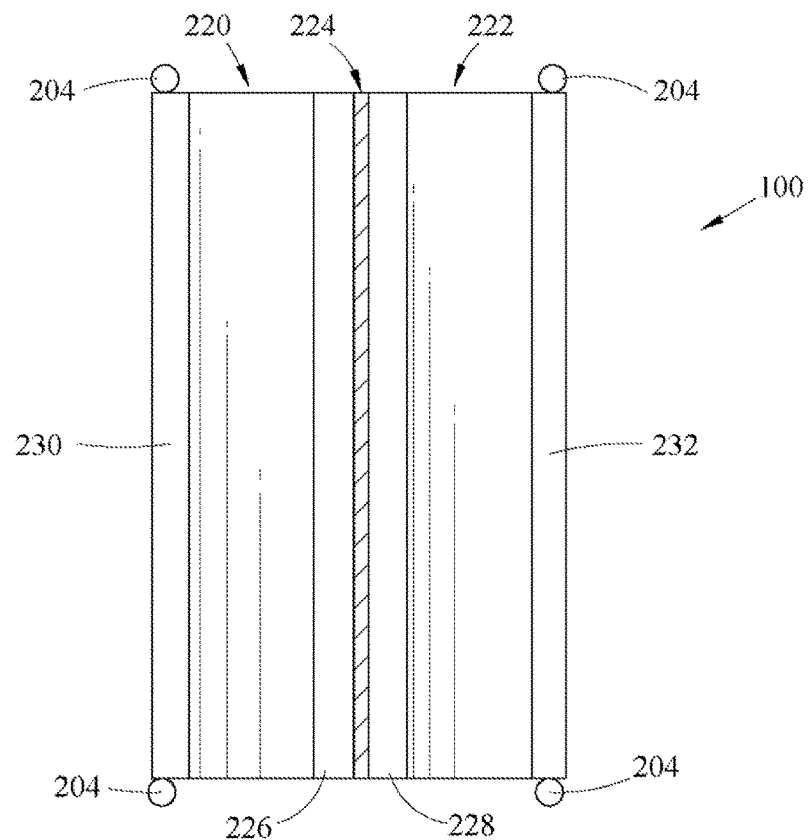
FIG. 10 shows in plan view a first body portion coupled to a second body portion via a hinge or pivot portion in accordance with various embodiments.

FIG. 10 shows another embodiment of the IRD 100. In this embodiment, a first body portion 220 is coupled to a second body portion 222 via a hinge portion 224 or flexible member at a first hinged side 226 of the first body portion 220 and a second hinged side 228 of the second body portion 222. The hinge portion 224 may be configured to allow the operator to take the IRD 100 from an open configuration as shown in FIG. 10 to the closed configuration, not shown, with one-handed operation. One or more pairs of fasteners 204 may couple a first open edge 230 of the first body portion 220 to a second open edge 232 of the second body portion 222. The fasteners 204 may extend beyond the first body portion 220 and the second body portion 222 as shown in FIG. 10 or be within the perimeter of the first body component 200 and the second body component 202 as shown in FIG. 9

In the configuration shown in FIG. 10, it may be convenient for the internal buttress, not shown, to be in fluid communication encircling the first body portion 220 and the second body portion 222, in other words substantially the entire body portion, as present in some of the other embodiments. Further, it may be convenient for the external buttress, not shown, to be in fluid communication substantially encircling the first body portion 220 and the second body portion 222, as present in some of the other embodiments. The internal buttress 108 and the external buttress 112 are not shown in FIG. 10 for simplicity and would be understood to be on a surface of the IRD 100 in back of the view shown.

Figure 11:
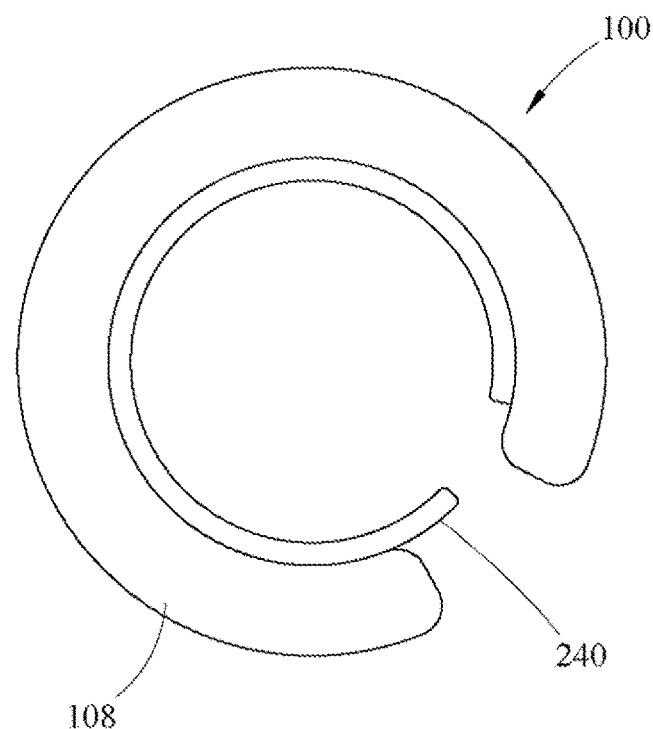
FIG. 11 shows in an end view an internal buttress coupled to a body portion in an open state that is biased to a closed state in accordance with various embodiments.
Figure 12:
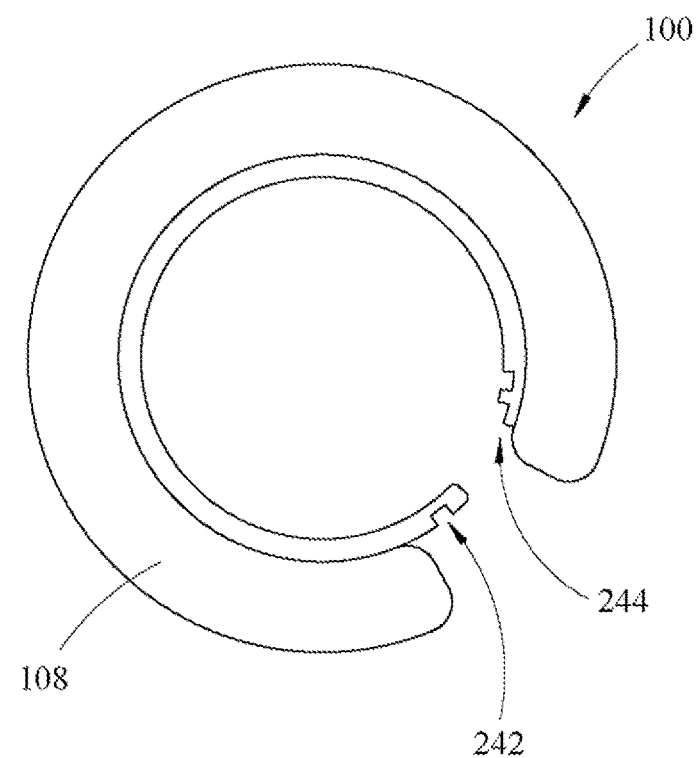
FIG. 12 shows in an end view an internal buttress coupled to a body portion in an open state that is biased to a closed state with fasteners on the body portion in accordance with various embodiments.

FIGS. 11-12 show a cross-section through the internal buttress 108 in another embodiment of the IRD 100. In these embodiments, the internal buttress 108 may be coupled to an internal buttress body portion 240 via laser welding, adhesive, or other suitable means. Or the internal buttress 108 may be of one material with the internal buttress body portion 240. The internal buttress body portion 240 may have a bias to a closed state to form the sleeve that is sized and dimensioned to fit around the probe that will be used by the operator. The internal buttress body portion 240 is shown in the open state in FIG. 11. The operator can position the IRD 100 around a probe when the internal buttress body portion 240 is in the open state when the IRD 100 is in the body cavity 104, the body aperture 106 or both, or when the IRD 100 is not in the body cavity 104, the body aperture 106 or both (see FIG. 1). Further, FIG. 12 shows the internal buttress body portion 240 with a first fastener 242 and a second fastener 244. The first fastener 242 is configured to be coupled to the second fastener 244 to form the sleeve that is sized and dimensioned to fit around a probe.

In addition, the internal buttress 108 may overlap the body portion 240 as shown to help form an effective seal for retention of the insufflation material. Alternatively, the internal buttress 108 may not overlap the internal buttress body portion 240, as not shown, and still achieve an effective seal for retention of the insufflation material.

Similarly, the external buttress may overlap or not overlap an analogous external buttress body portion to form an effective seal for retention of the insufflation material, which is not shown.

Figure 13:
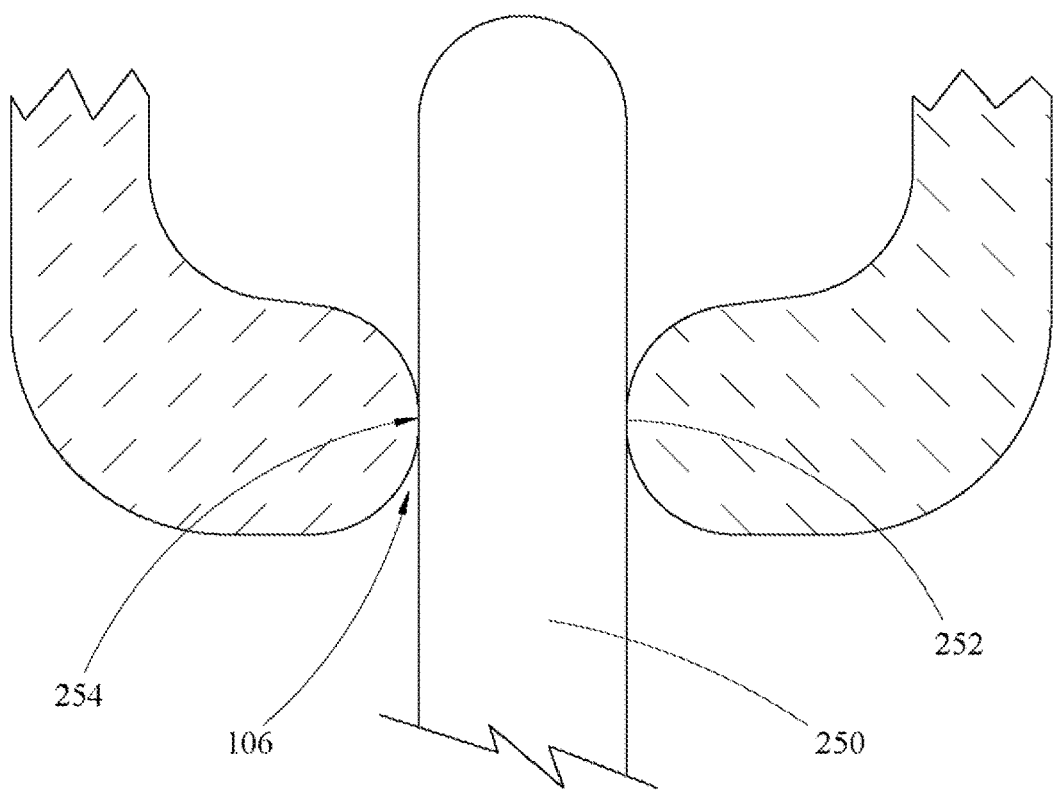
FIG. 13 shows in partial cross-section view a probe through a body aperture in accordance with various embodiments.
Figure 14:
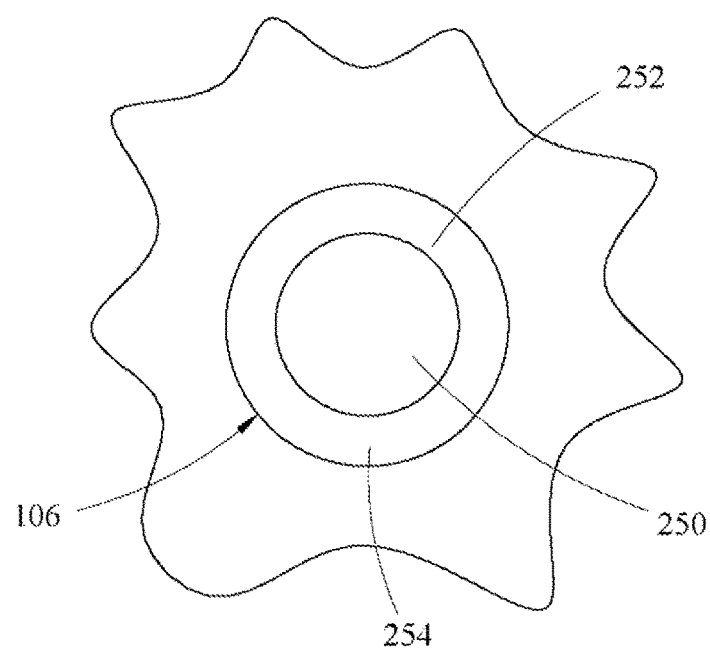
FIG. 14 shows in end view a probe through a body aperture in accordance with various embodiments.

FIG. 13 shows in a cross-sectional side view and FIG. 14 shows in an end view a probe 250 through the body aperture 106. The body aperture 106 effectively forms a body probe seal 252 with the probe 250 that has been inserted through the body aperture 106. Furthermore, a layer of lubricant 254 is typically lathered on the probe 250 before entry through the body aperture 106. The layer of lubricant 254 disposed between the body aperture 106 and the probe 250 further aids forming the body probe seal 252 between the body aperture 106 and the probe 250. The layer of lubricant 254 may be of any suitable type to reduce friction between the body aperture 106 and the probe 250

Figure 15:
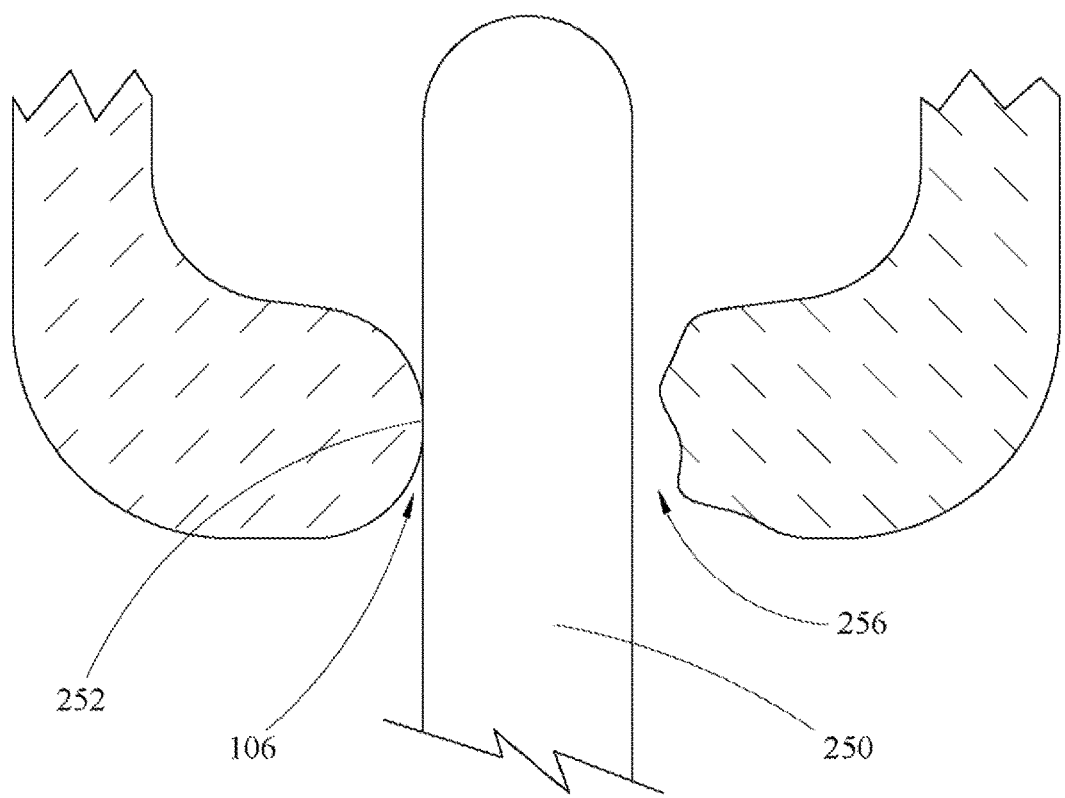
FIG. 15 shows in partial cross-section view a probe through a body aperture with an abnormality.
Figure 16:
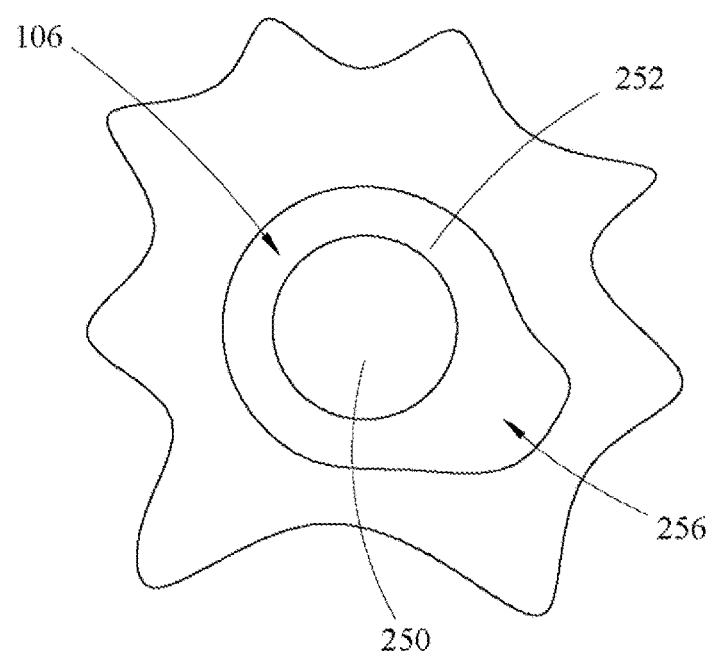
FIG. 16 shows in end view a probe through a body aperture with an abnormality.

FIG. 15 shows in a cross-sectional side view and FIG. 16 shows in an end view the probe 250 through the body aperture 106 with an abnormality 256. The body aperture 106 cannot effectively form the body probe seal 252 with the probe 250 that has been inserted through the body aperture 106 with the abnormality 256. For whatever reason, such as congenital malformation, abscess, previous abscess, muscle laxity, etc., the body aperture 106 does not effectively form the body probe seal 252 with the probe 250 through the body aperture 106.

Figure 17:
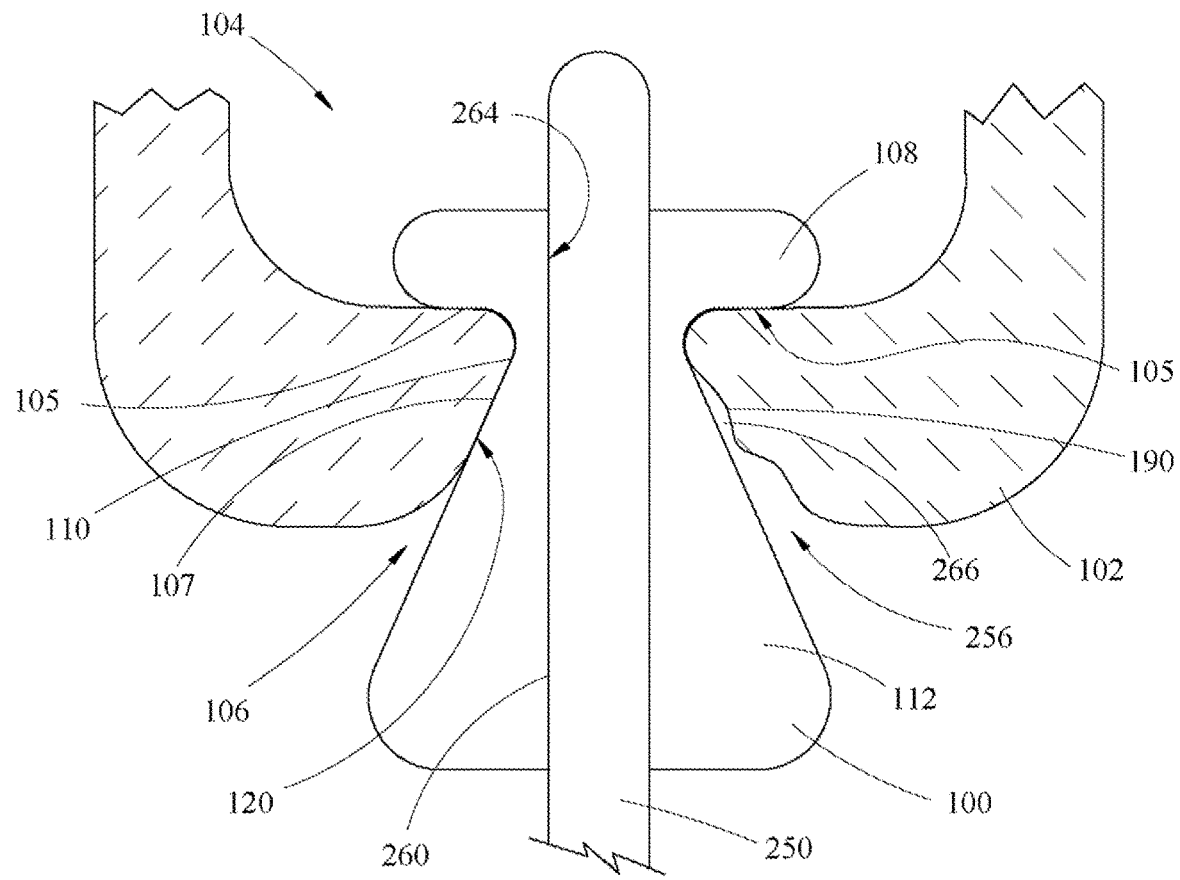
FIG. 17 shows in partial cross-section view a probe through a body aperture with an abnormality with the probe through an insufflation retention device in accordance with various embodiments.
Figure 18:
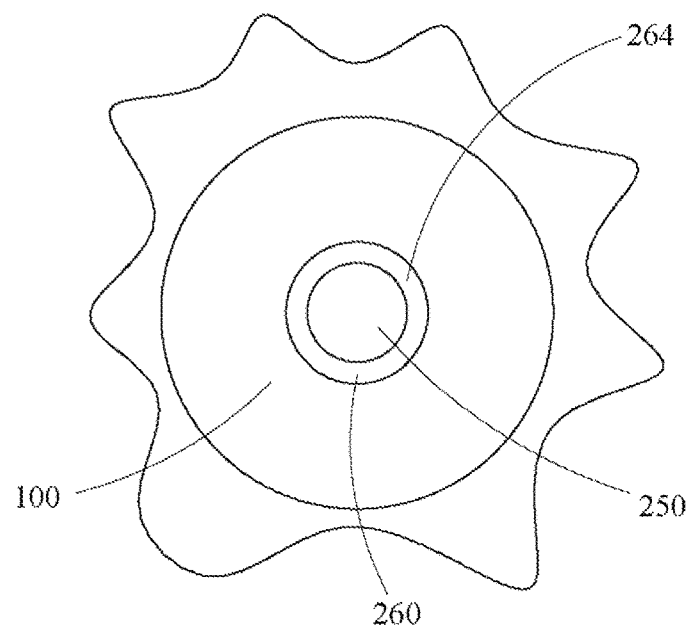
FIG. 18 shows in end view a probe through a body aperture within an abnormality with the probe through an insufflation retention device in accordance with various embodiments.
Figure 19:
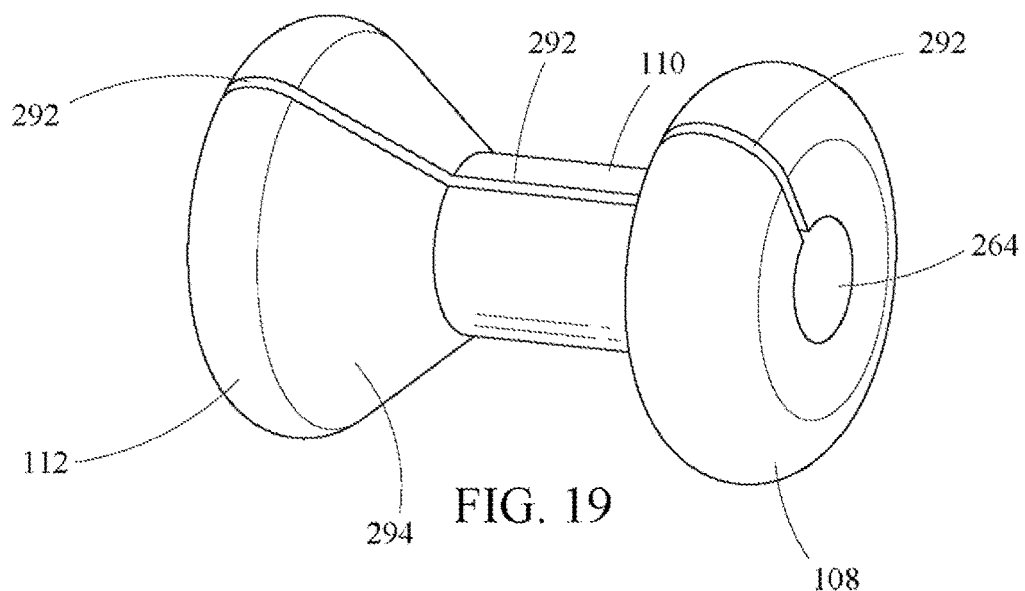
FIG. 19 shows in perspective view an insufflation retention device in accordance with various embodiments.
Figure 20:
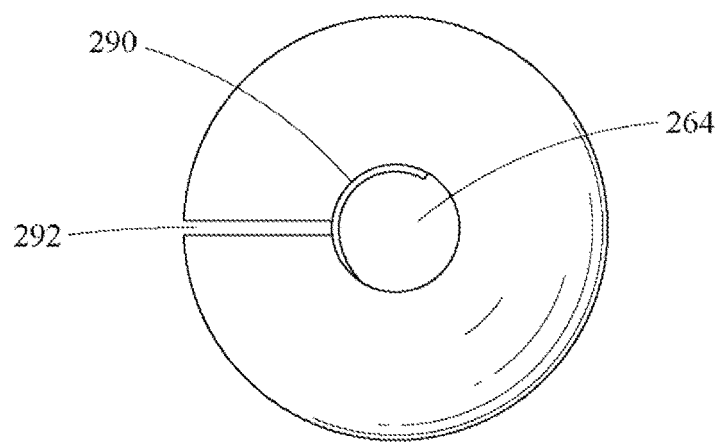
FIG. 20 shows in end view the insufflation retention device of FIG. 19 in accordance with various embodiments.
Figure 21:
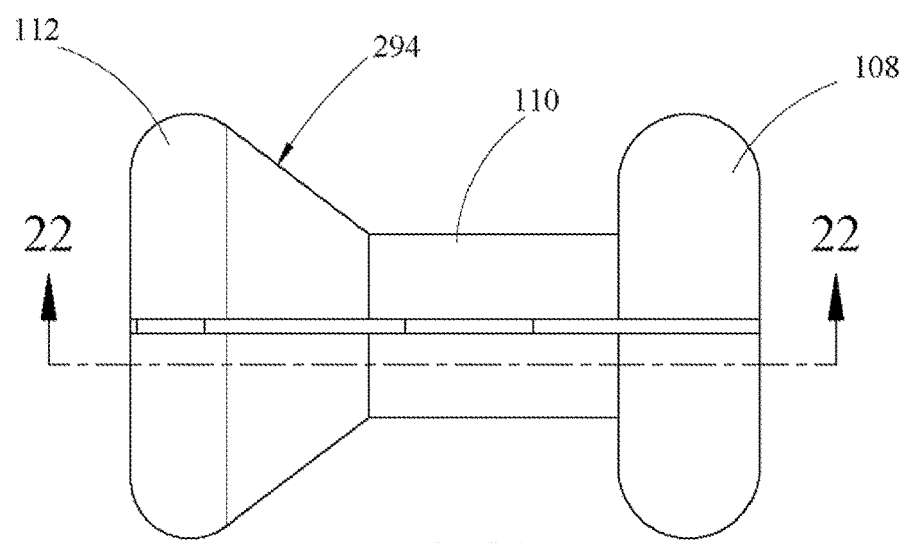
FIG. 21 shows in side view the insufflation retention device of FIG. 19 in accordance with various embodiments.
Figure 22:
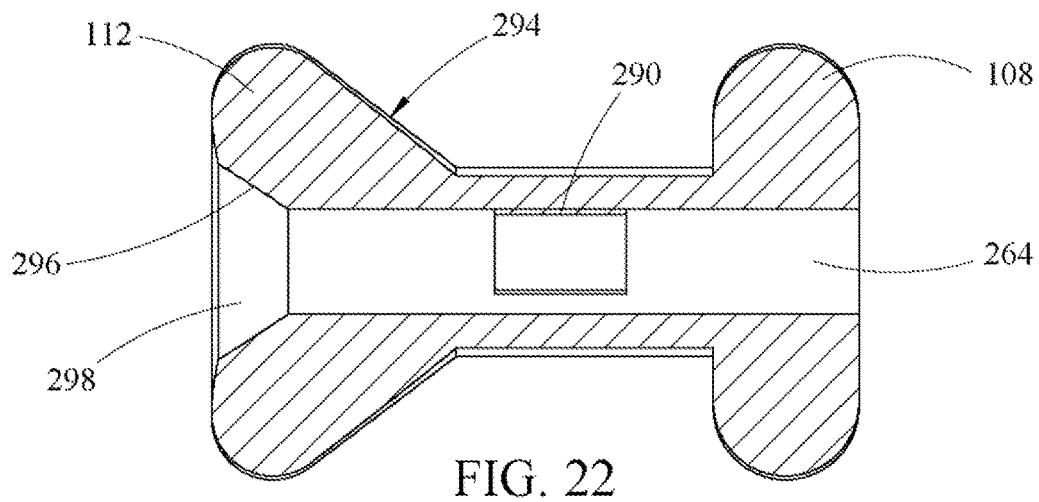
FIG. 22 shows in cross-section view the insufflation retention device of FIG. 22 in accordance with various embodiments.
Figure 23:
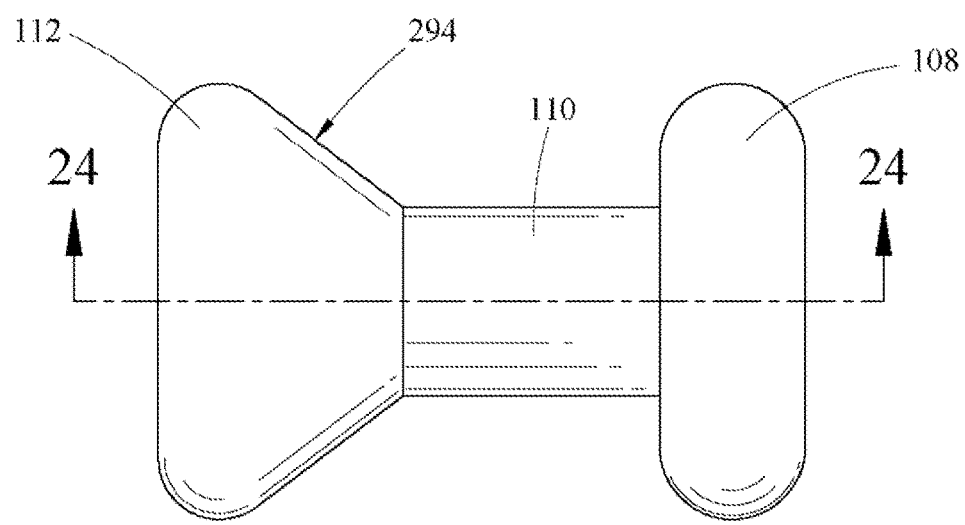
FIG. 23 shows in side view opposing side of the side of the insufflation device of FIG. 21 in accordance with various embodiments.
Figure 24:
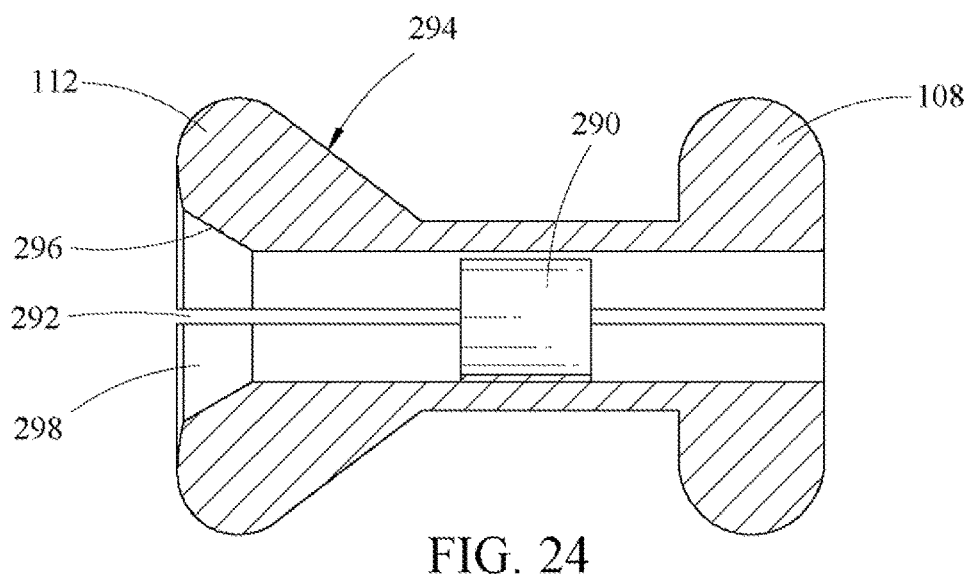
FIG. 24 shows in cross-section view the insufflation retention device of FIG. 23 in accordance with various embodiments.
Figure 25:
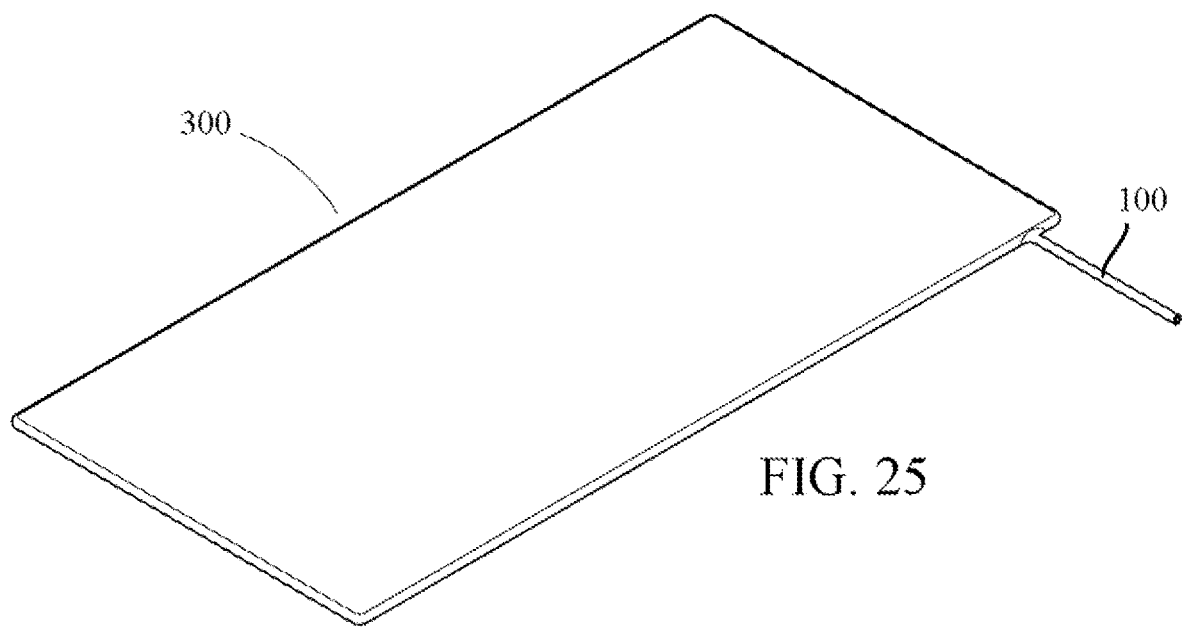
FIG. 25 shows perspective view of a passageway structure used in an insufflation retention device in accordance with various embodiments.
Figure 26:
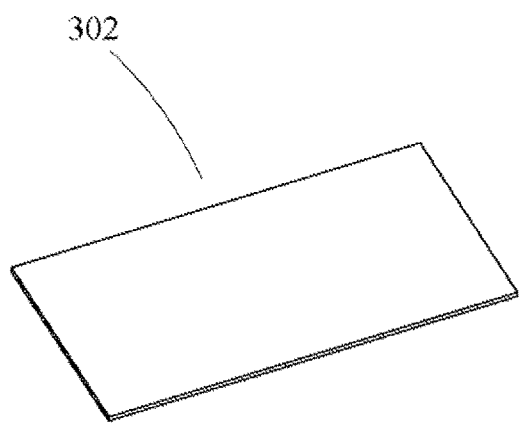
FIG. 26 shows a perspective view of an external compression member in an open state, wherein the external compression member is used in conjunction with the insufflation retention device of FIG. 25.

FIG. 17 shows in a cross-sectional side view and FIG. 18 shows in an end view a probe 250 through the body aperture 106 with the abnormality 256, and the probe 250 through the IRD 100 in accordance with various embodiments. Analogous to framing a window in a house, the IRD 100 can effectively form a seal with the body 102 to promote retention of the insufflation material in the body cavity 104. Furthermore, the IRD 100 can provide a sleeve of predetermined configuration and size responsive to the probe to effectively form another seal with the probe to further promote retention of the insufflation material in the body cavity 104.

Of course, the IRD 100 can be used with the probe 250 in the body aperture 106 without the presence of the abnormality 256. However, when the IRD 100 is used with the probe 250 in the body aperture 106 with the abnormality 256, the IRD 100 is configured to promote retention of the insufflation material inserted into the body cavity 104 for a time effective for operator performance of the diagnostic intervention, the therapeutic intervention, or both that is better than retention of the insufflation material could be achieved using the probe 250 without the IRD 100. A probe passageway seal 260, the body midportion seal 109, the body external buttress seal 107, and the body internal buttress seal 105 may be configured to cooperate with the probe 250 to promote retention of the insufflation material inserted into the body cavity 104 for a time effective for operator performance of the diagnostic intervention, the therapeutic intervention, or both. On the other hand, the passageway 264 may be open without the probe 250 present in the passageway 264, such that the insufflation material may not be not retained in the body cavity 104. FIG. 17 shows that the passageway 264 may be open without the probe 250 present in the passageway 264 even when the internal buttress 108 is expanded and the external buttress 112 is expanded.

The IRD 100 can effectively form seals, the body midportion seal 109 between the midportion 110 and the wall 120 of the body aperture 106, the body external buttress seal 107 between the external buttress 112 and the wall 120 of the body aperture 106 and exterior to the body aperture 106, and the body internal buttress seal 105 between the internal buttress 108 and the body cavity 104 or the body 102, even in the presence of the abnormality 256. As shown in FIG. 17, the midportion 110 may blend or be operationally contiguous with the external buttress 112 to both function to inhibit advancement of the IRD 100 into the body cavity 104 during operation.

Further, the IRD 100 can effectively form the probe passageway seal 260 when the probe 250 is inserted in the IRD 100. A passageway 264 through the midportion 110 of the IRD 100 may be configured to form the probe passageway seal 260 between the probe 250 and the passageway 264. The passageway 264 extends past the first end 174 and past the second end 176 (see FIG. 5 and FIG. 6) of the IRD 100, so that the probe 250 extends all the way through the IRD 100. One skilled in the art would understand that the passageway 264 has a corresponding first opening near the first end 174 and a second opening near the second end 176 for the probe 250.

In addition, the external surface 190 of the midportion 110 may be configured to provide a contour feature 266 to engage the abnormality 256 to provide an effective seal. Of course, the contour feature 266 may be a protrusion, indentation, or combination of both to engage the abnormality 256 to provide an effective seal. Further, the contour feature 266 may be formed from the external buttress 112 or both the midportion 110 and the external buttress 112. In addition, the internal buttress 108 may have a contour feature, as discussed previously shapes are contemplated depending on the need of the operator in view of the body 102 of a patient.

FIGS. 19-24 show various views of the IRD 100 in accordance with another embodiment. The IRD 100 may have the internal buttress 108 and the external buttress 112 with the midportion 110 therebetween. The IRD 100 may be made with a seam 292 that runs the length of the IRD 100 as shown, or a portion thereof. The seam 292 essentially may be a gap or split between surfaces of the material that is folded on itself to make the IRD 100. The seam 292 may not be present if the surfaces of the material that is folded on itself to make the IRD 100 abut each other. The external buttress 112 has a tapered surface 294 that is substantially conical to facilitate an effective seal with the body 102 (see FIG. 1).

An internal bias member 290 with biasing tension cooperates with a biasing tension of the rest of the IRD 100 to keep the IRD 100 closed during operation. The internal bias member 290 may be substantially flush with an interior of the IRD 100, or the internal bias member 290 may be substantially not flush with the interior of the IRD 100. On the other hand, the IRD 100 shown may be opened to wraparound the probe 250 when the probe 250 is in the body aperture 106, the body cavity 104, or both, and then the IRD may be inserted into and through the body aperture 106. The internal bias member 290 is configured for one-handed or two-handed operation.

An entry port 298 in the external buttress 112 may be configured to have a diameter wider than a diameter of the passageway 264, wherein the diameters are substantially parallel to each other. By having the diameter of the entry port 298 wider than the diameter of the passageway 264, the operator will have a larger target for insertion of the probe 250 into the passageway 264 then if the diameter of the entry port 298 was substantially the same size as the diameter of the passageway 264. The diameter of the passageway 264 may be configured and sized to fit closely around a diameter of the probe 250, so that the probe passageway seal between the passageway and the probe can be more easily achieved, and wherein again these diameters are substantially parallel to each other. There may be an internal taper 296 in the external buttress 112 so that the diameter of the entry port 298 can taper down to the smaller diameter of the passageway 264. While the internal taper 296 is shown as substantially linear resulting in a conical structure in FIG. 22, any suitable shape to facilitate the operator maneuvering the probe 250 into the passageway 264 is contemplated.

This embodiment is shown as a solid structure, which the IRD 100 may be if the internal buttress 108 is of a compressible material (e.g., foam by way of example and limitation), such that the internal buttress 108 may be pushed through the body aperture 106 in the contracted state and then once inside the body cavity 104, the internal buttress 108 may expand into the expanded state. Of course, this similar structure, such as with the entry port 298 having the internal taper 296, may be present in conjunction with features from the other embodiments that include the internal buttress 108 that is expandable by the expansion material.

FIGS. 25-29 show various views of the IRD 100 in accordance with another embodiment. The internal buttress 108 and the external buttress 112 may be in fluid communication through the midportion 110, not shown, via what is effectively a rectangular balloon, also known herein as a passageway structure 300. The midportion 110 may be compressed by an external compression member 302 that essentially biases fluid within the passageway structure 300 towards the internal buttress 108 and the external buttress 112. The external compression member 302 may be contactingly adjacent an external surface of the passageway structure 300. The external compression member 302 in a closed position may or may not force substantially all the fluid, i.e., expansion material, from the midportion 110 in the IRD 100 that is ready for use by the operator. While the passageway structure 300 is indeed shown and conceived of as rectangular and in operation to be symmetrical, other appropriate sizes and dimensions are contemplated based on needs of the user in view of the body 102 of the patient.

Figure 27:
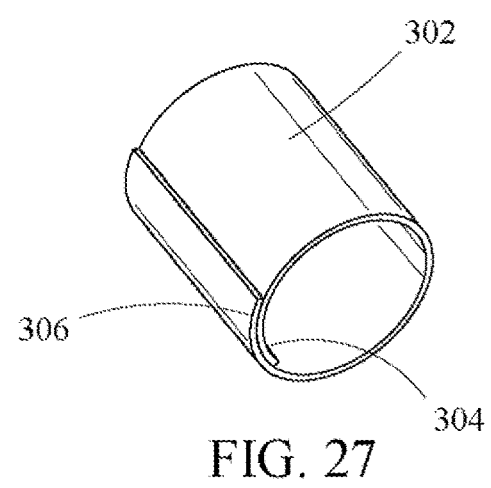
FIG. 27 shows a perspective view of the external compression member in a closed state used in conjunction with the insufflation retention device of FIG. 25.
Figure 28:
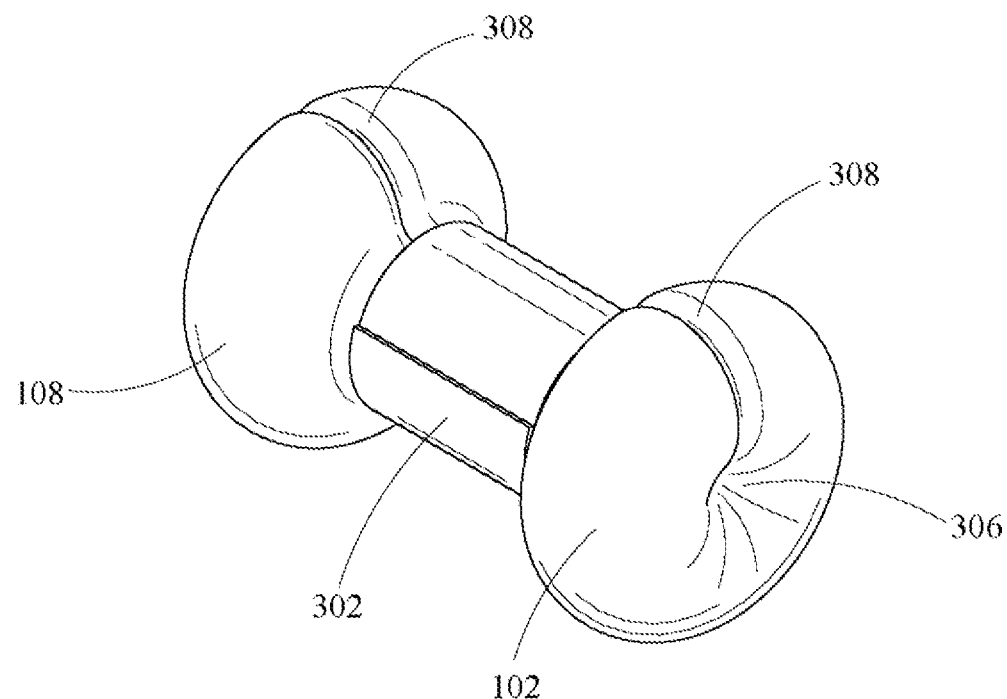
FIG. 28 shows a perspective view of the insufflation retention device of FIG. 25 in accordance with various embodiments.
Figure 29:
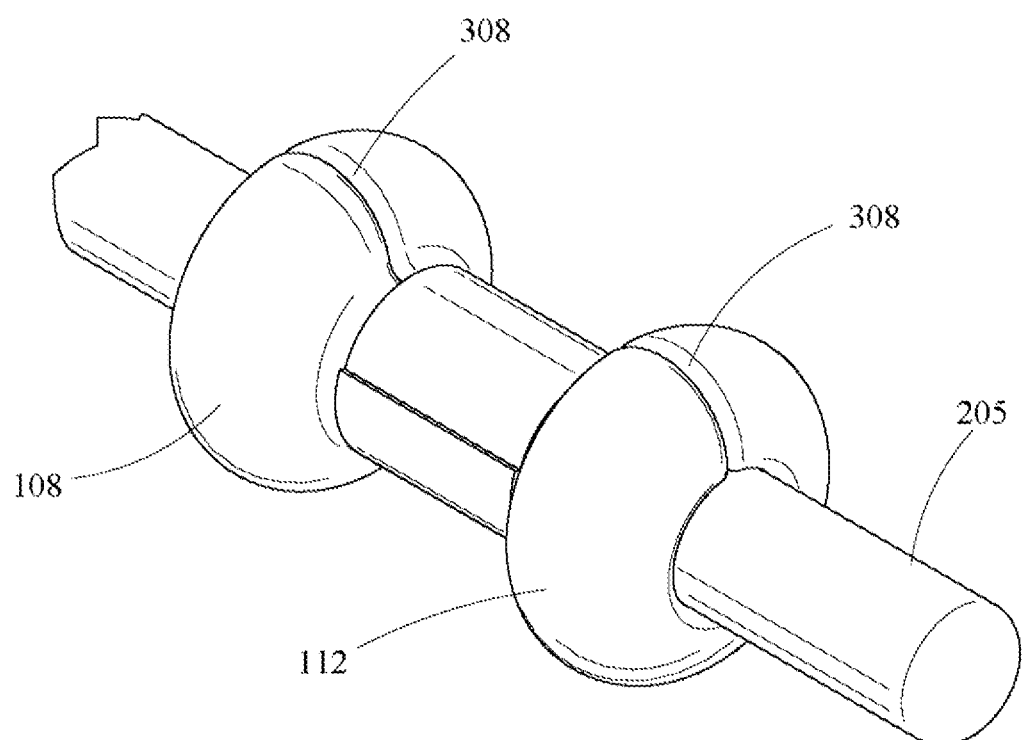
FIG. 29 shows a perspective view of the insufflation retention device of FIG. 25 with a probe through the passageway in accordance with various embodiments.

The external compression member 302 may have an internal bias member 304 that in the rolled configuration is internal to an external bias member 306 of the external compression member 302 in the closed position shown in FIGS. 27-29. Furthermore, while the external compression member 302 is shown to have an overlap with an external bias member 306 overlapping the internal bias member 304, the external compression member 302 may not overlap itself, just as the internal bias member 304 may not overlap itself. The external compression member 302 is configured for one-handed or two-handed operation from an open position, wherein the IRD 100 with the external compression member 302 in the open position may be positioned to encircle the probe 250 and in the closed position may be maintained around the probe 250.

While the external compression member 302 is shown external to the balloon that forms the internal buttress 108, the external buttress 112, and a portion of the midportion 110, it is fully contemplated that the external compression member 302 may be internal to the passageway structure 300.

Figure 30:
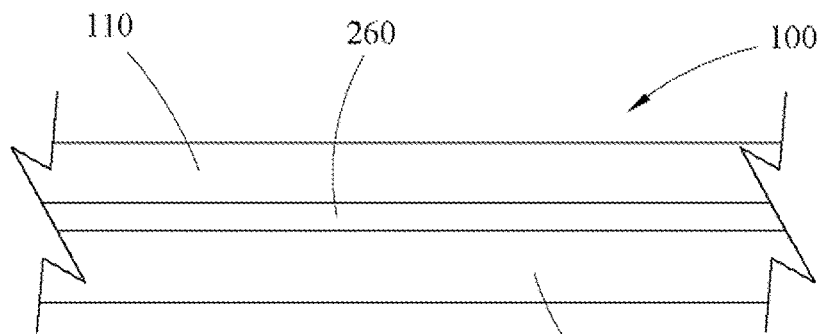
FIG. 30 shows in partial cross-section view an insufflation retention device with a probe in accordance with various embodiments.
Figure 31:
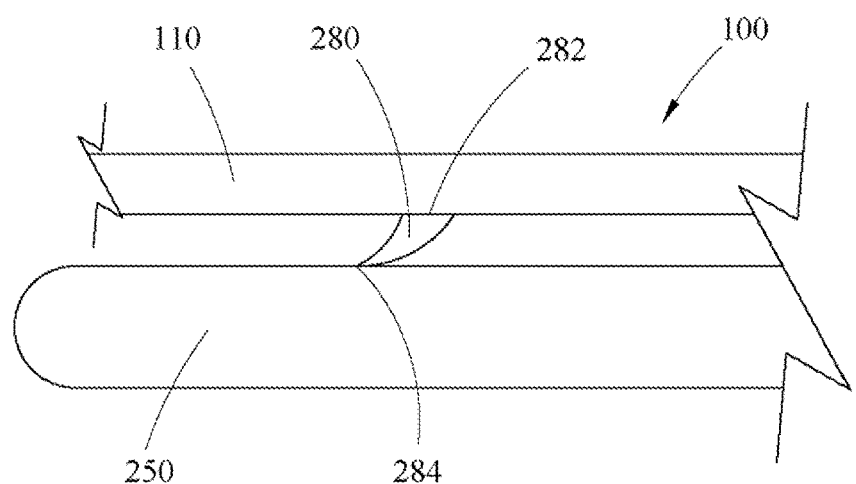
FIG. 31 shows in partial cross-section view an insufflation retention device with an O-ring type structure with a probe in accordance with various embodiments.
Figure 32:
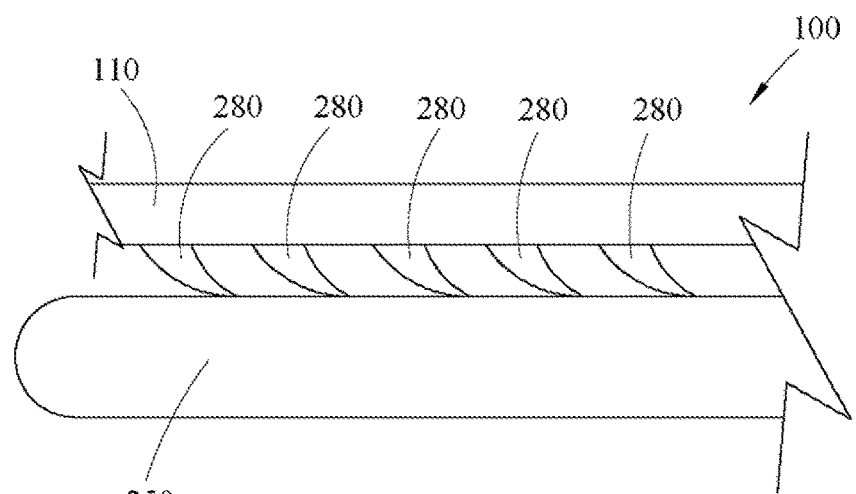
FIG. 32 shows in partial cross-section view an insufflation retention device with a plurality of O-ring type structures with a probe in accordance with various embodiments.

FIGS. 30-32 show cutaway side views of the IRD 100 with an O-ring type structure 280 or a plurality of O-ring type structure 280 in accordance with various embodiments. The IRD 100 may cooperate with the probe 250 to form the probe passageway seal 260 that is an effective seal between the IRD 100 and the probe 250. Further, the layer of lubricant 254 between the IRD 100 and the probe 250 may aid in or promote the effectiveness of the probe passageway seal 260 between the IRD 100 and the probe 250.

Further, the O-ring type structure 280 along the sleeve may further aid in promoting the seal between the IRD 100, e.g., the midportion 110, and the probe 250. The O-ring type structure 280 may be fixed to the sleeve at a first O-ring end 282 and mobile at an opposing, second O-ring end 284. The O-ring type structure 280 may be one of a plurality of O-ring type structures 280. While the O-ring type structure 280 may be rigid, there may be benefit in having the O-ring type structure 280 be flexible such that the opposing, second O-ring end 284 is dragged internally towards the body cavity 104 when the probe 250 is advanced and the opposing, second O-ring end 284 is dragged externally away from the body cavity 104 when the probe 250 is retracted.

As discussed in the various embodiments, when the probe is in the body aperture 106 or the body cavity 104, the operator may not be able to insert the probe into and through the IRD 100 or slide the IRD 100 over the probe. On the other hand, in other embodiments, the operator may able to couple the IRD 100 around the probe that remains in position in the body aperture 106 or in both the body aperture 106 and the body cavity 104.

One skilled in the art would understand that the probe may be an endoscope, by way of example and not limitation. A commercially available endoscope would have a light source configured to provide light in the lumen of a colon, such as body cavity 104, and an integrated air pump configured to provide air in the lumen of the colon for luminal expansion at colonoscopy. Furthermore, one skilled in the art would understand that the endoscope could be configured to use $CO_2$, water, or other suitable materials for insufflation of the lumen of the colon.

For colonoscopy, one skilled in the art would understand that bowel preparation quality may impact the success of colonoscopy. Many bowel preparation agents are available to accomplish adequate bowel cleanliness. E.g., *Optimizing bowel preparation for colonoscopy: a guide to enhance quality of visualization*, Ann Gastroenterol 2016; 29 (2): 137-146, which is incorporated by reference in its entirety.

Figure 33:
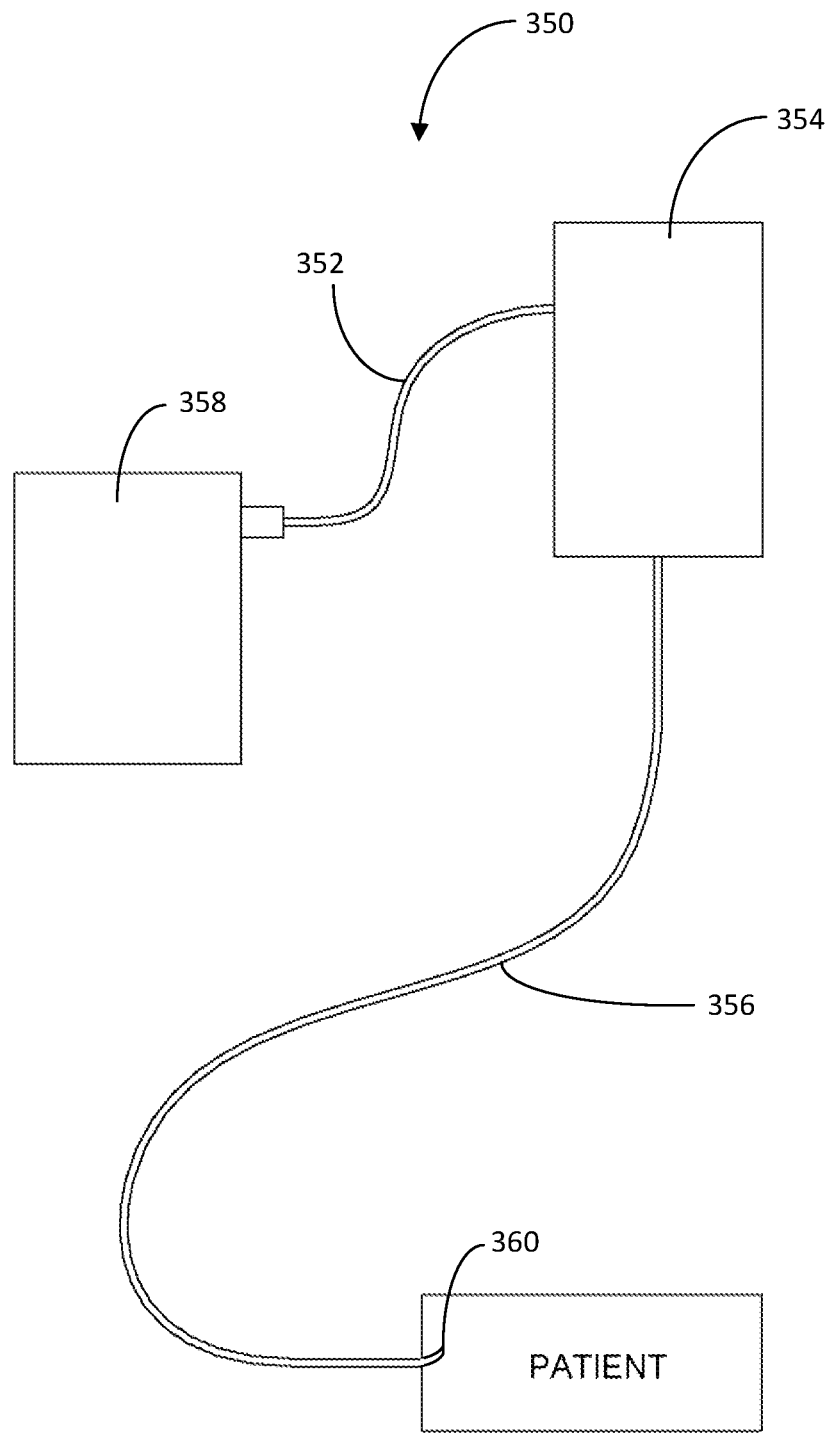
FIG. 33 shows a probe that may be used with and insufflation retention device in accordance with various embodiments.

In addition, FIG. 33 shows a commercially available endoscope 350 as understood by one skilled in the art. The commercially available endoscope 350 has three main parts: a connector section 352, a control section 354, and an insertion tube 356. The connector section 352 attaches the endoscope 350 to systems 358 that may include a display, an image processor, light and electrical sources, and sources of water, air, $CO_2$ or other suitable materials. The control section 354 is attached to the connector section 352. The control section 354 is held by an operator to control dials that may deflect a tip 360 of the insertion tube 356 instrument tip up/down and left/right. The control section 354 may have separate buttons for suction, insufflation, and imaging. Finally, the control section 354 may have an entry port for inserting accessories through a channel of the insertion tube 356 into the body cavity 104. Many endoscopes also have additional controls. The insertion tube 356 is a flexible shaft attached to the control section 354. The insertion tube 356 may contain one of more channels for accessories, flushing water, insufflation, etc. The insertion tube 356 may include angulation actuators for deflection of the tip 360 of the insertion tube 356. The tip 360 of the insertion tube 356 may contain an image generation device, an illumination system, an opening for insufflation, an objective lens, and a water jet to clear the lens. The length, diameter, and flexibility of the insertion tube 356 vary among endoscope types and manufacturers, with diameter in the range of about 4.9 mm to about 12.9 mm. E.g., see *Report on Emerging Technology: GI Endoscopes*, Gastrointestinal Endoscopy, Volume 74, No. 1, 2011, pages 1-6, which is incorporated by reference in its entirety.

Therefore, one would understand that while the probe 250 could be inserted in the IRD 100 of all embodiments when the IRD 100 is out of the body cavity 104 or the body aperture 106, the probe 250 could be inserted in the IRD 100 in only some embodiments when the IRD 100 is in the body cavity 104 or the body aperture 106. See for example FIG. 1 wherein the internal buttress 108 is configured to be continuous around the probe 250, such that the internal buttress 108 is configured to have only a closed state. The probe 250 may only be inserted in the internal buttress 108 that is continuous when the IRD 100 is out of the body cavity 104 or the body aperture 106. On the other hand, see example FIG. 11 wherein the internal buttress 108 is configured to be discontinuous around the probe 250, such that the internal buttress 108 is configured to have the closed state and an open state. When the internal buttress 108 is discontinuous, the operator can position the IRD 100 around the probe when the internal buttress 108 is in the open state when the IRD 100 is in the body cavity 104, the body aperture 106 or both, or when the IRD 100 is not in the body cavity 104, the body aperture 106 or both.

Figure 34:
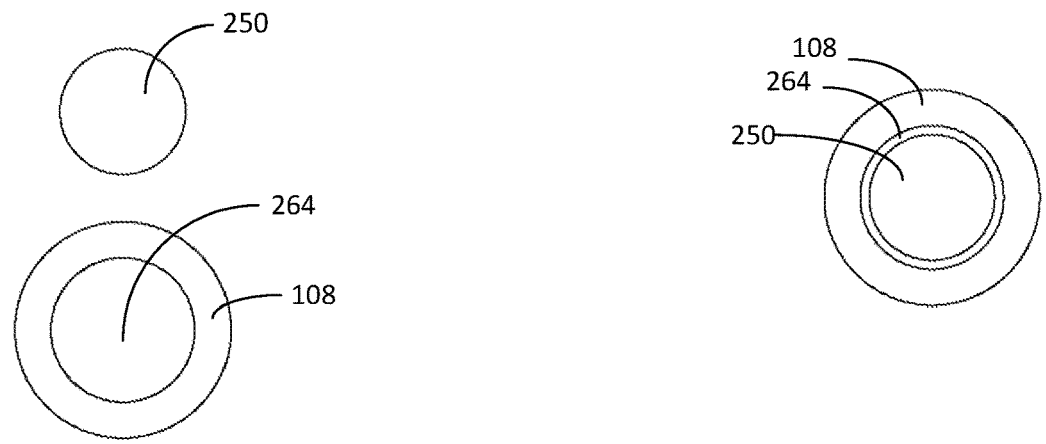
FIGS. 34 (A)-(C) show continuous internal buttress having only the closed state and discontinuous internal buttress having both the open state and the closed state in accordance with various embodiments
Figure 34:
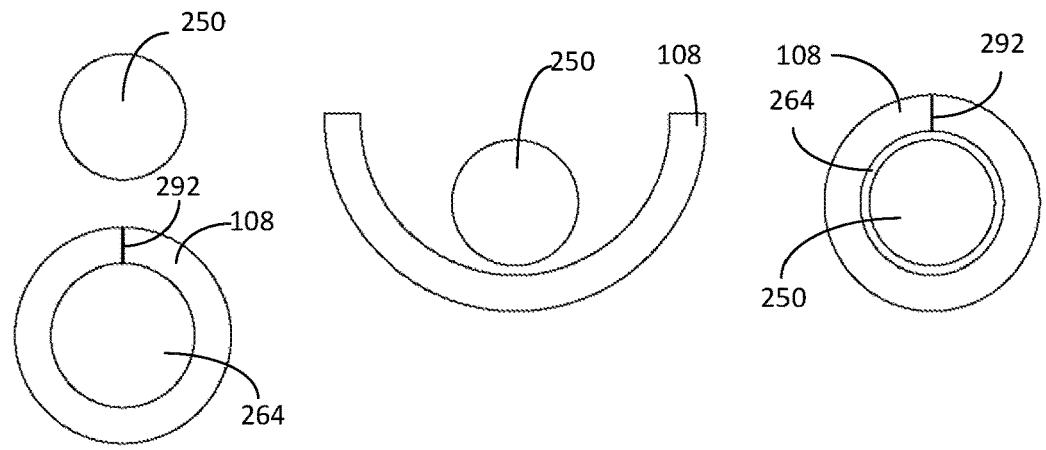
Figure 34:
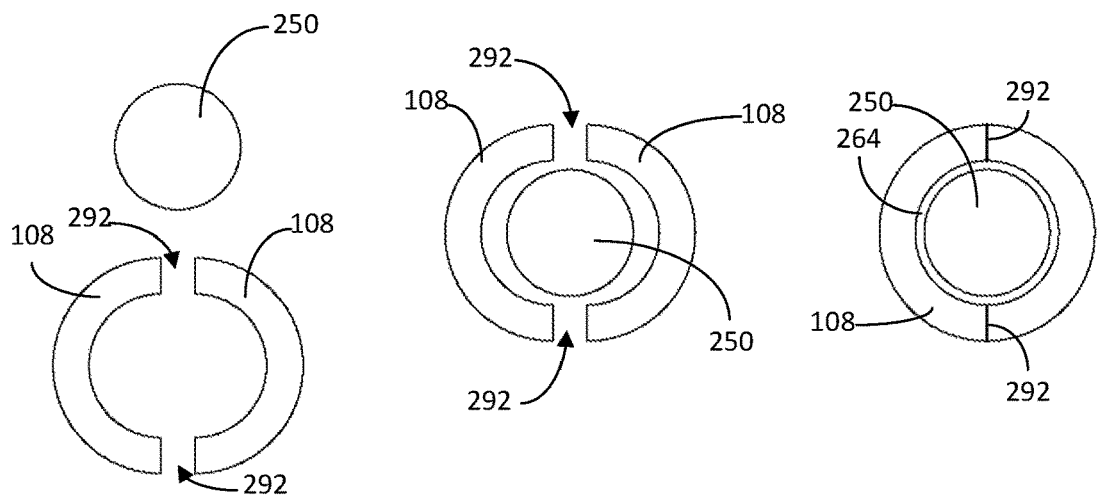

FIG. 34 shows in end views what one skilled in the art would understand is the relationship between embodiments showing a continuous structure of the internal buttress 108 around the probe and a discontinuous structure of the internal buttress 108 around the probe 250. While the probe 250 is shown as substantially a cylinder and the internal buttress 108 is shown as a ring, other shapes (e.g., oval, etc.) are contemplated and disclosed throughout this specification.

FIG. 34 (A) shows the probe 250 outside a continuous structure of the internal buttress 108. In the continuous structure of the internal buttress 108, the only way for the internal buttress 108 to be positioned around the probe 250 as shown in the top right diagram is for the internal buttress 108 to be slid relative to the probe 250 such that the probe 250 comes to located within the internal buttress 108 and be surrounded by the internal buttress 108. The probe 250 would be passing through the passageway 264 in this situation. The internal buttress 108 may not be able to slide on to the probe 250 when the probe 250 is in the body aperture 106 or the body cavity 104 when the internal buttress 108 has a continuous structure. E.g., the probe may have only one end that can slide into internal buttress 108, such as when the probe is a colonoscope. In such an example, the colonoscope 350 has an insertion tube 356 that may be configured to slide on to the probe 250. However, at a first end of the insertion tube 356 there may be the control section 354, the connector section 352, and the systems 358 that would prevent the insertion tube 356 sliding on to the internal buttress 108 at the first end. The colonoscope 350 has the tip 360 at the second end of the insertion tube 356 that is configured to slide into the internal buttress 108. However, when the tip 360 is in the body aperture 106 or the body cavity 104, then the tip 360 is unavailable the slide into the internal buttress 108.

FIG. 34 (B) shows from left to right, the probe 250 outside of the one-piece construction of the internal buttress 108 that is biased to the closed position, the probe 250 within the internal buttress 108 that is in the open state, and the probe 250 located within the internal buttress 108 and surrounded by the internal buttress 108 that is in the closed state. There may be challenges in manufacturing the IRD 100 as one semirigid piece with the seam 292 along the length of the side of the IRD 100 to facilitate sliding the IRD 100 over the probe after the probe is in the body aperture 106, the body cavity 104, or both. For that reason, it may be necessary to have brackets 656 or other fasteners to more closely approximate the edges of the seam 292 so that the IRD 100 may promote retention of the insufflation retention material, as discussed elsewhere.

FIG. 34 (C) from left to right, the probe 250 outside of the two-piece construction of the internal buttress 108, the probe 250 within the internal buttress 108 that is in the open state, and the probe 250 located within the internal buttress 108 and surrounded by the internal buttress 108 that is in the closed state. The two-piece construction has two seams 292.

Figure 35:
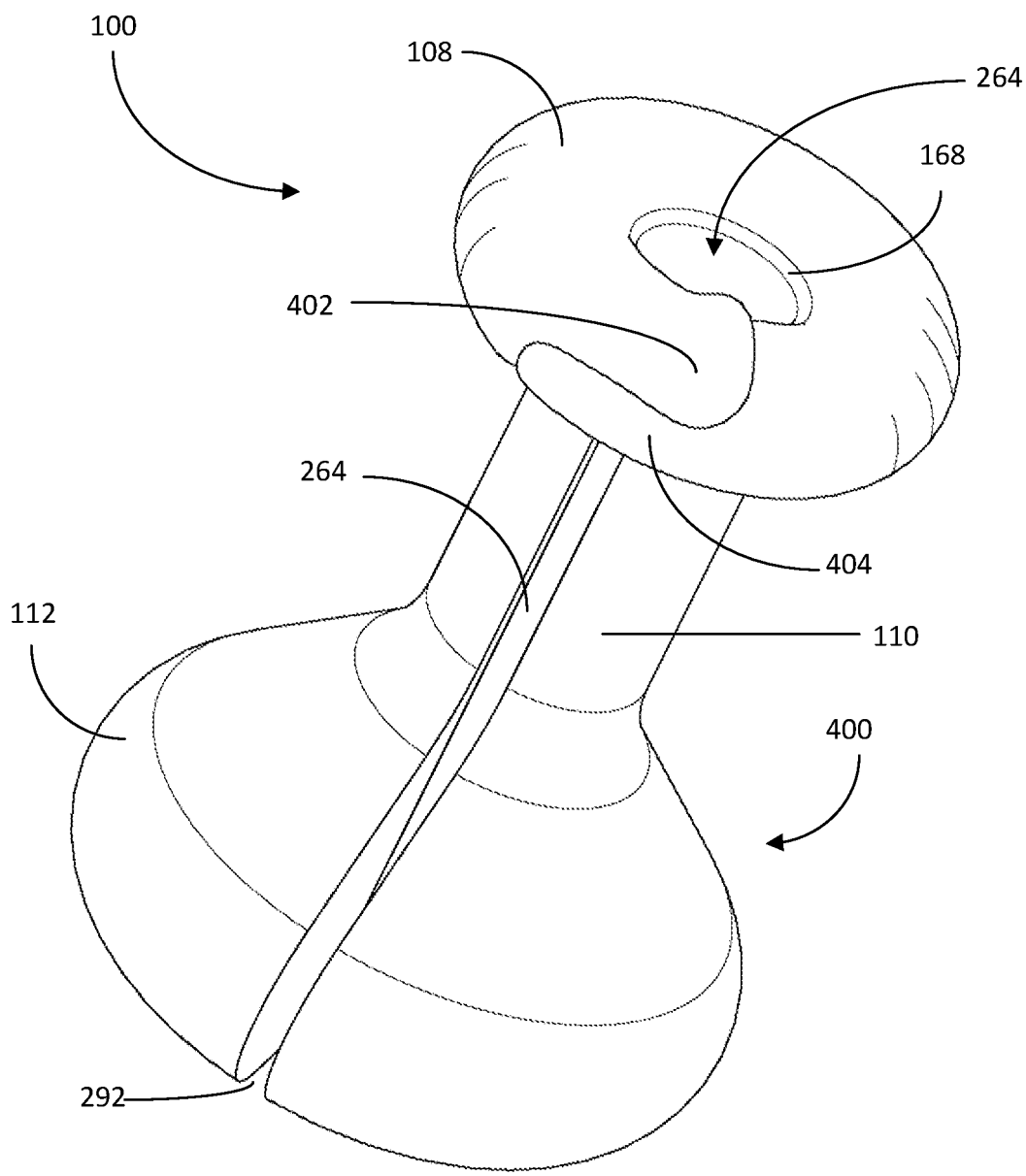
FIG. 35 shows in perspective view an insufflation retention device in accordance with various embodiments.

FIG. 35 shows a perspective view of another embodiment of the IRD 100. The external buttress 112, the midportion 110, and the internal buttress portion 168 may be formed of one piece as shown. Alternatively, the external buttress 112, the midportion 110, and the internal buttress portion 168 may be formed of two or more pieces, as shown in other embodiments. The combined external buttress 112, the midportion 110, and the internal buttress portion 168 may be known herein as a handle or a base member 400.

The internal buttress 108 may be affixed to the base member 400 by heat staking/welding, laser welding, induction bonding, RF welding, impulse sealing, adhesive or other suitable methodology. The balloons could be formed with various processes as well: dip molding, thermoforming, welding extruded film or other suitable methodology. The base member 400 could be formed via injection molding, compression molding, transfer molding, liquid-silicone-rubber molding or other suitable methodology. All materials are biocompatible.

The base member 400 may be semirigid with rigidity greater than the internal buttress in the expanded state. The internal buttress may be a balloon with an unexpanded state and as shown an expanded state. The balloon may be configured to interlock and snap closed upon itself in the expanded state. The balloon may be thermoformed in such a way that as the balloon inflates from the unexpanded state to the expanded state, a first end 402 of the internal buttress 108 locks together with a second end 404 of the internal buttress 108 to create a seal between the two ends of the balloon portion of the internal buttress 108. In so doing, the balloon in the expanded state forms the internal buttress 108 that creates an effective seal for retention of the insufflation material.

In the unexpanded state, the internal buttress has an open state. In the expanded state, the internal buttress 108 has a closed state. In the unexpanded state of the internal buttress 108, the base member 400 may have an open state with the seam 292 along the entire length of the base member 400. In the expanded state of the internal buttress 108, the base member 400 may have a closed state. In the open state of the internal buttress 108 and the base member 400, the IRD 100 may be placed around the probe when the probe is in the body cavity, the body aperture, or both the body cavity and the body aperture, because the seam 292 is substantially open. In the closed state of the internal buttress 108 and the base member 400, the IRD 100 may not be placed around the probe when the probe is in the body cavity, the body aperture, or both the body cavity and the body aperture, because the seam 292 is substantially closed. However, in the closed state of the internal buttress 108 and the base member 400, the IRD 100 may slide the IRD 100 over the probe when the probe is not in the body cavity, the body aperture, or both the body cavity and the body aperture, because the passageway 264 for the probe is open so that insufflation material is not retained when the probe is not present.

As shown, the internal buttress 108 is not configured to engage the probe and therefore the expanded balloon of the internal buttress 108 may not contribute to the seal between the IRD 100 and the probe. Alternatively, the internal buttress 108 may be configured to engage the probe to contribute to the seal between the IRD 100 and the probe.

Figure 36:
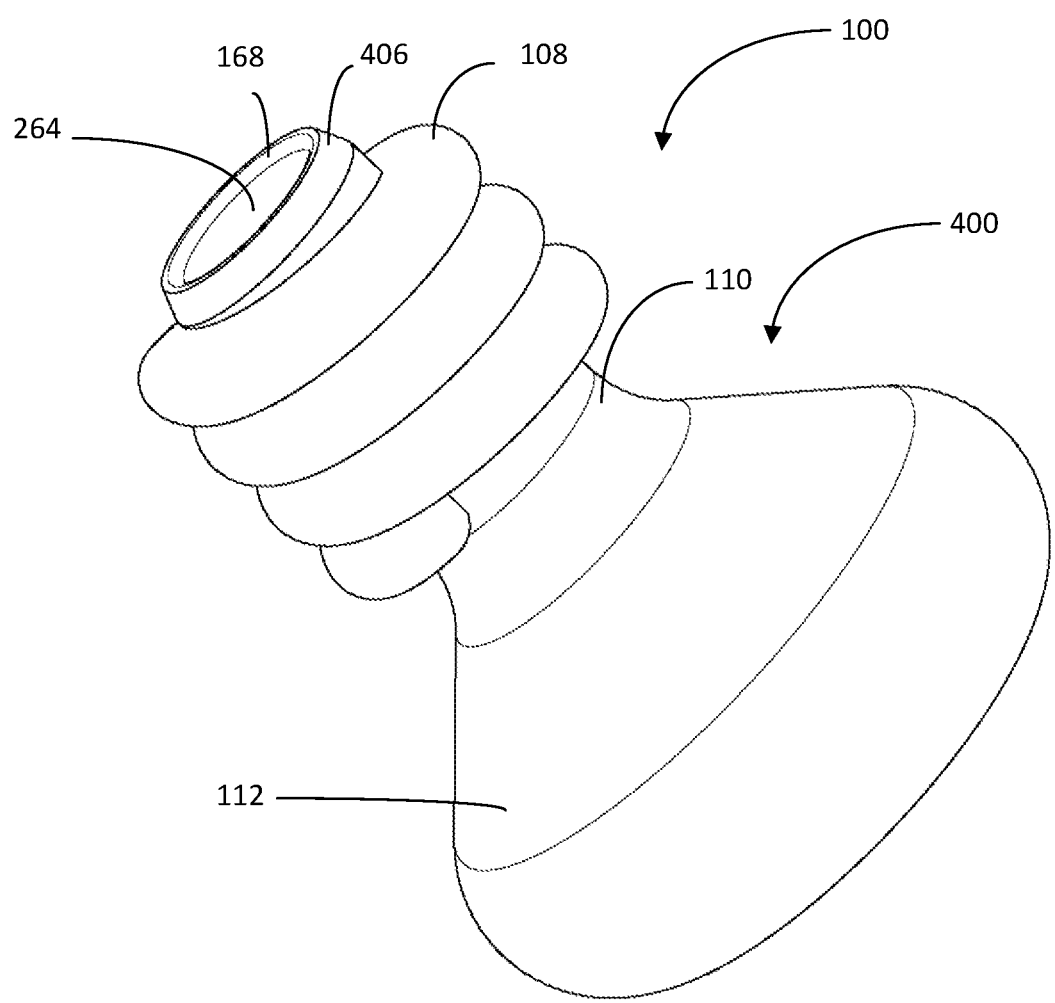
FIG. 36 shows in perspective view another insufflation retention device in accordance with various embodiments.

FIG. 36 shows a perspective view of another embodiment of the IRD 100. The external buttress 112, the midportion 110, and the internal buttress portion 168 may be formed of one piece as shown. The internal buttress 108 may be a balloon with an unexpanded state that is not shown. The internal buttress 108 may be a balloon with an expanded state that is shown. The internal buttress 108 may be affixed to the base member 400. The base member 400 may be semirigid with rigidity greater than the internal buttress 108 in the expanded state. The user may coil the internal buttress 108 around the base member 400 when the internal buttress 108 is in the unexpanded state. The user then inserts the IRD 100 into the patient and inflates the internal buttress 108 from the unexpanded state to the expanded state.

Again, in the unexpanded state, the internal buttress 108 has an open state. In the expanded state, the internal buttress 108 has a closed state. In the unexpanded state of the internal buttress 108, the base member may have an open state with the seam 292 along the length of the base member 400, not shown. In the expanded state of the internal buttress, the base member 400 may have a closed state. In the open state of the internal buttress 108 and the base member 400, the IRD 100 may be placed around the probe when the probe is in the body cavity, the body aperture, or both the body cavity and the body aperture, because the seam 292 is substantially open. In the closed state of the internal buttress and the base member 400, the IRD 100 may not be placed around the probe when the probe is in the body cavity, the body aperture, or both the body cavity and the body aperture 106, because the seam 292 is substantially closed. However, in the closed state of the internal buttress 108 and the base member 400, the IRD 100 may slide the IRD 100 over the probe when the probe is not in the body cavity, the body aperture, or both the body cavity and the body aperture, because the passageway for the probe is open.

As shown, the balloon portion of the internal buttress 108 is configured to not engage the probe when the probe is present, and therefore the internal buttress 108 that expands does not contribute to the seal between the IRD 100 and the probe.

As shown, the internal buttress portion may have an end portion with a chamfer 406 or beveled edge, which may facilitate entry of the IRD 100 through the body aperture into the body cavity. Alternatively, the internal buttress 108 may have the end portion with a blunt edge as shown in other embodiments.

Figure 37:
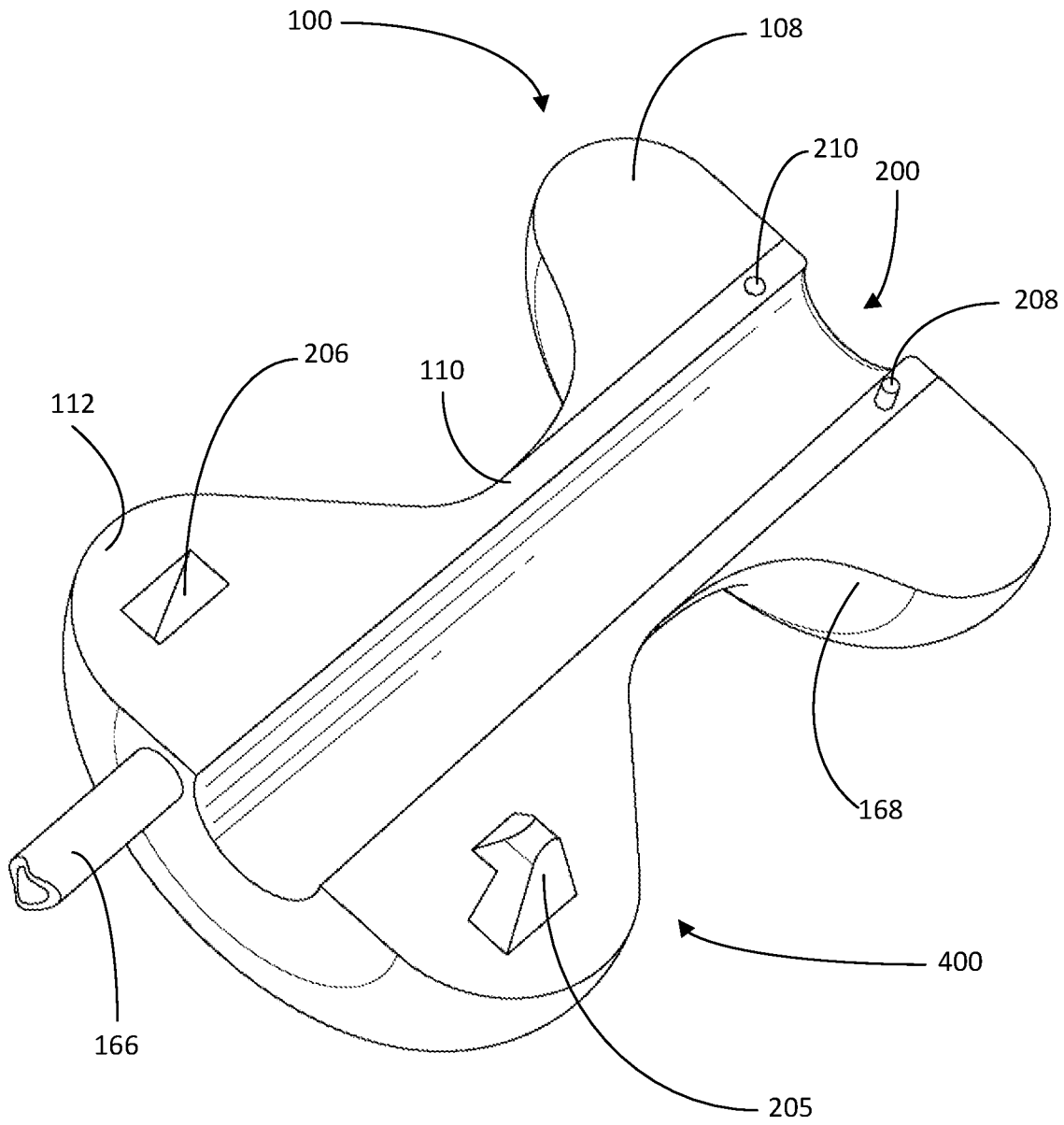
FIGS. 37-38 show isometric views of another insufflation retention device in accordance with various embodiments.
Figure 38:
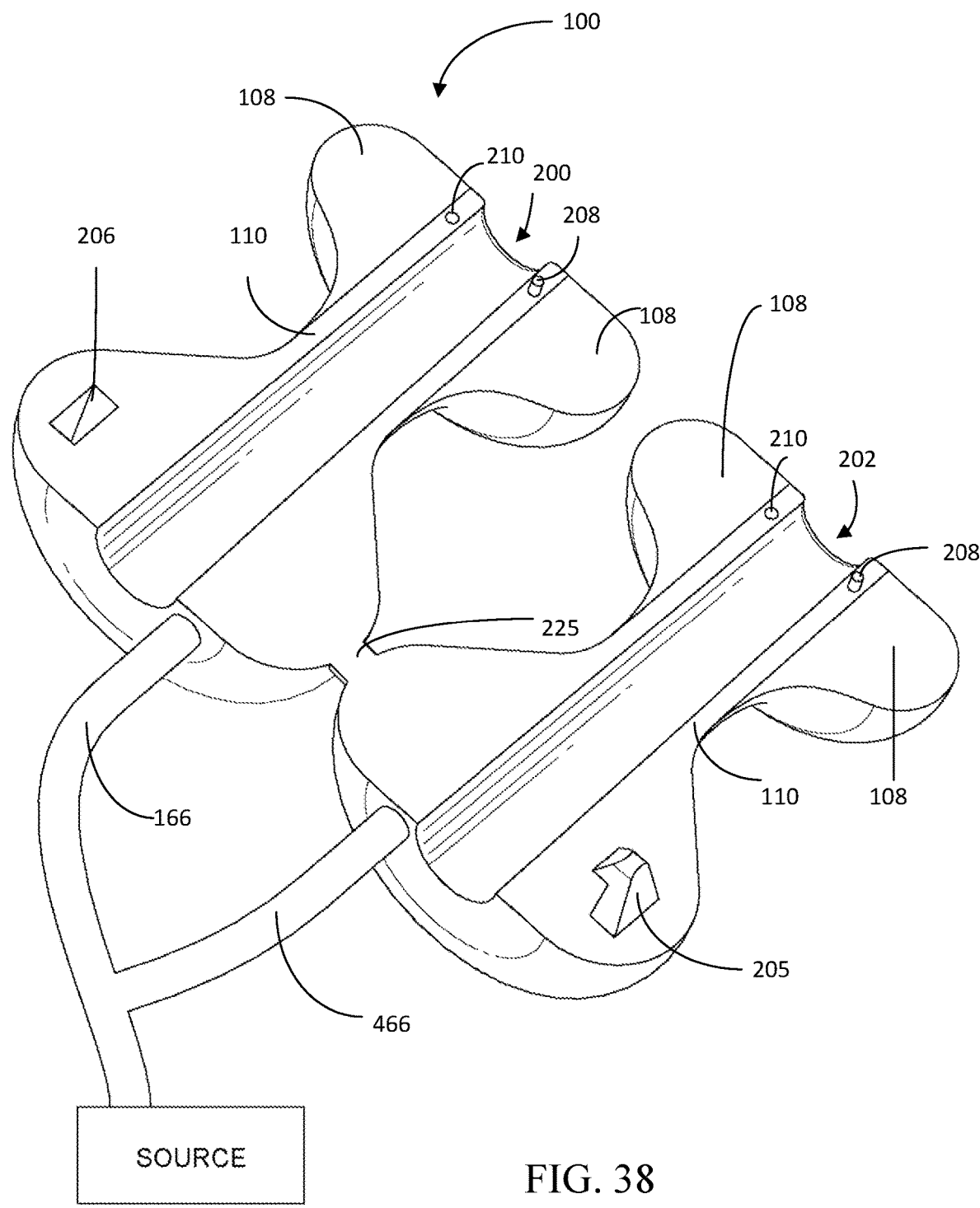

FIG. 37-38 show isometric views of other embodiments of the IRD 100. The external buttress 112, the midportion 110, and the internal buttress portion 168, known as the base member 400, may be formed of two or more pieces, or components. For example, the external buttress 112, the midportion 110, and the internal buttress portion 168 may be formed by the bringing together of the first body component 200 and the second body component 202. The first body component may have a first body external buttress 112, a first body midportion 110, and a first body internal buttress portion 168. The second body component may have a second body external buttress 112, a second body midportion 110, and a second body internal buttress portion 168. When the first body component and the second body component are combined, the first body component and the second body component may form the external buttress 112, the midportion 110, and the internal buttress portion 168 of the IRD 100.

The internal buttress 108 may be affixed to the base member 400 by welding, adhesive, or other suitable methodology. The first body component and the second body component may be semirigid with rigidity greater and the internal buttress 108 in the expanded state. The internal buttress 108 may be a balloon with an unexpanded state and as shown an expanded state. The balloon of the first body component 200 may be separate and isolated from the balloon of the second body component. The first body component 200 may have the expansion material line 166 in fluid communication with a first expansion material conduit that is in fluid communication with a first internal cavity of the first balloon. The second body component 202 may have a second expansion material line 466 in fluid communication with a second expansion material conduit that is in fluid communication with a second internal cavity of the second balloon. While the first balloon and the second balloon could be inflated independently by one source in a sequential manner or 2 sources in a simultaneous manner, the first expansion material line and the second expansion material line could be connected by a Y-valve, so the user could still inflate both the first balloon and the second balloon using a single source at the same time.

The first body component and the second body component may have the fasteners, such as snap 205 and a snap receptacle 206, by way of example and not limitation. Further, the first body component 200 and the second body component 202 may have a guide, such as a location pin 208 and a location hole 210, by way of example and not limitation. The fasteners on the first body component 200 may be positioned to engage the fasteners on the second body component 202. The guides on the first body component 200 may be positioned to engage the guides on the second body component 202. For the IRD 100 of any configuration, the actual component that is the first body component and the second body component may be used interchangeably after manufacture, because the first body component and the second body component are reversed mirror images of each other.

As shown in FIG. 38, the first body component 200 and the second body component 202 may be connected through a hinge 225 between the first body external buttress 112 of the first body component 200 and the second body external buttress 112 of the second body component 202.

As shown, the expanded portion of the internal buttress 108 may be configured to not engage the probe 250, and therefore the expanded portion of the internal buttress 108 does not contribute to the seal between the IRD 100 and the probe. The internal buttress 108 is configured to extend peripherally from the IRD 100 with expansion of the internal buttress 108.

Figure 39:
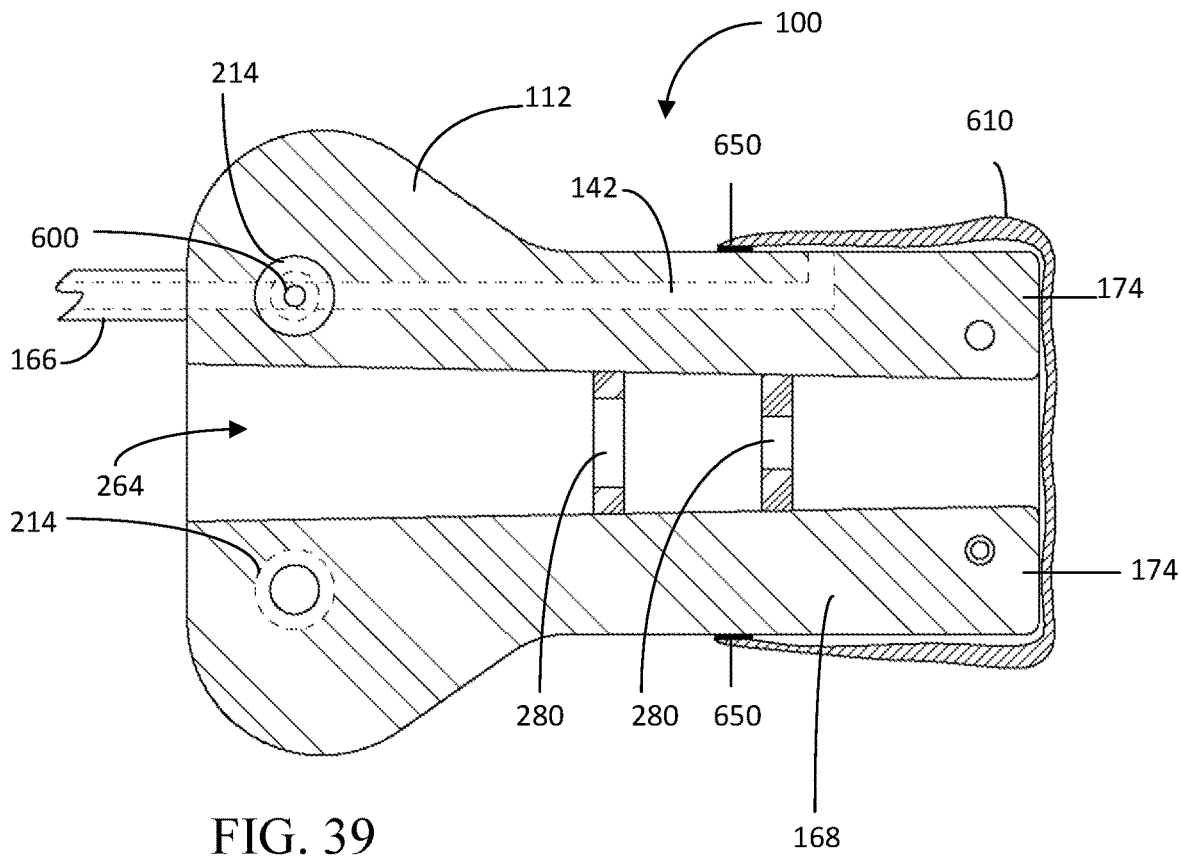
FIG. 39 shows in cross-section an insufflation retention device in accordance with various embodiments.
Figure 40:
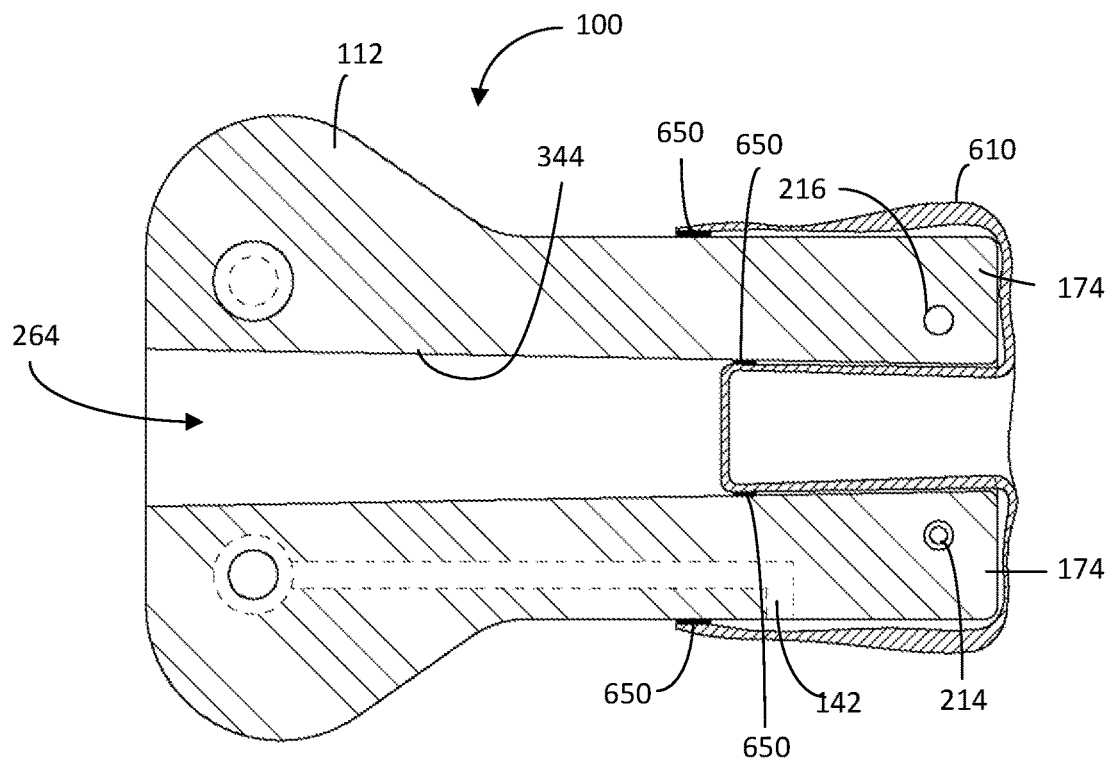
FIG. 40 shows in cross-section an insufflation retention device in accordance with various embodiments.
Figure 41:
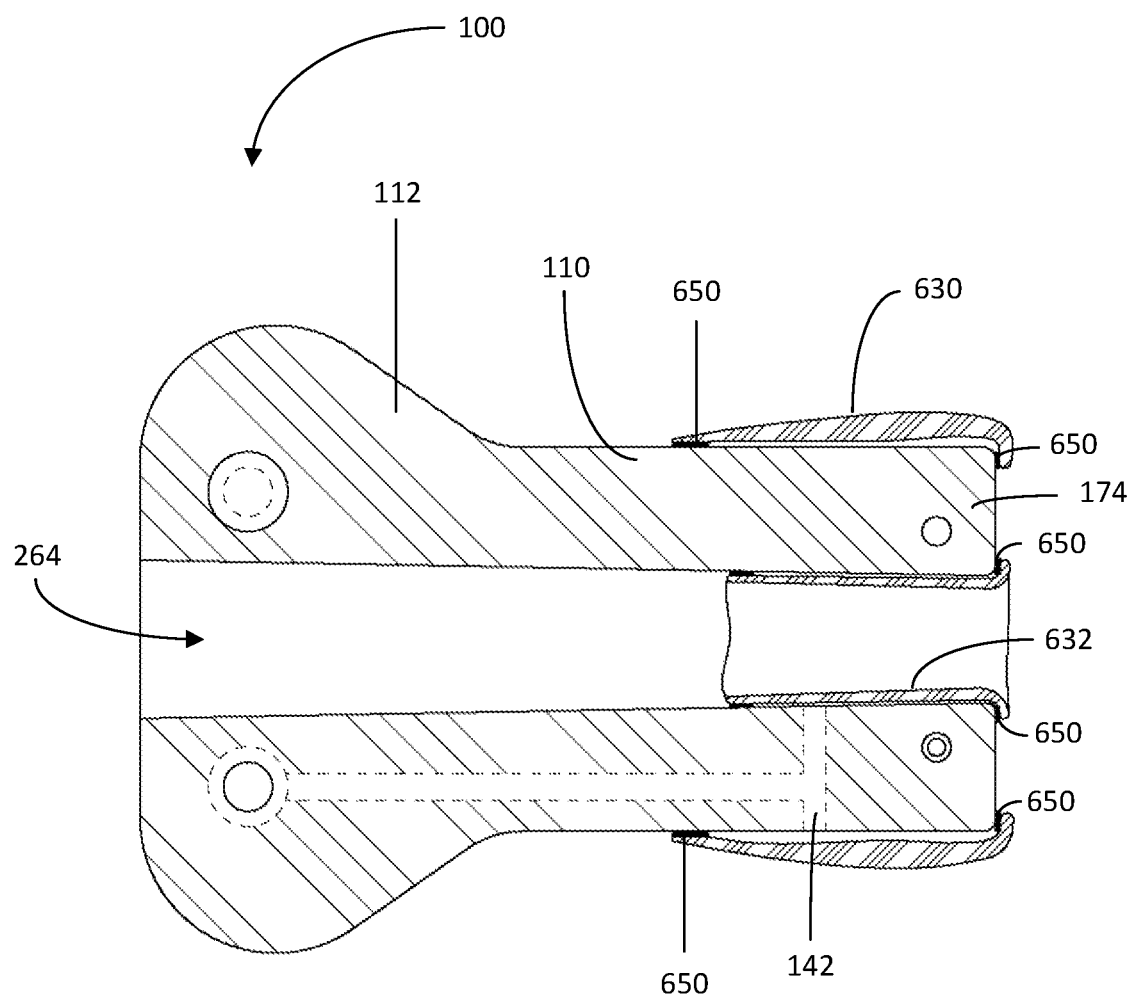
FIG. 41 shows in cross-section an insufflation retention device in accordance with various embodiments.
Figure 42:
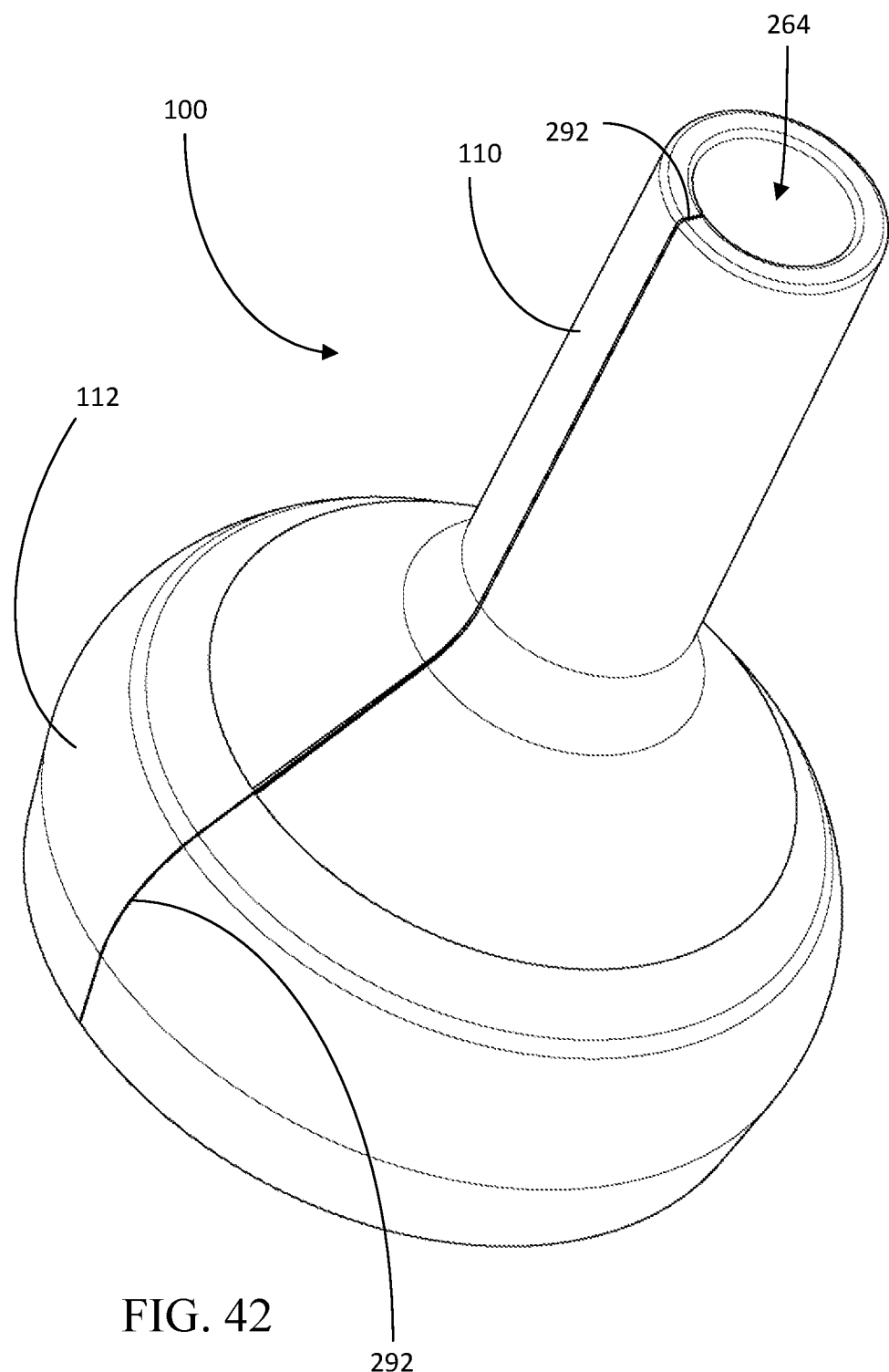
FIG. 42 shows an isometric view a portion of an insufflation retention device in accordance with various embodiments.
Figure 43:
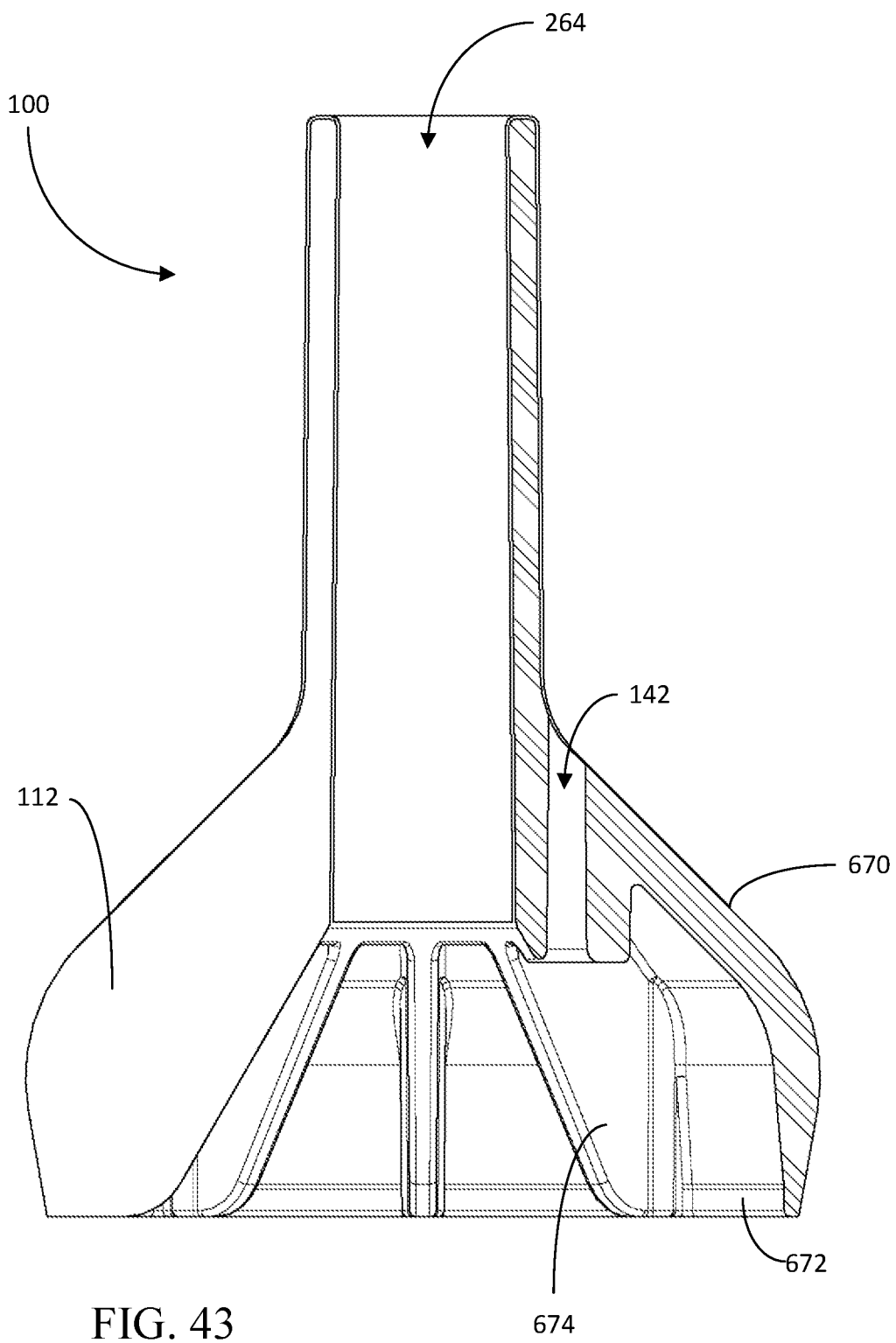
FIG. 43 shows in partial cross-section a portion of an insufflation retention device in accordance with various embodiments.
Figure 44:
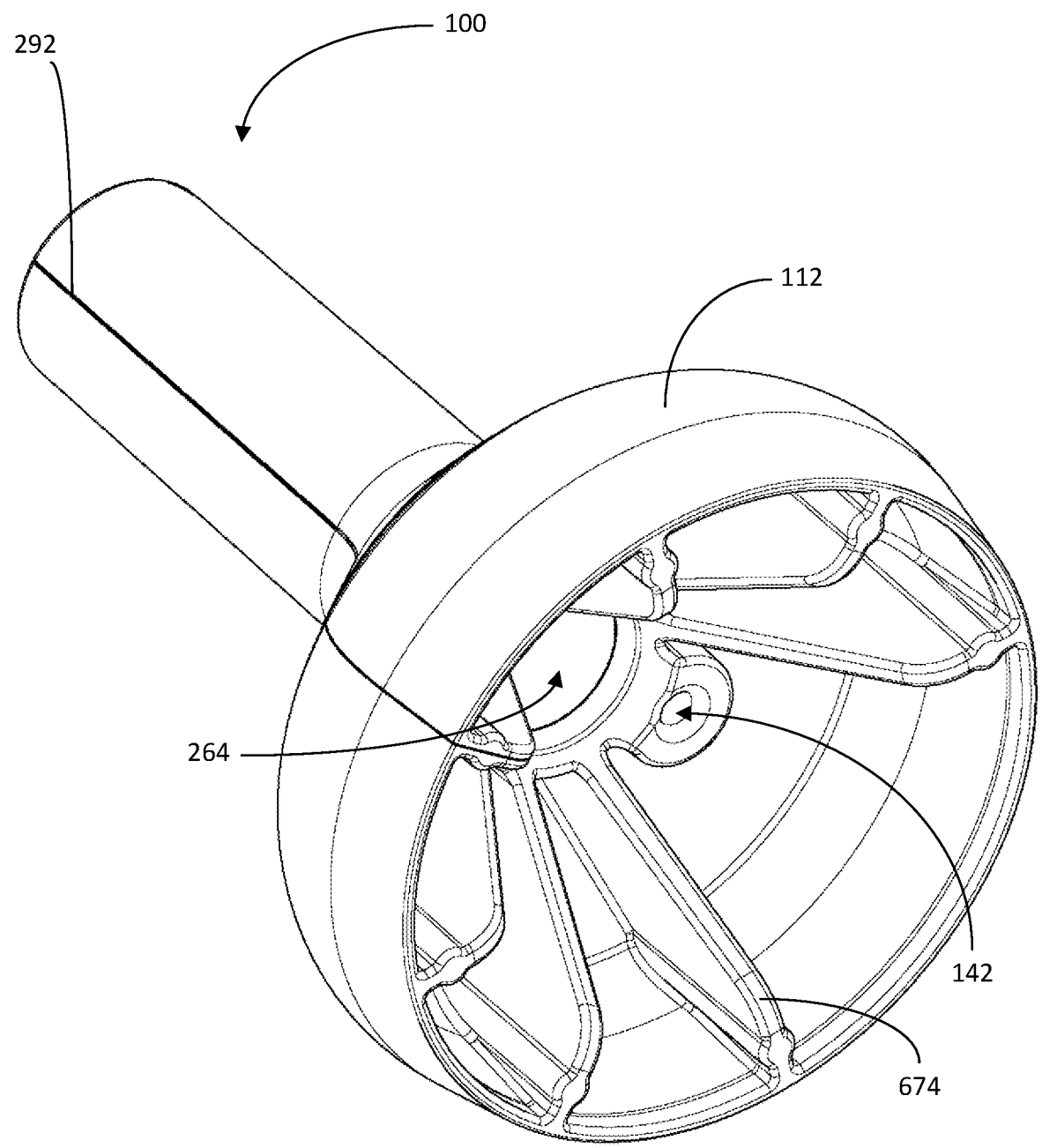
FIG. 44 shows an isometric view a portion of an insufflation retention device in accordance with various embodiments.
Figure 45:
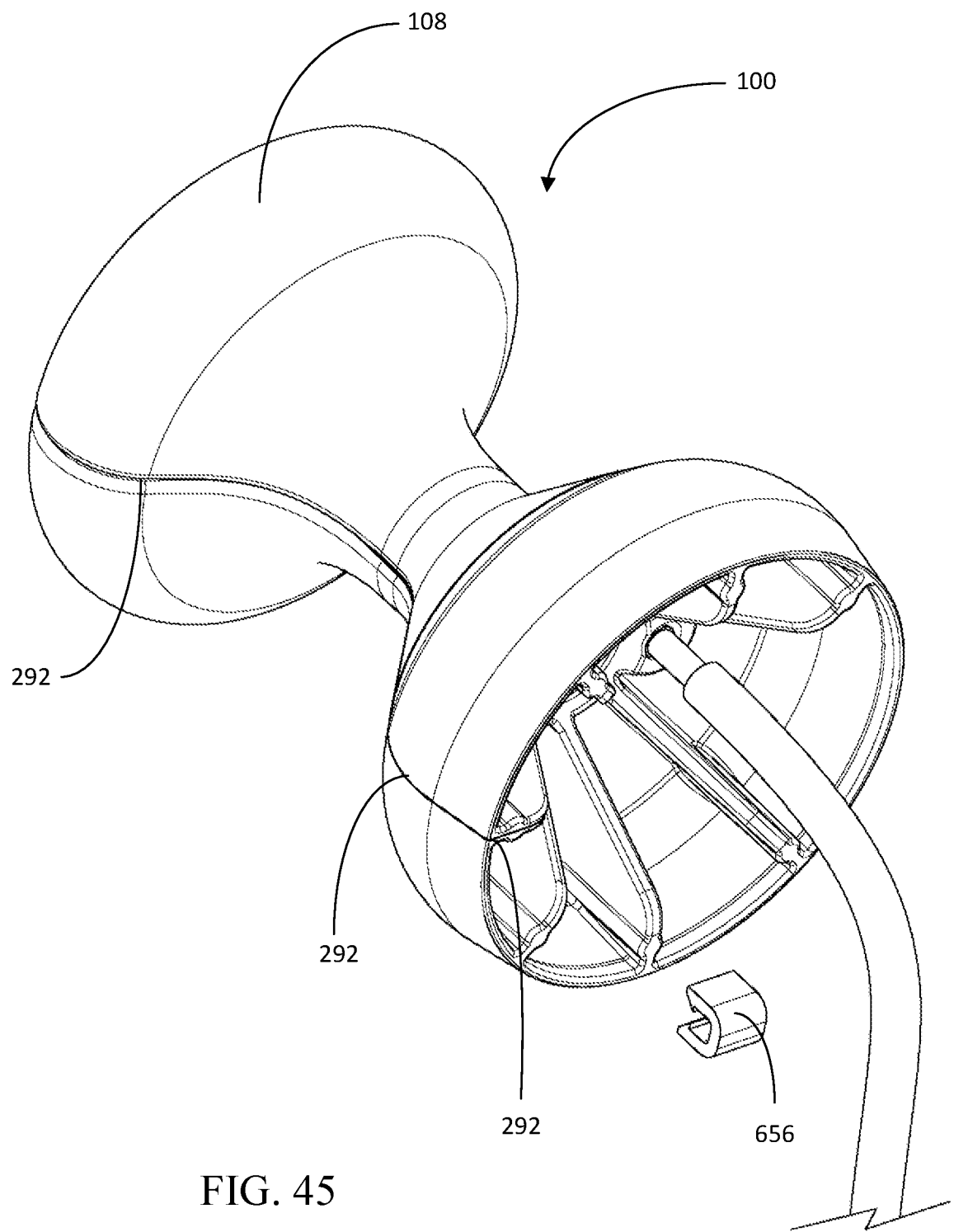
FIG. 45 shows an isometric view an insufflation retention device in accordance with various embodiments.
Figure 46:
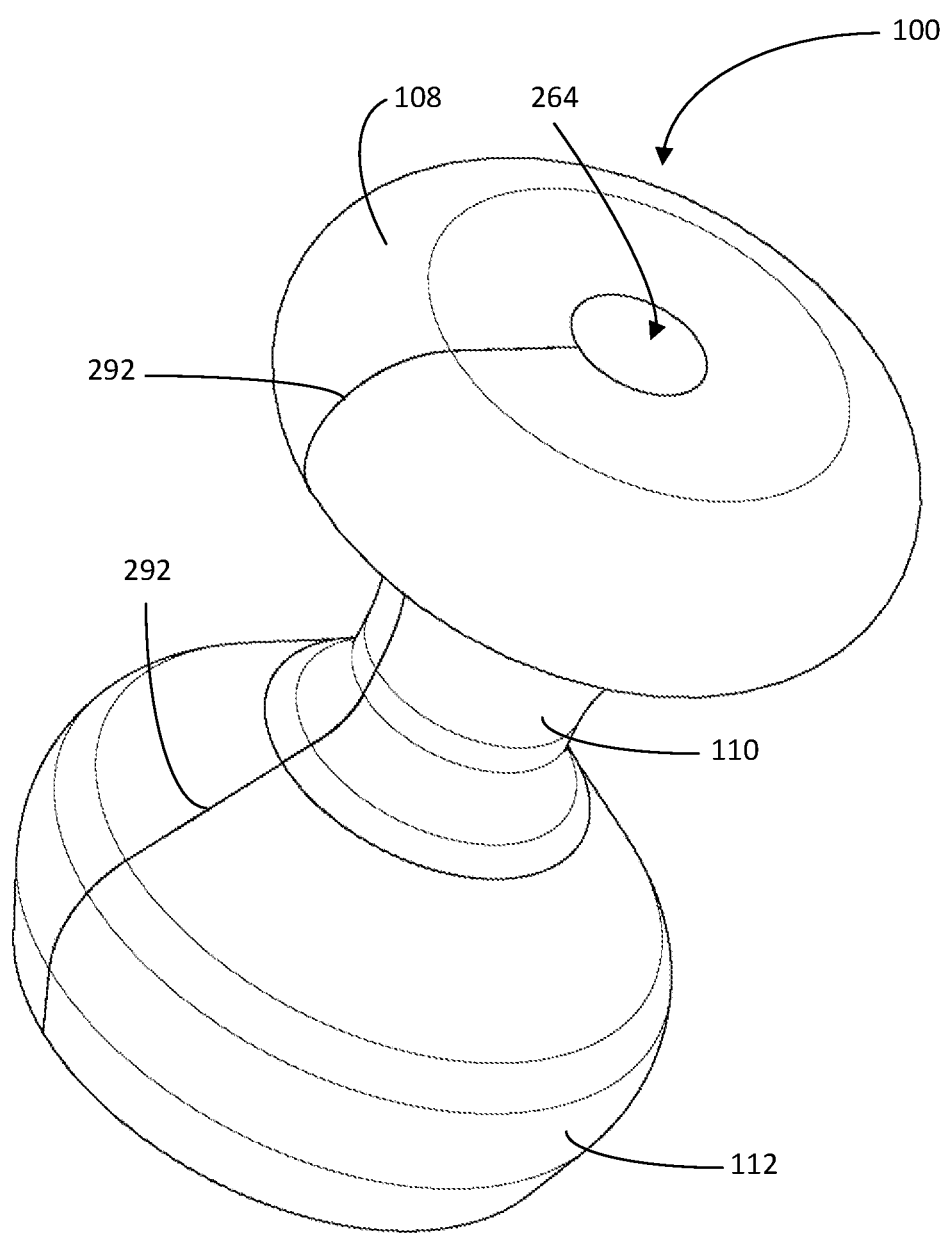
FIG. 46 shows an isometric view an insufflation retention device in accordance with various embodiments.

FIGS. 39, 40, and 41 show in cross-section of other embodiments of the IRD 100. The external buttress 112, the midportion 110, and the internal buttress portion 168 may be formed of two or more pieces, or body components. For example, the external buttress 112, the midportion 110, and the internal buttress portion 168 may be formed by the bringing together of the first body component and the second body component. The first body component may have a first body external buttress, a first body midportion, and a first body internal buttress portion. The second body component may have a second body external buttress, a second body midportion, and a second body internal buttress portion. When the first body component and the second body component are combined, the first body component and the second body component may form the body component, also known herein as the base member, of the external buttress, the midportion, and the internal buttress portion.

The body component shown in FIG. 39 is complementary to the body component shown in FIG. 40 or FIG. 41. In other words, external buttress 112, the midportion 110, and the internal buttress portion 168 may be complementary. The external buttress 112, the midportion 110, and the internal buttress portion 168 may be formed of one piece as shown. The passageway 264 extends along an entire length of a side of the IRD 100 from the internal buttress 108 through the midportion 110 to the external buttress 112. The passageway 264 may be defined by a passageway structure that extends from the internal buttress 108 to the external buttress 112.

The complementary features of the body components may be reversed as needed. As shown, the expansion material line 166 for the IRD 100 may be present on just one of the first body component or the second body component. As shown in the dotted lines, the expansion material conduit 142 may extend throughout the body component from the expansion material line 166 to the internal cavity of the balloons present, so that the expansion material line is in fluid communication with the internal cavity. The first body component may be in fluid communication with the second body component through a valve 600, such as by way of example and not limitation, a male valve/snap as shown in FIG. 39 that mates with a female valve/snap in FIG. 40 or FIG. 41. In other words, the 2 components snap together to create a continuous air path to allow for inflation from one expansion material line 166 and source. So, while the balloons are isolated in the sense that one is formed and attached to the first body component and another is formed and attached to the second body component, the balloons may be in fluid communication with the expansion material line 166 and source that is the same for both balloons. In addition, the body components may have fasteners or location guides such as male/female locating features (214 and 216, respectively), as shown in the internal buttress portion, to facilitate alignment of the first body component and the second body component and assembly of the IRD 100.

As with other embodiments, an internal surface 344 of the passageway 264 may support one or more O-ring type structures also known herein as washers or sphincters.

One passageway may have O-ring type structures 280 of different diameters so that probes of varying diameters can be positioned in the interior of the passageway to form a probe O-ring type structure seal. If there is more than one O-ring type structure 280, the larger diameter may be towards the external buttress 112 and the smaller diameter may be towards the internal buttress 108, but the reverse is contemplated.

The internal buttress 108 may be a balloon as shown. The balloon may have variable thickness 610 to facilitate inflation for expansion with insertion of the expansion material. The balloon may be thinner towards the first end 174 of the internal buttress portion 168 to facilitate expansion of the balloon towards the internal buttress portion 168.

Different balloon arrangements are shown and contemplated. FIG. 39 shows the balloon extends from an external periphery of the internal buttress portion around on to the first end 174 of the internal buttress portion 168. The balloon in the expanded state may be configured to engage the probe, when present, through the passageway 264 to form a seal between the balloon and the probe. The balloon may be configured to not engage the probe, when present, through the passageway 264 in order to not form a seal between the balloon and the probe, in which case other features would form a seal between the IRD 100 and the probe in the passageway 264. In either situation of certain embodiments, the balloon in the expanded state is not closed and so without the probe in the IRD 100, the IRD 100 is unable to retain the insufflation material.

Figure 49:
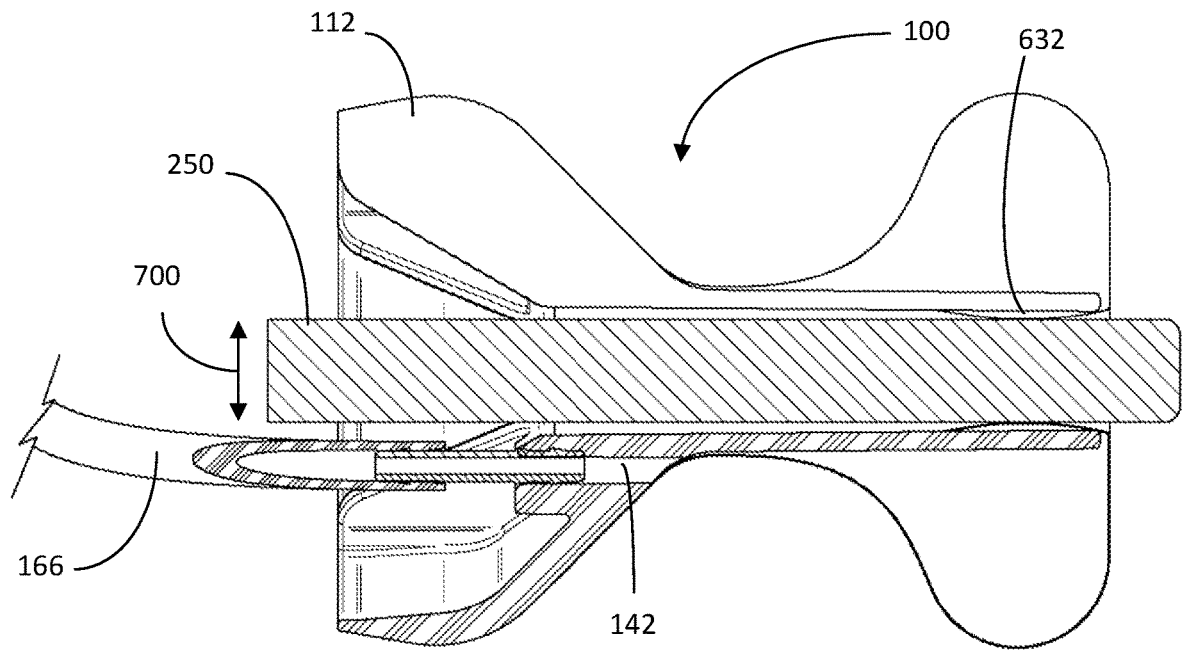
FIGS. 49 (A)-(B) show in partial cross-section an insufflation retention device of one size configured for accommodate probes of multiple sizes in accordance with various embodiments.
Figure 49:
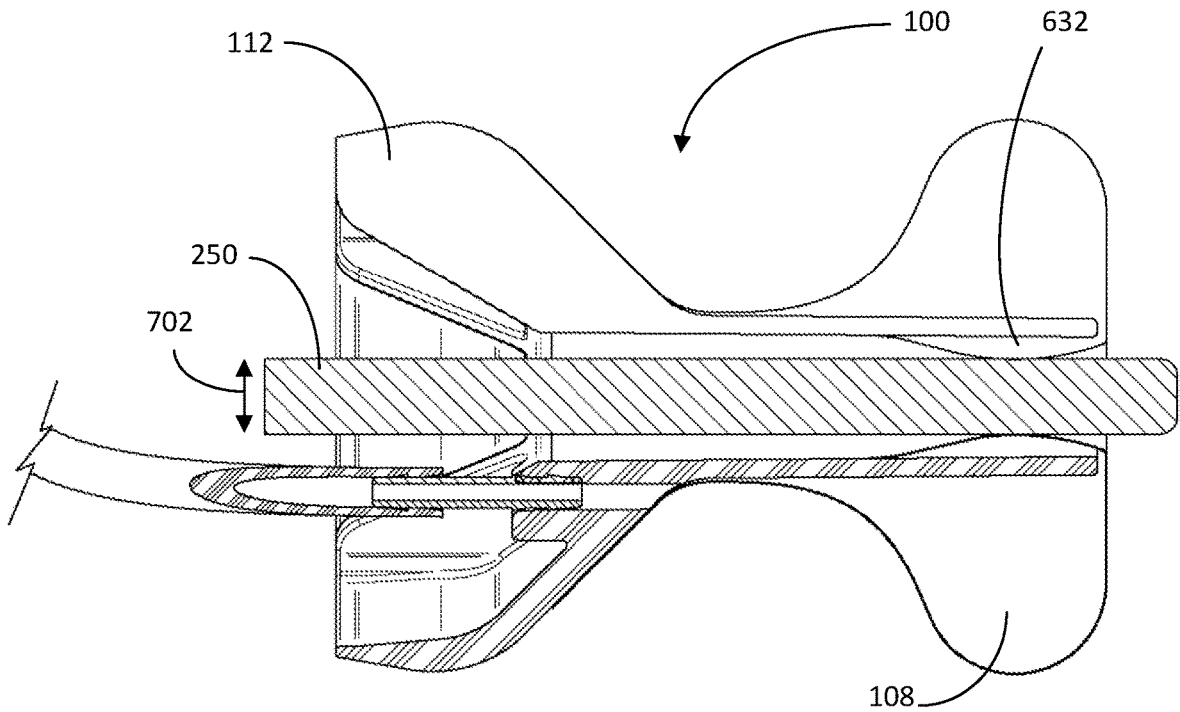

FIG. 40 shows the balloon extends from the external periphery of the internal buttress portion 168 around and over the first end 174 of the internal buttress portion 168 into the passageway 264. While the depth of the balloon into the passageway 264 is shown to be substantially similar to the depth of the balloon along the external periphery of the internal buttress 108, the depth of the balloon into the passageway 264 may be substantially greater or less than the depth of the balloon along the external periphery of the internal buttress 108. Inflation of the balloon in the passageway 264 may create a probe balloon seal that accommodates probes of different diameters as will be shown in FIG. 49 (A) shown with larger diameter 700 and 49 (B) and smaller diameter 702. With the probe within the passageway, a predetermined volume of expansion material may be inserted into the internal cavity of the balloon. Resistance to further insertion of expansion material might be felt by a user using a syringe, pressure cuff pump, or other suitable expansion material source. In certain embodiments, the balloon in the expanded state is not closed and so without the probe in the passageway 264, the IRD 100 is unable to retain the insufflation material.

FIG. 41 shows the balloon as an internal balloon 632 within the passageway 264 and an external balloon 634 outside and surrounding the passageway 264. The internal balloon 632 and the external balloon 634 may be in fluid communication as shown, such that a single expansion material source may be used to expand both balloons at the same time, or the internal balloon and the external balloon may not be in fluid communication, such that a single expansion material source would need to be used to expand the balloons at different times or different expansion material sources would need to be used to expand the balloons at simultaneous times.

These embodiments are considered discontinuous for the internal buttress in that the embodiments have the open state in which the internal buttress may be placed around the probe when the probe is in the body aperture, the body cavity, or both when the IRD 100 is in the open state. Further, the internal buttress in the embodiments have the closed state in which the internal buttress may be closed around the probe when the probe is in the body aperture, the body cavity, or both.

In these various embodiments, the balloon may be manufactured separately from the base member and then attached to the base member by heat welding or other suitable methodology at appropriate contact points 650.

FIGS. 42-49 show another embodiment of the IRD 100. Rather than the two-piece construction as a first body component and a second body component shown in FIGS. 39, 40, and 41, the IRD 100 shows a one-piece construction of the base member 400 as the external buttress 112, the midportion 110, and the internal buttress portion 168. As with these other embodiments, the internal buttress 108 may be a balloon that upon expansion extends peripherally from the base member 400.

As shown in FIGS. 42-49, the balloon may extend further along the exterior surface of the base member than the balloon extends along the interior of the base member in the passageway, or vice versa. The balloon may extend substantially the same length along the exterior surface of the base member as the balloon extends along the interior of the base member in the passageway, also. The balloon in the interior of the base member in the passageway may engage the probe to form a probe balloon seal to aid with retention of the insufflation material. The balloon on the exterior of the base member may form the body internal buttress seal to aid in retention of the insufflation material.

The IRD 100 has the seam 292 that extends all along the length of the base member from the external buttress to the internal buttress portion. The seam 292 is also present in the balloon of the internal buttress. Because of the seam 292, the IRD 100 shown in FIGS. 42-49 may have the open state and the closed state. The IRD 100 may be placed around the probe when the probe is in the body aperture, the body cavity, or both when the IRD 100 is in the open state. Further, the internal buttress has the closed state in which the internal buttress may be closed around the probe when the probe is in the body aperture, the body cavity, or both.

Figure 47:
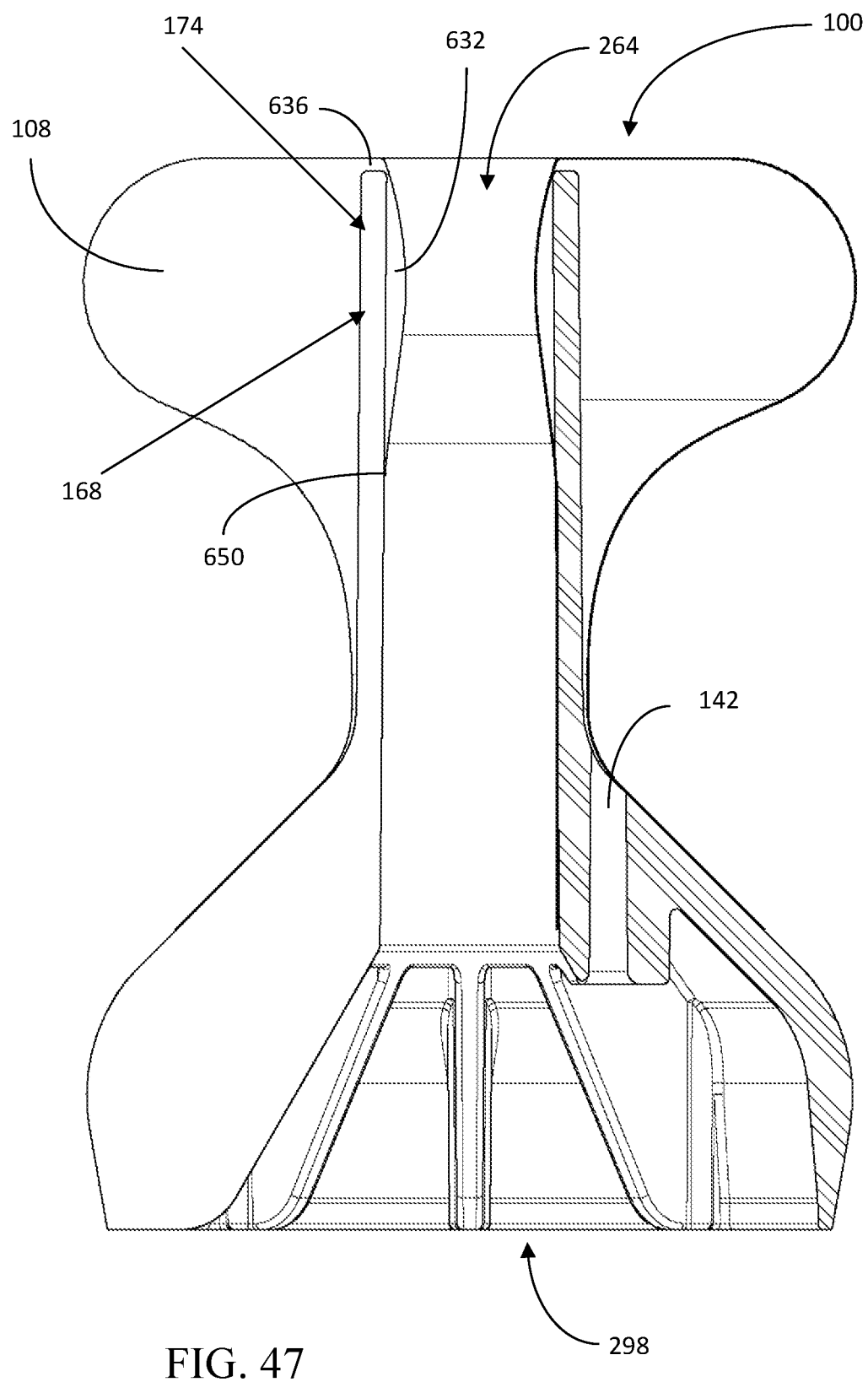
FIG. 47 shows in partial cross-section an insufflation retention device in accordance with various embodiments.
Figure 48:
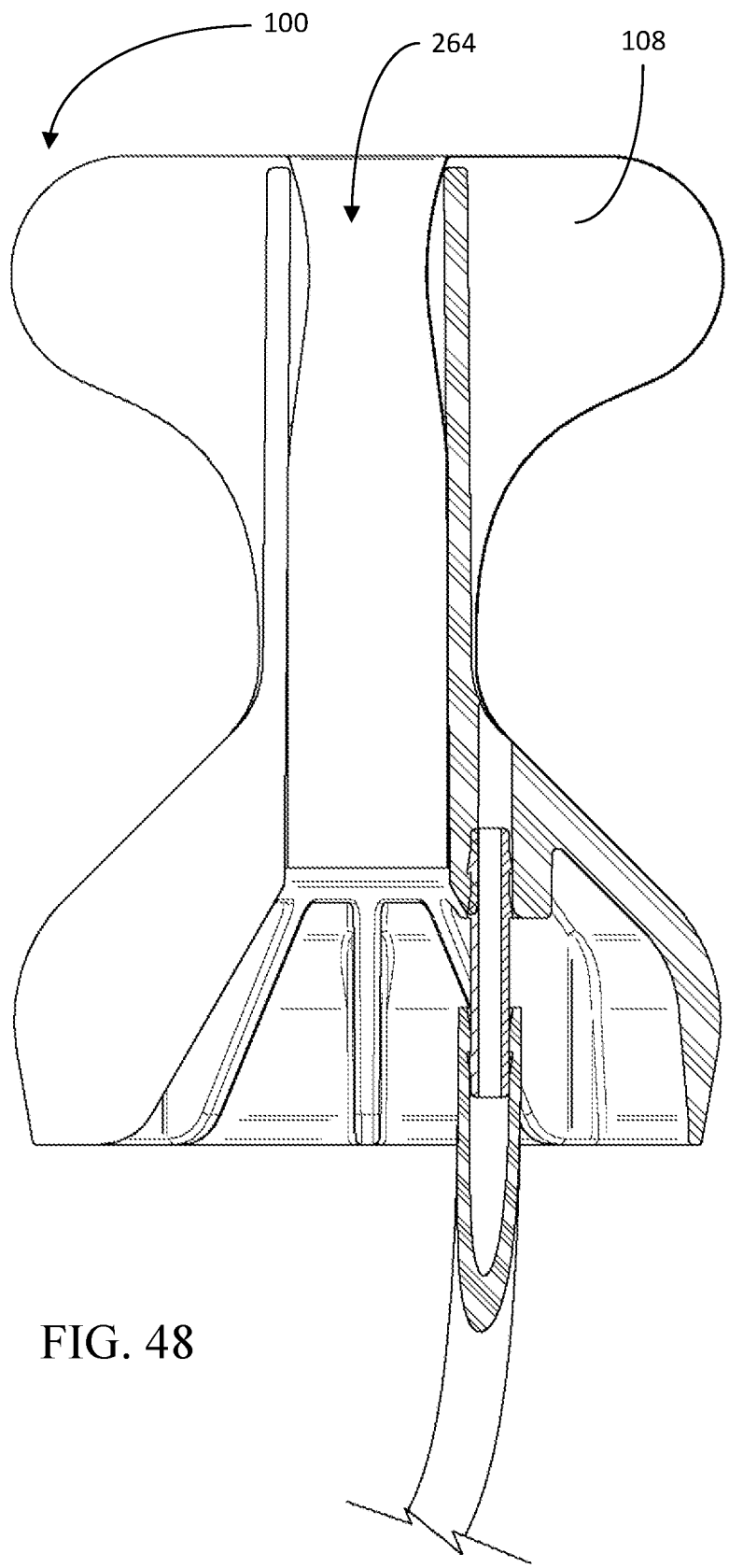
FIG. 48 shows in partial cross-section an insufflation retention device in accordance with various embodiments.

FIG. 47 shows the balloon extends from the external periphery of the internal buttress portion 168 around and over 636 the first end 174 of the internal buttress portion 168 into the passageway 264, also may be seen in FIG. 40.

The external buttress 112 may have an exterior surface 670 and an interior surface 672. The external buttress 112 may have one or more support struts 674 on the interior surface 672.

Figure 50:
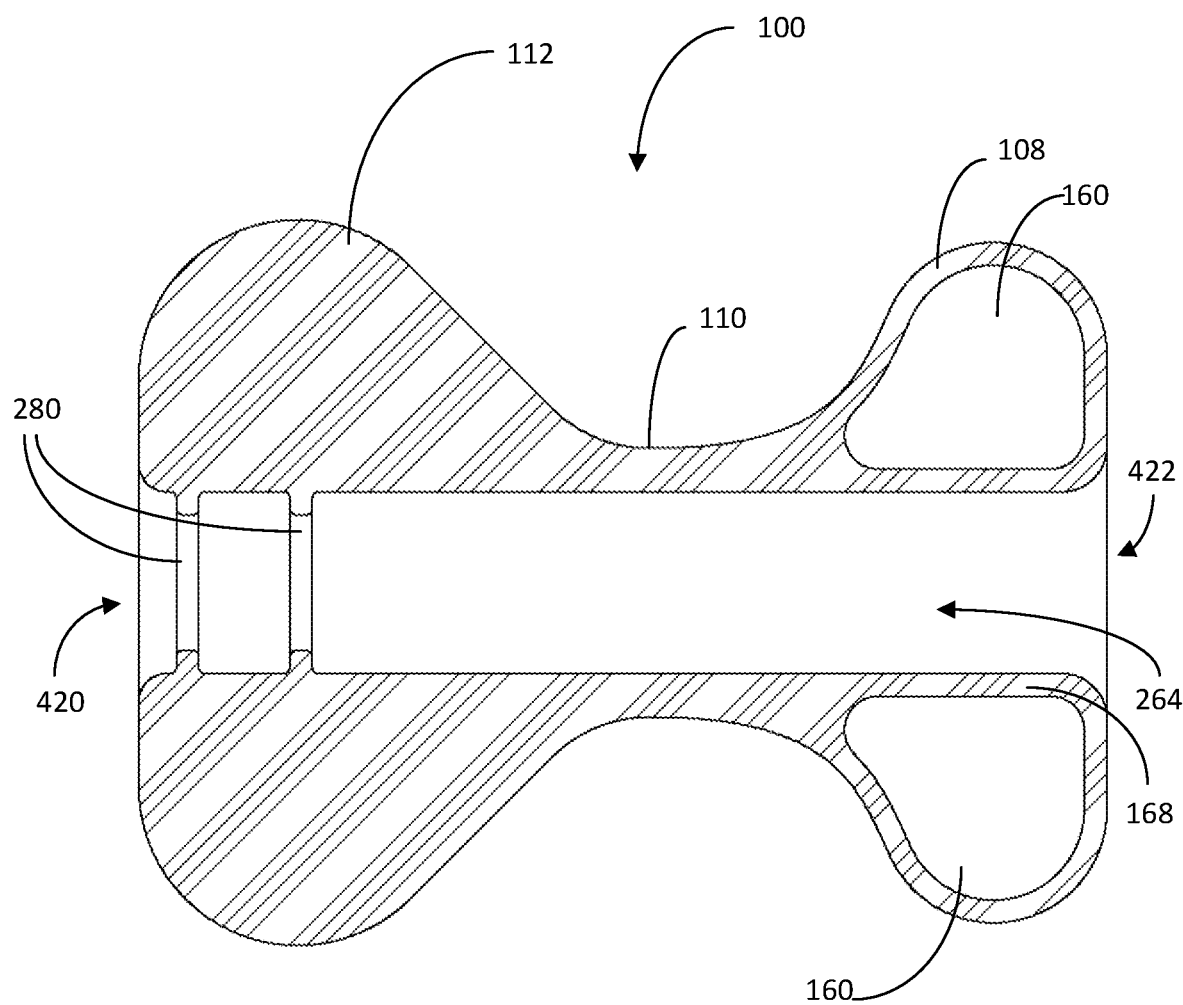
FIG. 50 shows in cross-section another insufflation retention device in accordance with various embodiments.
Figure 51:
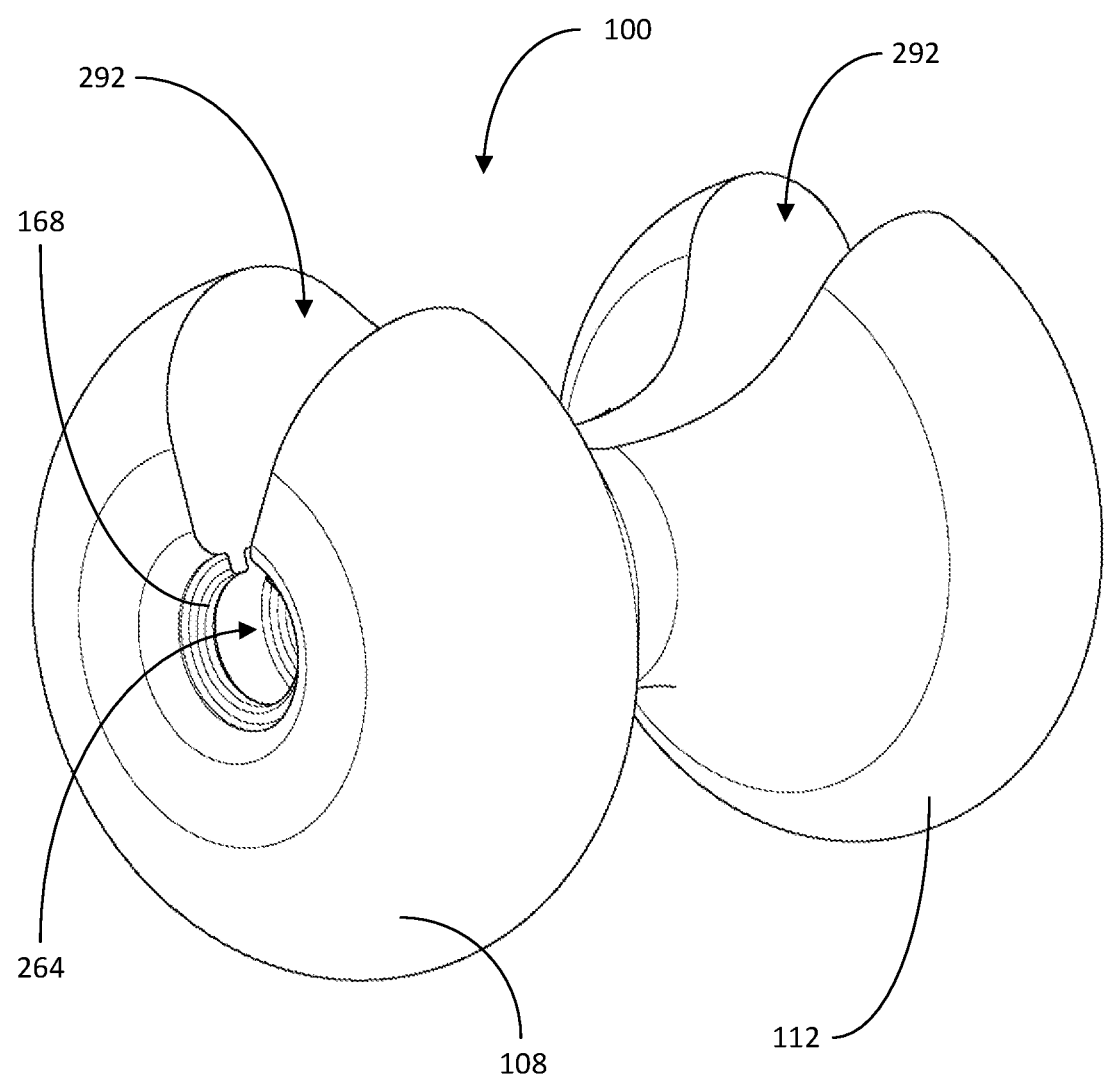
FIG. 51 shows in perspective view the insufflation retention device of FIG. 50 in accordance with various embodiments.

FIG. 50 shows in cross-section and FIG. 51 shows in perspective views another embodiment of the IRD 100, wherein the internal cavity 160 of the internal buttress 108 may extend peripherally upon expansion from the internal buttress portion 168 of the base member, which further includes the midportion 110 and the external buttress 112. The passageway 264, configured for passage of the probe when present, is shown to have two O-ring type structures 280, but it will be understood that it could have one or more O-ring type structure 280. The O-ring type structure 280 on the inner diameter of the base member allows formation of a seal between the IRD 100 and the probe when present. As shown, the O-ring type structure 280 may be surrounded by the external buttress 112. One or more of the O-ring type structure 280 may also be surrounded by some combination of the midportion 110 and the internal buttress portion 168. The O-ring type structure 280 may function as a sphincter that allows a seal on probes of various diameters. The IRD 100 has the seam 292 along its length from a first opening 420 to a second opening 422. The IRD 100 has an open state and a closed state, because the internal buttress is discontinuous.

As shown in FIG. 51, the IRD 100 may have the seam 292 that is not absent through abutment of adjacent surfaces when the IRD 100 is in the closed state. However, in the closed state where the seam 292 is not absent, a probe could not be slid from outside the IRD 100 through the seam 292 into the passageway 264.

As shown, the internal buttress 108 in the expanded state is configured to not engage a probe when present to form a seal between the internal buttress 108 that is expanded and the probe.

Figure 52:
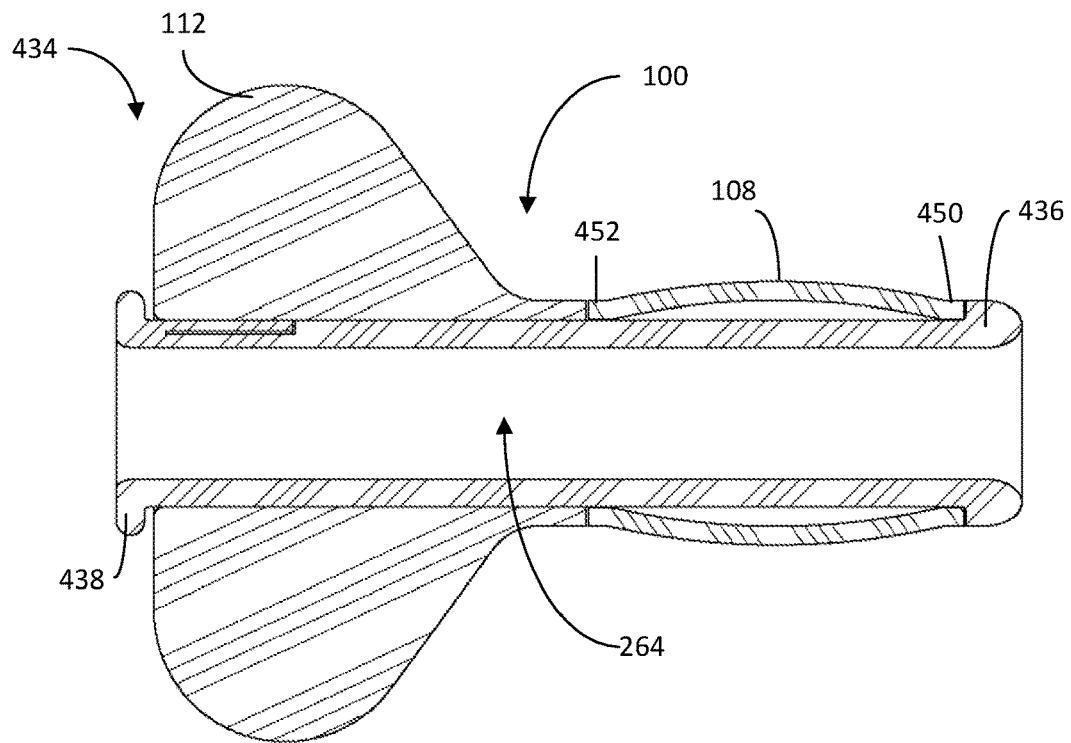
FIGS. 52 (A)-(B) show in cross-section another insufflation retention device in accordance with various embodiments.
Figure 52:
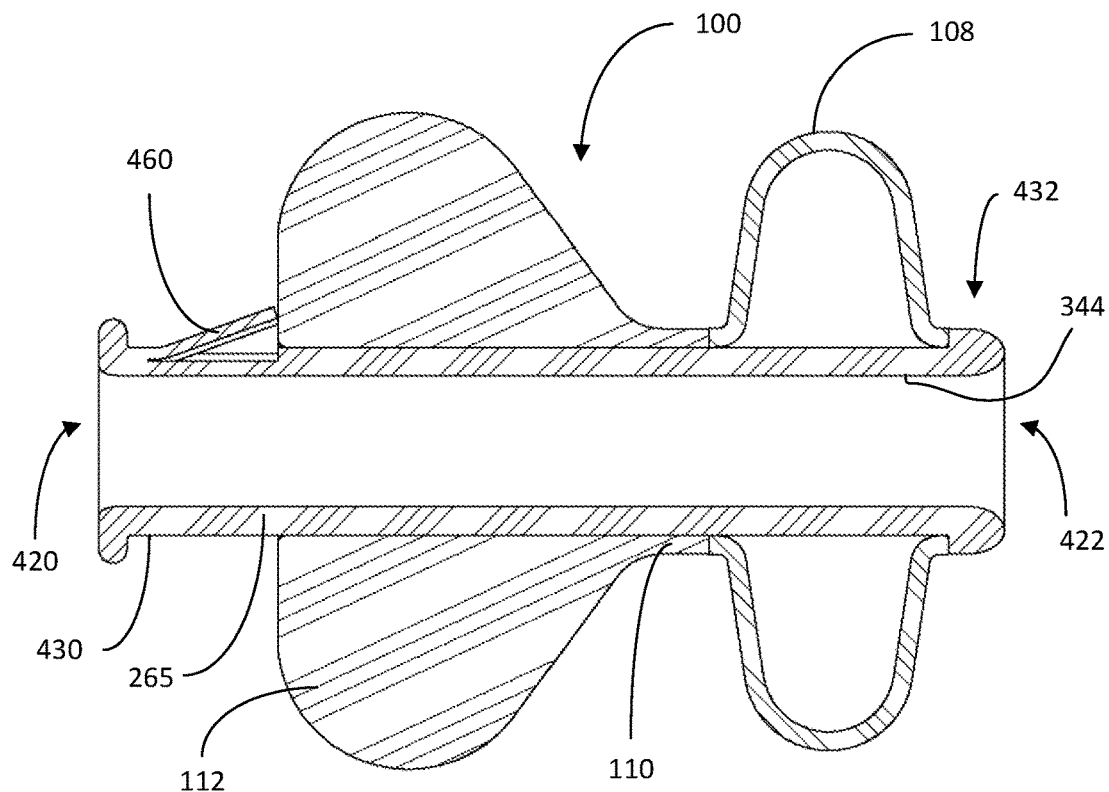

FIGS. 52 (A) and 52 (B) show cross-section views of another embodiment of the IRD 100. As in other embodiments, the passageway 264 extends along a length from the internal buttress 108 through the midportion 110 to the external buttress 112. The passageway 264 may be defined by a passageway structure 265 that extends from the internal buttress 108 to the external buttress 112. The internal buttress 108 may surround and lay contactingly adjacent an external surface 430 of the passageway structure 265 towards an insertion end 432, otherwise known as a first end, of the passageway structure 265. The external buttress 112 may surround and lay contactingly adjacent the external surface 430 of the passageway structure 265 towards a handle 434, otherwise known as an opposing, second end, of the passageway structure 265.

The internal buttress 108 may be made of an elastomeric material, such as polymer or natural rubber. The external buttress 112 may be made of a semirigid material that is more rigid than the elastomeric material of the internal buttress 108. The midportion 110 may be made of the semirigid material and may include elastomeric material, also.

The first end or the insertion end 432 of the passageway structure 265 may include an internal buttress retention member 436. The internal buttress 108 may be located between the midportion 110 and the internal buttress retention member 436.

The opposing, second end or the handle 434 of the passageway structure 265 may include an external buttress retention member 438. The external buttress 112 may be located between the midportion 110 and the external buttress retention member 438.

The internal buttress 108 may be fixed relative to the internal buttress retention member 436 at a first end 450 of the internal buttress 108, and the internal buttress 108 may be mobile relative to the internal buttress retention member 436 at an opposing, second end 452 of the internal buttress 108. The internal buttress 108 may be biased towards extension of the opposing, second end 452 of the internal buttress 108 towards the external buttress 112. This bias of the internal buttress 108 towards the external buttress 112 may bias the external buttress 112 towards the external buttress retention member 438. The external buttress retention member 438 may be configured to keep the external buttress 112 from extending past the handle 434 and off the passageway structure 265.

This embodiment may be considered to function in a manner like a well nut. The IRD 100 may have an insertion state and a retention state. In the insertion position state, the user may insert the IRD 100 through the body aperture 106 into the body cavity 104. When the internal buttress is in the body cavity 104, the user may slide the external buttress 112 relative to the external surface 430 of the passageway structure 265 towards the internal buttress 108. When the external buttress 112 slides towards the internal buttress 108, the internal buttress 108 extends peripherally away from the passageway structure 265 when the IRD 100 and is in the retention state. The internal buttress 108 may now prevent the IRD 100 from leaving the body cavity 104 and may promote retention of the insufflation material.

Further, the IRD 100 may include a latch 460 to maintain the retention state. In the insertion state, the latch 460 may be surrounded by the external buttress 112. When the external buttress 112 slides towards the internal buttress 108, the external buttress 112 may no longer surround the latch 460. The latch 460 may be biased to extend peripherally from the passageway structure 265. When the external buttress 112 no longer surrounds the latch 460, the latch 460 may extend peripherally from the passageway structure 265. When the latch 460 extends peripherally from the passageway structure 265, the latch 460 may retain the external buttress 112 and the internal buttress 108 in the retention state. A user may push the latch 460 centrally towards the passageway structure 265 so that the bias of the external buttress 112 towards the external buttress retention member 438 is no longer counteracted by the latch 460. Therefore, the external buttress 112 will slide towards the external buttress retention member 438 and the internal buttress 108 may move centrally towards the passageway structure 265 so that the internal buttress 108 may no longer prevent the IRD 100 from leaving the body cavity 104 and may no longer promote retention of the insufflation material. The IRD 100 has been transitioned from the retention state back to the insertion state, so that the IRD 100 may be removed from the body aperture 106 and the body cavity 104.

Figure 53:
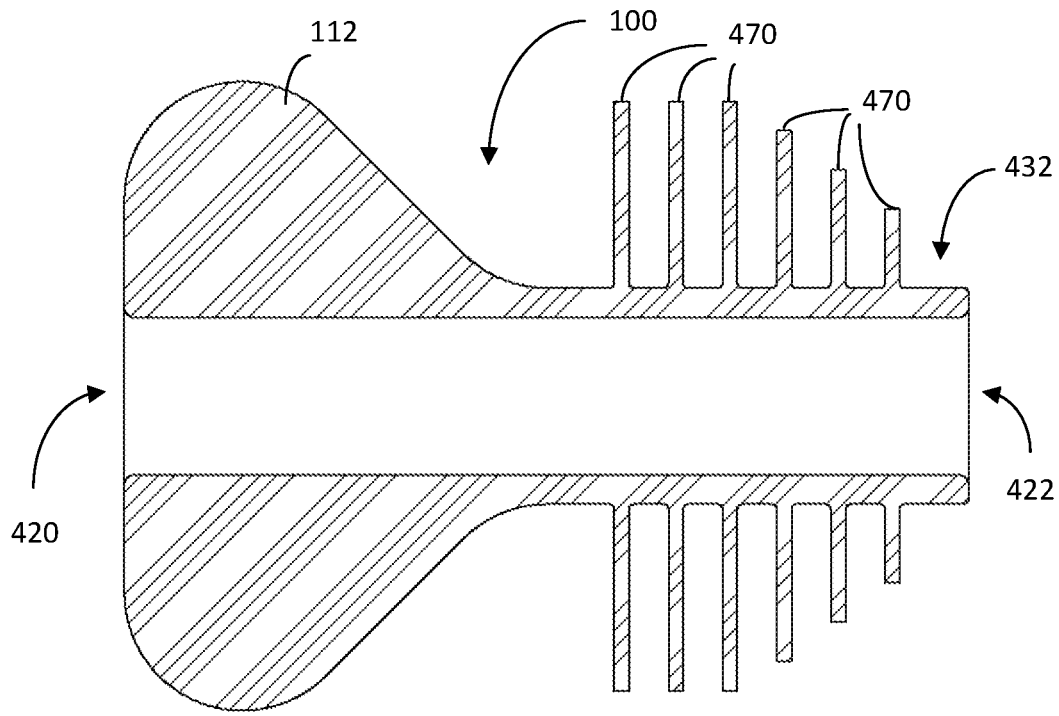
FIG. 53 shows in cross-section an insufflation retention device in accordance with various embodiments.
Figure 54:
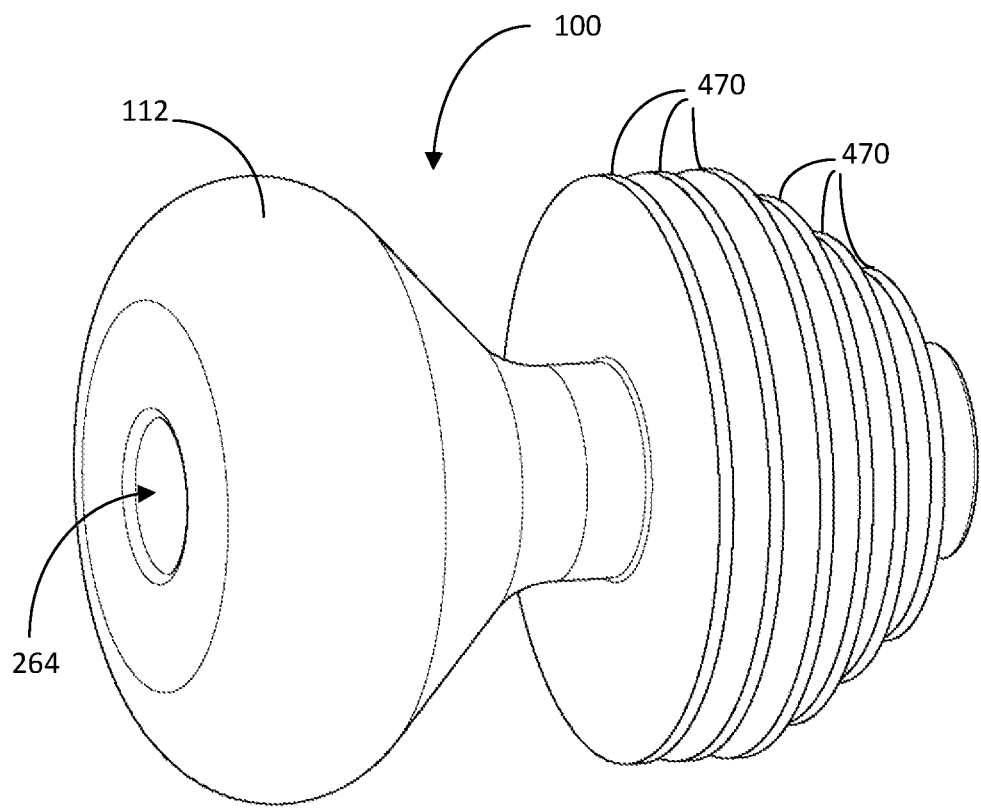
FIG. 54 shows in perspective view the insufflation retention device of FIG. 53 in accordance with various embodiments.

FIG. 53 shows in cross-section and FIG. 54 shows in perspective views another embodiment of the IRD 100. Previously, embodiments have been shown with O-ring type structures or sphincters interior to the passageway. In this embodiment, O-ring type structures are shown external to the passageway structure. The embodiment looks somewhat like a fir tree with one or more branches 470. Branches 470 of the tree may be shorter towards the insertion end 432 of the IRD 100 to act as a beveled edge and longer towards the external buttress 112. The branches 470 may be of an elastomeric material that may bend with insertion and removal of the IRD 100 from the body cavity. For example, the branches 470 may be soft rubber discs, by way of example and not limitation. One or more of the branches 470 may extend into the body cavity during use of the IRD 100, and one or more of the branches 470 may remain in the body aperture during use of the IRD 100. As with other embodiments, a lubricant may be applied to the IRD 100, such as along the branches 470.

The passageway 264 runs through the IRD 100 with the first opening 420 configured for entry of the probe into the IRD 100 and the second opening 422 configured for exit of the probe from the IRD 100. This embodiment of the IRD 100 may have only the closed state for sliding the probe into the IRD 100 when the probe is not in the body aperture or the body cavity, as shown.

Figure 55:
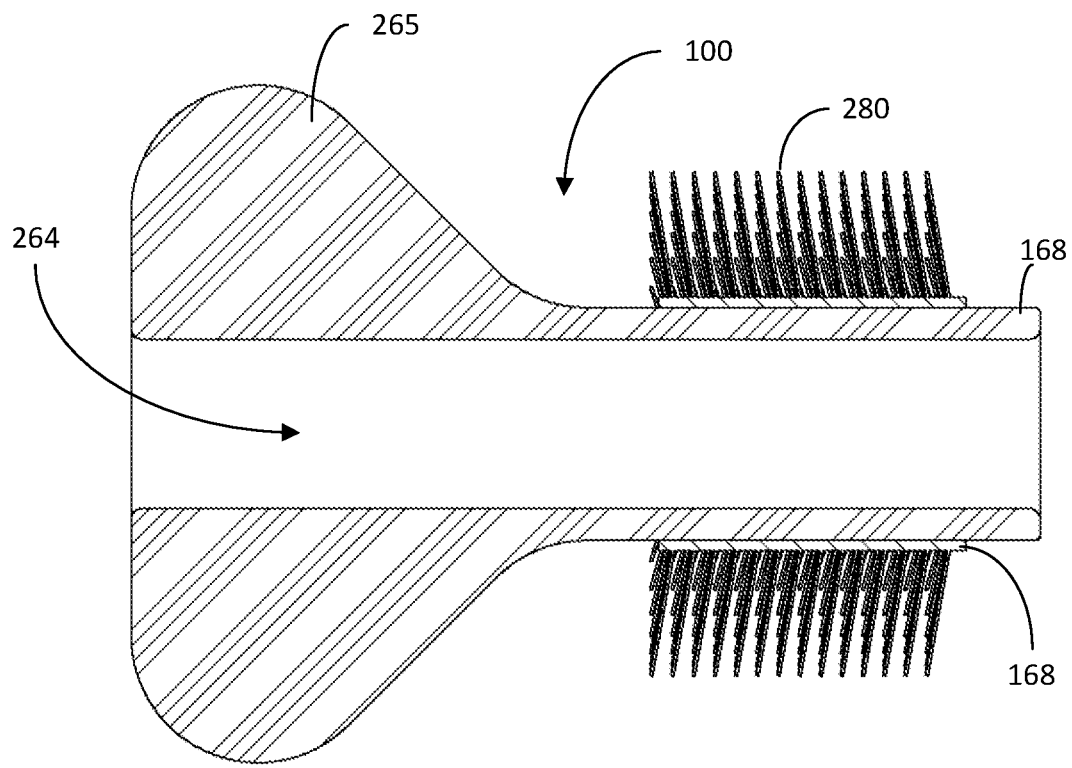
FIG. 55 shows in cross-section an insufflation retention device in accordance with various embodiments.
Figure 56:
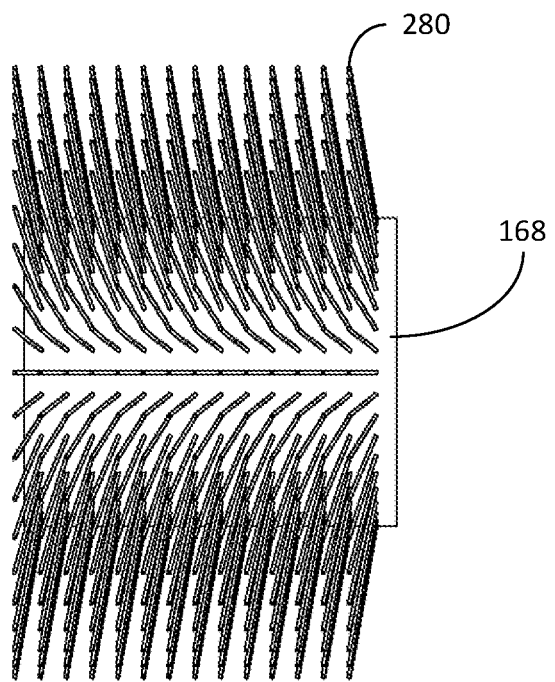
FIG. 56 shows in perspective view the insufflation retention device of FIG. 55 in accordance with various embodiments.

FIG. 55 shows in cross-section and FIG. 56 shows in perspective views another embodiment of the IRD 100. This embodiment shows O-ring type structures 280 external to the passageway structure 265. The O-ring type structures 280 may be substantially of the same length. The O-ring type structures 280 may be provided by the internal buttress portion 168 externally affixed to the passageway structure 265. The embodiment may look somewhat like a long "fur" collar that combined with lubricant may form an effective seal. While the O-ring type structures 280 may extend substantially parallel to each other and substantially perpendicular to the passageway structure 265, the O-ring type structures 280 may extend diagonally and substantially non-perpendicular to the passageway structure 265. Orientation of the O-ring type structures 280 may facilitate retention of the insufflation retention material. Of course, the O-ring type structures 280 may be flexible and change orientation when inserted and retracted from the body aperture or the body cavity.

Figure 57:
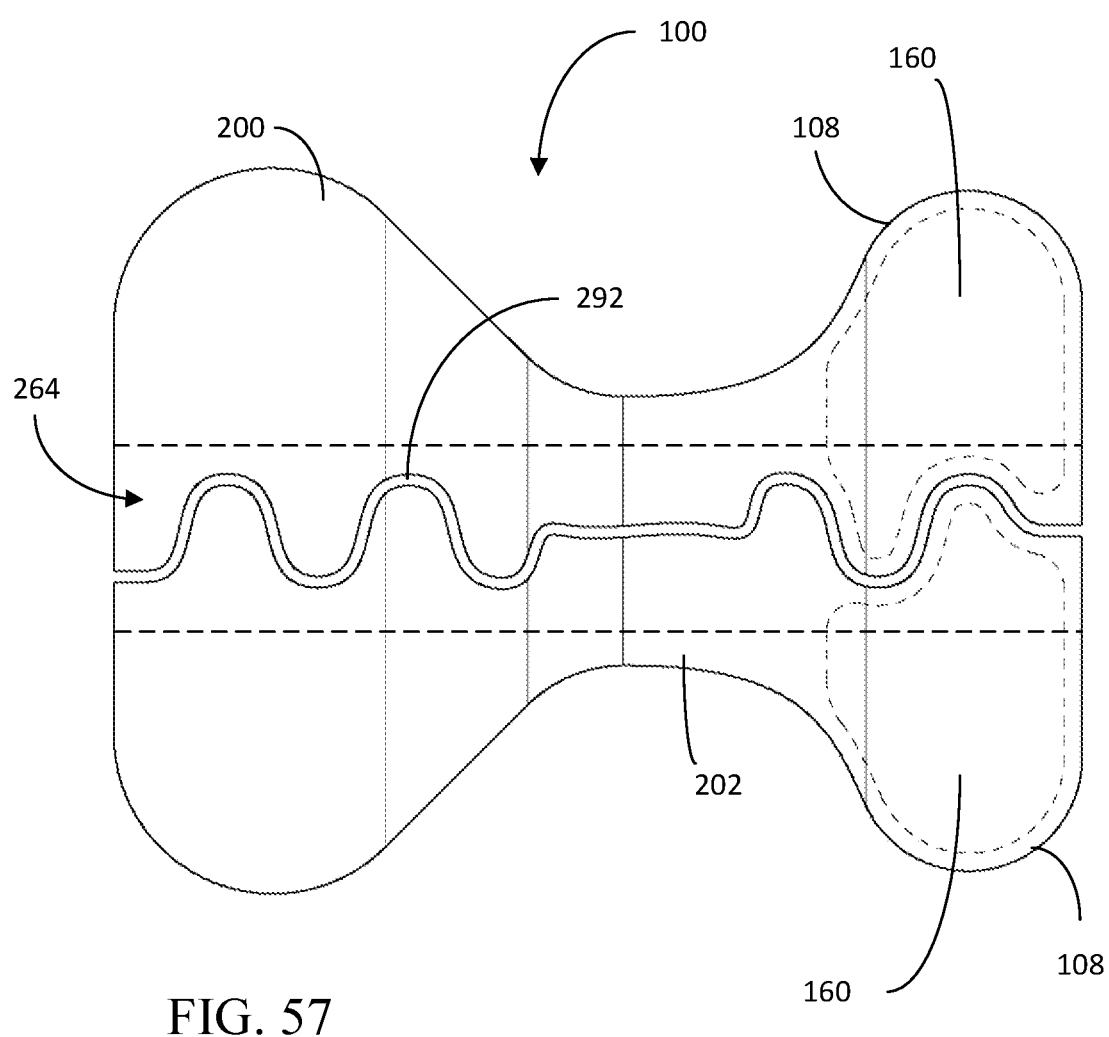
FIG. 57 shows in cross-section another insufflation retention device in accordance with various embodiments.

FIG. 57 shows a cross-section another embodiment of the IRD 100. A convoluted path of the seam 292 between the first body component 200 and the second body component 202 may help align the first body component 200 with the second body component 202 when the first body component 200 and the second body component 202 are transitioned from the open state to the closed state by the user. The passageway 264 runs through the combination of the first body component 200 and the second body component 202. The first body component 200 may have the internal cavity 160 of the internal buttress 108, so the internal buttress 108 of the first body component 200 may expand from a contracted or unexpanded state upon introduction of the expansion material. The second body component 202 may have the internal cavity 160 of the internal buttress 108, so the internal buttress 108 of the second body component 202 may expand from a contracted or unexpanded state upon introduction of the expansion material. The internal cavity 160 of the internal buttress 108 of the first body component 200 may not be in fluid communication with the internal cavity 160 of the internal buttress 108 of the second body component 202 in this embodiment.

Figure 58:
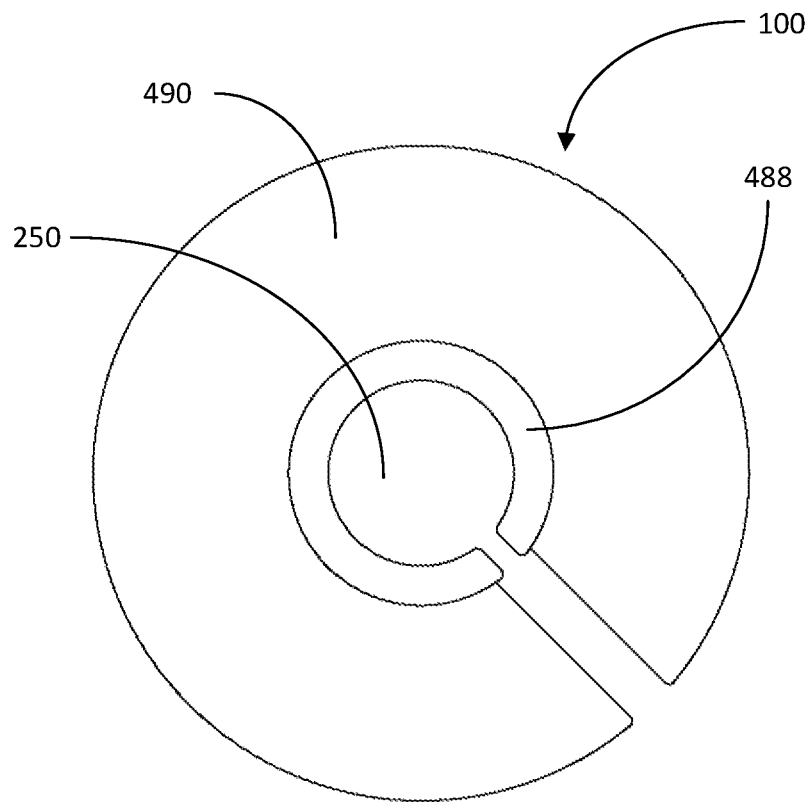
FIG. 58 shows in cross-section an insufflation retention device in accordance with various embodiments.
Figure 59:
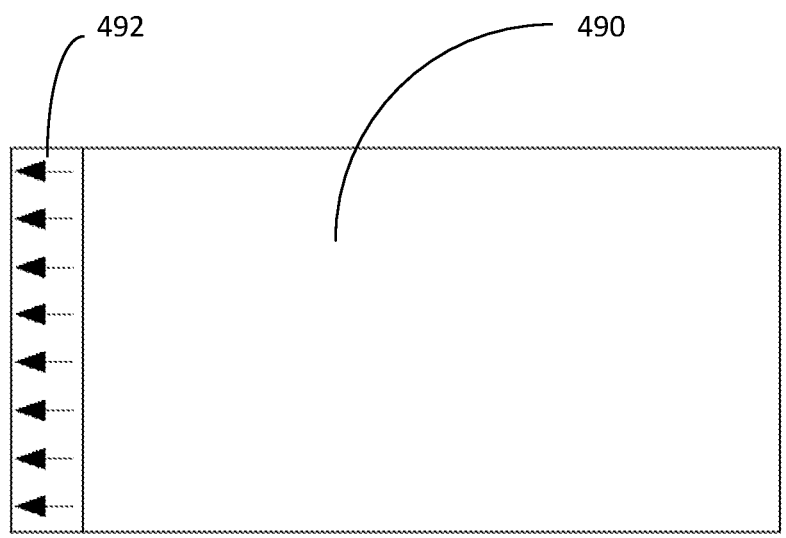
FIG. 59 shows in plan view a portion of the insufflation retention device of FIG. 58 in accordance with various embodiments.

FIG. 58 shows a cross-section of another embodiment of the IRD 100. Any suitable materials such as an elastomeric material 488, such a thermoplastic elastomer or other elastomeric material, may be applied around the probe 250 and an adhesive 490, as shown in FIG. 59, with an adhesive edge 492 may be used to put the IRD 100 in a closed state about the IRD 100.

Figure 60:
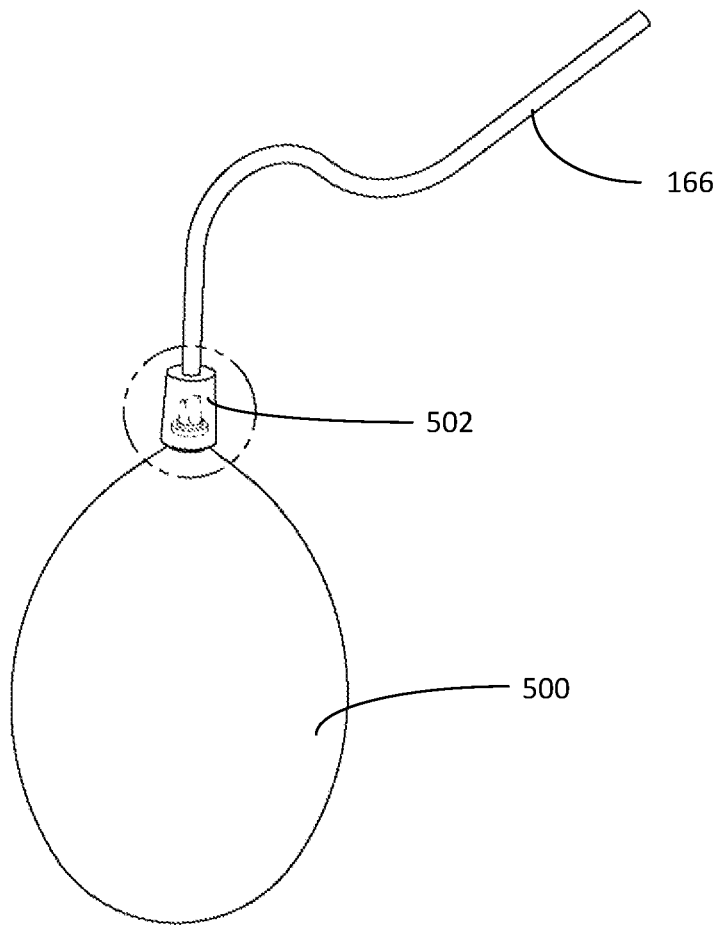
FIG. 60 (A) shows in plan view a pressure cuff pump, valve, and expansion material line in accordance with various embodiments.
Figure 60:
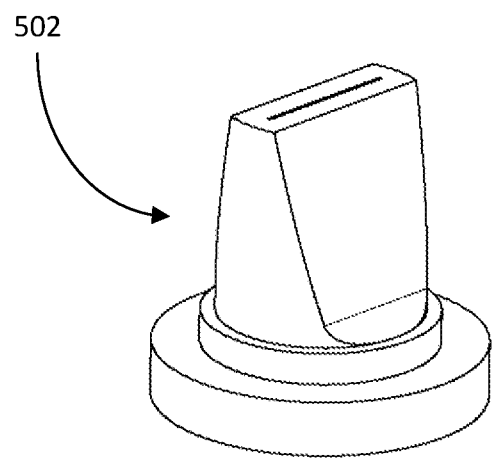

FIG. 60 (A) shows an isometric few of a pressure cuff pump 500 that may act as a source of expansion material through the expansion material line 166 for expansion of the internal cavity of the internal buttress or the external buttress. The pressure cuff pump 500 is squeezed for inflation. One could pinch to open one-way valve for deflation. A one-way duck bill valve 502 may be included, as shown in FIG. 60 (B). A syringe could be used for inflation, along with the other sources contemplated by one skilled in the art. As shown previously, the IRD 100 may need a valve to hold the expansion material after inflation of the internal buttress, the external buttress, or the midportion.

Figure 61:
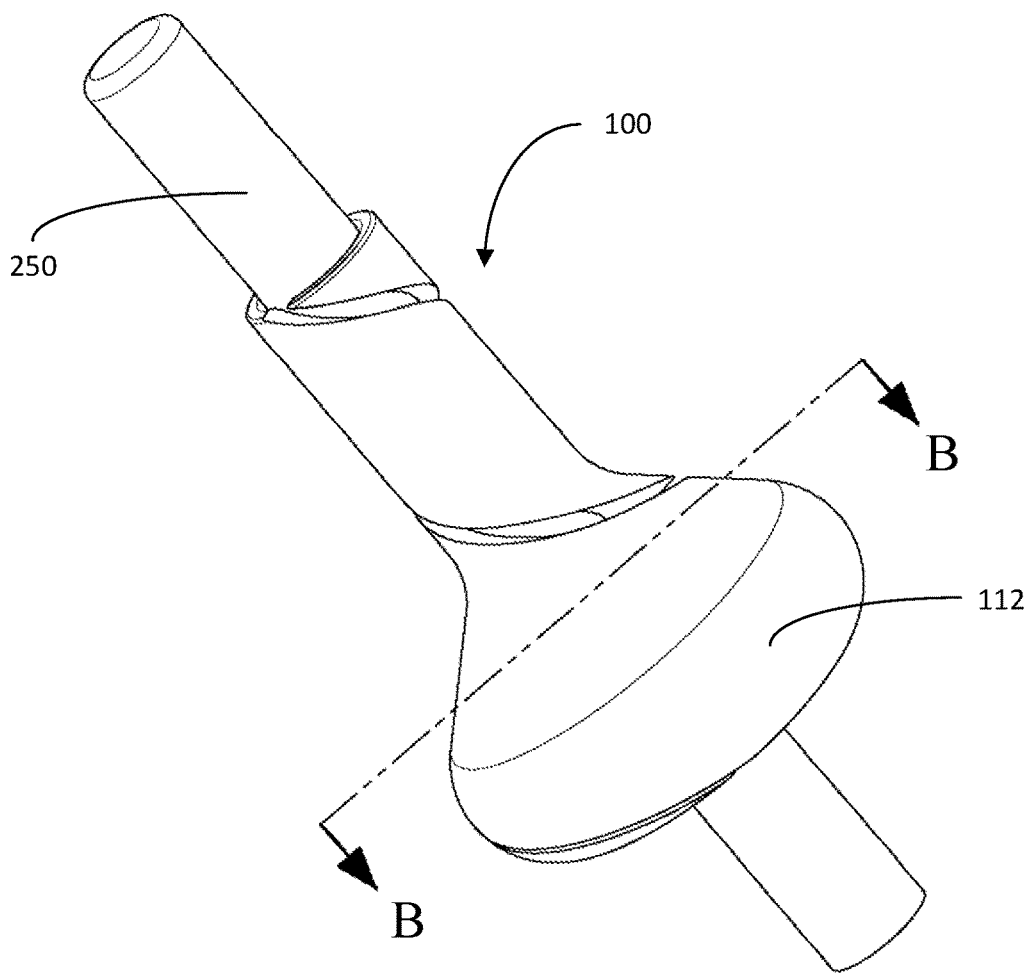
FIG. 61(A) shows an isometric view of another insufflation retention device in accordance with various embodiments.
FIG. 61(B) shows in cross-section the insufflation retention device of FIG. 60 (A) it accordance with various embodiments.
Figure 61:
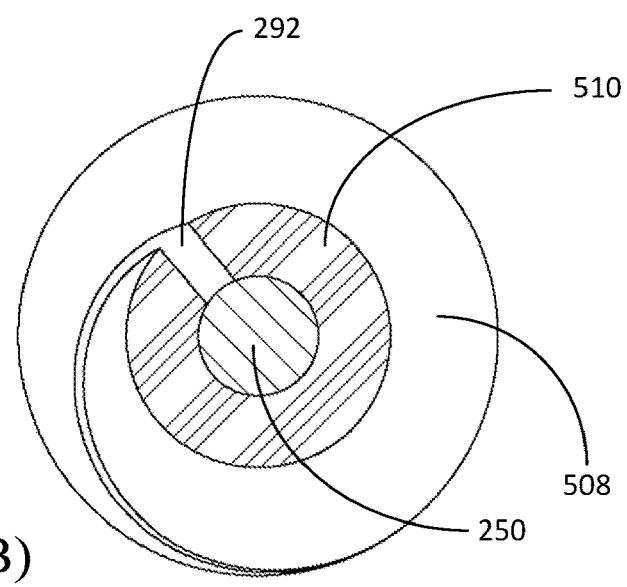

FIG. 61(A) shows an isometric view of another embodiment of the IRD 100. A soft thermoplastic elastomer 508 may be over molded on a rigid core 510. The rigid core 510 is more rigid than the soft thermoplastic elastomer 508. The rigid core 510 may be made of polypropylene, or other suitable material. The soft thermoplastic elastomer 508 may have a rating of about 50 A durometer, or other suitable rating. FIG. 61(B) shows the IRD 100 in cross-section with the probe 250 within the rigid core 510. During use, the seam 292 seen between the surfaces may be absent as the IRD 100 is inserted into the body aperture, the body cavity, or both. The IRD 100 may include the internal buttress, such as a balloon.

As shown throughout the disclosure in the various embodiments, the internal buttress 108 and the external buttress 112 in some embodiments are not configured to engage the probe 250 and therefore the internal buttress 108 and the external buttress 112 may not contribute to the seal between the IRD 100 and the probe 250. In other embodiments, the internal buttress 108 and the external buttress 112 are configured to engage the probe 250 and therefore the internal buttress 108 and the external buttress 112 may contribute to the seal between the IRD 100 and the probe 250. Whether the internal buttress 108 and the external buttress 112 engage the probe 250, the internal buttress 108 and the external buttress 112 may contribute to the seal between the IRD 100 and the body 102, such as the body cavity 104, the body aperture 106, and the wall 120 of the body aperture 106.

Of course, care is taken to optimize the contact of the internal buttress 108, the external buttress 112, and other portions of the IRD 100 with the body 102, the body cavity 104, and the body aperture 106, and other aspects of a patient to minimize the risk for pressure necrosis or other untoward side effects from using the IRD 100. This care may be implemented by having a predetermined volume for the expansion material, which will in turn establish a predetermined pressure that the internal buttress 108, the external buttress 112, etc. of the IRD 100 exerts on the body 102, the body cavity 104, the body aperture 106, etc.

A method of using the IRD 100 may comprise the following steps. At the first step, the IRD 100 is inserted through the body aperture 106 of the body 102 into the body cavity 104 of the body 102. At the second step, the insufflation material is injected into the body cavity 104. At the third step, a user uses a probe to perform a diagnostic intervention, a therapeutic intervention, or both a diagnostic intervention and a therapeutic intervention. Further steps are contemplated. For example, and not by way of limitation, the probe may be inserted through the body aperture 106 before, after, or in conjunction with the IRD being inserted through the body aperture 106.

It is to be understood that even though numerous characteristics and advantages of various embodiments of the present disclosure have been set forth in the foregoing description, together with details of the structure and function of various embodiments of the disclosure, this detailed description is illustrative only, and changes may be made in detail, especially in matters of structure and arrangements of parts within the principles of the present disclosure to the full extent indicated by the broad general meaning of the terms in which the appended claims are expressed.

What is claimed is:

1. An insufflation retention device comprising:
   an internal buttress configured to inhibit removal of the internal buttress from a body cavity through a body aperture of a body, wherein the internal buttress has an unexpanded state and an expanded state after introduction of an expansion material;
   an external buttress coupled to the internal buttress, the external buttress configured to inhibit entry of the external buttress into the body cavity through the body aperture, wherein the external buttress only has an expanded state and does not have an unexpanded state;
   a passageway extending through the internal buttress and the external buttress that is configured for passage of a probe in contacting engagement with the body cavity, wherein the passageway is configured to be open without the probe present in the passageway such that an insufflation material introduced into the body cavity is not retained in the body cavity;
   a seam runs from an exterior surface of the passageway through to an interior surface of the passageway, wherein the seam extends all the way from the internal buttress to the external buttress, wherein the internal buttress has a first balloon that is internal to the passageway and a separate, second balloon that is external to the passageway, and the first balloon and the second balloon are in fluid communication, but the first balloon and the second balloon do not go around an end of the internal buttress.

2. The insufflation retention device of 1, wherein the internal buttress in the expanded state is configured to be contactingly adjacent the probe.

3. The insufflation retention device of 1, wherein the internal buttress in the expanded state is configured to not be contactingly adjacent to the probe.

4. The insufflation retention device of 1, wherein the passageway is configured for passage of the probe from a first opening in the external buttress to a second opening in the internal buttress.

5. The insufflation retention device of 1, wherein the seam is configured to extend from a first opening in the external buttress to a second opening in the internal buttress, such that the passageway has an open state that does not retain the insufflation material when the probe is not present, and a closed state that does retain the insufflation material when the probe is in the passageway.

* * * * *